US011548845B2

(12) United States Patent
Bolling et al.

(10) Patent No.: US 11,548,845 B2
(45) Date of Patent: *Jan. 10, 2023

(54) METHODS OF ISOLATING PHENOLS FROM PHENOL-CONTAINING MEDIA

(71) Applicant: WISCONSIN ALUMNI RESEARCH FOUNDATION, Madison, WI (US)

(72) Inventors: Bradley Bolling, Madison, WI (US); Yuwei Wu, Madison, WI (US); Danielle Voss, Wrightstown, WI (US); Matthew Dorris, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/470,539

(22) Filed: Sep. 9, 2021

(65) Prior Publication Data

US 2021/0403401 A1  Dec. 30, 2021

Related U.S. Application Data

(63) Continuation of application No. 17/003,625, filed on Aug. 26, 2020, now Pat. No. 11,142,492.

(60) Provisional application No. 62/891,644, filed on Aug. 26, 2019.

(51) Int. Cl.

| *C07C 37/72* | (2006.01) |
|---|---|
| *C07C 39/04* | (2006.01) |
| *B01D 11/00* | (2006.01) |
| *C07C 37/86* | (2006.01) |
| *B01D 11/04* | (2006.01) |

(52) U.S. Cl.
CPC .......... *C07C 37/86* (2013.01); *B01D 11/0419* (2013.01); *B01D 11/0492* (2013.01); *C07C 37/72* (2013.01); *C07C 39/04* (2013.01)

(58) Field of Classification Search
CPC ......... C07C 37/72; C07C 37/86; C07C 39/04; C07C 39/08; C07C 39/10; B01D 11/0419
See application file for complete search history.

(56) References Cited

U.S. PATENT DOCUMENTS

| 4,049,686 A | 9/1977 | Ringers et al. |
| 4,174,296 A | 11/1979 | Kass |
| 5,043,323 A | 8/1991 | Bombardelli et al. |
| 6,703,000 B2 | 3/2004 | Ning et al. |
| 7,678,931 B2 | 3/2010 | Fichtali et al. |

FOREIGN PATENT DOCUMENTS

EP  0654527 A1  11/1994

OTHER PUBLICATIONS

Alam, M.A., Sughan N., Rahman, M.M., Uddin, S.J., Reza, H.M., Sarker, S.D. Effect of Citrus Flavonoids, Naringin and Naringenin, on Metabolic Syndrome and Their Mechanisms of Action. *Advances in Nutrition*, 2014, 5, 404-417.
Alberts, B., Johnson, A., Lewis J. et al. Molecular Biology of the cell. 4th ed. New York: Garland Science 2002. (Book—Copy Not Provided).
American lecithin company guide to use and select lecithins and phospholipids. (2020) Available online at: http://phosal.com/lecithin_2009.pdf.
Apostolova, E., Spaseska, B., Crcarevska, M.S., Dodv, M.G., Raichki, R.S. An overview of phytosomes as a novel herbal drug delivery system. *International Symposium at Faculty of Medical Sciences*. 2015, 1, 95-96.
Aude, M., Florence, E.L. Encapsulation of Natural Polyphenolic Compounds: A Review. *Pharmaceutics*. 2011, 3, 793-829.
Awad, T.S., Moharram, H.A., Shaltout, O.E., Asker, D., Youssef, M.M. Application of ultrasound in analysis, processing and quality control of food: a review. *Food Res. Int.* 2012, 48, 410-427.
Becher, P. (2001) *Emulsions: theory and Practice*, 3rd edn., American Chemical Society, Washington, DC. (Book—Copy Not Provided).
Bindr, H., Zschörnig, O. The effect of metal cations on the phase behavior and hydration characteristics of phospholipid membranes. *Chemistry and physics of lipids*. 2002, 115, 39-61.
Bloom, M., Evans, E., Mouritsen, O.G. Physical properties of the fluid lipid-bilayer component of cell membranes: a perspective. *Q. Rev. Biophys.* 1991, 24, 293-397.
Bonarska-Kujawa, D., Pruchnik. H., Kleszczyńska, H. Interaction of selected anthocyanins with erythrocytes and liposome membranes. *Cell. Mol. Biol. Lett.* 2012, 17, 289-308.
Brittes, J., Lucio, M., Nunes, C., Lima, J.L.F.C., Reis, S. Effects of resveratrol on membrane biophysical properties: relevance for its pharmacological effects. *Chem. Phys. Lipids*. 2010. 163, 747-754.
Brouillard, R., Dubois, J.E. Mechanism of the structural transformations of anthocyanins in acidic media. *J. Am. Chem. Soc.* 1977, 99, 1359-1364.
Bueschelberger et al., Emulsifiers in Food Technology, Second Edition. Ed. Viggo Norn., 2015, John Wiley & Sons, Ltd., Chapter 2, "Lecithins," pp. 21-60. (Book—Copy Not Provided).
Carlsson, A., in: F. D. Gunstone (Ed.), Phospholipid Technology and Applications, The Oily Press, Bridgwater (UK) 2008. (Book—Copy Not Provided).
Cassidy, A., Hanley, B., Lamuela-Raventos, R.M. Isoflavones, lignans and stilbenes—Origins, metabolism and potential importance to human health. *J. Sci. Food Agric*. 2000, 80, 1044-1062.

(Continued)

*Primary Examiner* — Sikarl A Witherspoon
(74) *Attorney, Agent, or Firm* — Daniel A. Blasiole; DeWitt LLP

(57) ABSTRACT

Methods of isolating phenols from phenol-containing media. The methods include combining a phospholipid-containing composition with the phenol-containing medium to generate a combined medium, incubating the combined medium to precipitate phenols in the combined medium and thereby form a phenol precipitate phase and a phenol-depleted phase, and separating the phenol precipitate phase and the phenol-depleted phase. The methods can further include extracting phenols from the separated phenol precipitate phase. The extracting can include mixing the separated phenol precipitate phase with an extraction solvent to solubilize in the extraction solvent at least a portion of the phenols originally present in the phenol precipitate phase.

20 Claims, 21 Drawing Sheets

(56) References Cited

OTHER PUBLICATIONS

Castaneda-Ovando, A., Pacheco-Hernandez, M.D., Paez-Hernandez, M.E., Rodriguez, J.A., Galan-Vidal, C.A. Chemical Studies of anthocyanins: A review. *Food Chemistry*. 2009, 113, 859-871.

Chen, L.Y., Cheng, C.W., Liang, J.Y. Effect of esterification condensation on the Folin-Ciocalteu method for the quantitative measurement of total phenols. *Food Chem*. 2015, 170, 10-15.

Chung, C., Rojanasasithara, T., Mutilangi, W., McClements, D.J. Enhanced stability of anthocyanin-based color in model beverage systems through whey protein isolate complexation. *Food Res Int*. 2015, 76, 761-768.

Clifford, M.N. Chlorogenic acids and other cinnamates—nature occurrence and dietary burden. *J. Sci. Food Agric*. 1999, 79, 362-72.

Cravotto, G., Binello, A., Orio, L. Green extraction techniques. *Agro. Food Ind. Hi-Tech*. 2011, 22, 57-59.

Crozier, A., Burns, J., Aziz, A.A., Stewart, A.J., Rabiasz, H.S., Jenkins, G.I., Edwards, C.A., Lean, M.E.J. Antioxidant flavonols from fruits, vegetables and beverages: measurements and bioavailability. *Biol. Res*. 2000, 33, 79-83.

Crozier, A., Lean, M.E.J., McDonald, M.S. Black, C. Quantitative analysis of the flavonoid content of commercial tomatoes, onions, lettuce, and celery. J. Agric. Food Chem. 1997, 45, 590.595.

Davies, J. T. (1957), "A Quantitative Kinetic Theory of Emulsion Type. I. Physical Chemistry of the Emulsifying Agent", Gas/;Liquid and Liquid/Liquid Interfaces. *Proceedings of 2nd International Congress Surface Activity*, 1: 426-438.

Davis, H.T. Factors Determining Emulsion Type: Hydrophile-Lipophile Balance and Beyond, Colloids Surf. A. 1994, 91:9, 9-24.

De Granada-Flor, A., Sousa, C., Filipe, H.A.L., Santos, M.S., de Almeida, R.F.M. Quercetin dual interaction at the membrane level. *Chemical Communications*. 2019, 55, 1750-1753.

De Groot, H., Rauen, U. Tissue injury by reactive ocygen species and the protective effects of flavonoids. *Fundam. Clin. Pharmacol*. 1998, 12, 249-255.

De Kroon, A.I.P.M., Rijken, P.J., De Smet, C.H. Checks and balances in membrane phospholipid class and acyl chain homeostasis, the yeast perspective. *Prog. Lipid Res*. 2013, 52, 374-394.

De Simón, B.F., Hernández, T., Estrella, I. et al. Variation in phenol content in grapes during ripening: low-molecular-weight phenols. *Z Lebensm. Unters. Forch*. 1992, 194, 351-354.

Dey, P.M., Harborne, J.B. Phenolic metabolism (Eds.). Plant Biochemistry, Academic, London (1997). (Book—Copy Not Provided).

Do, Q.D., Angkawijaya, A.E., Tran-Nguygen, P.L. et al. Effect of extraction solvent on total phenol content, total flavonoid content, and antioxidant activity of Limnophilia aromatica. *J. Food and Drug Analysis*. 2014, 22, 296-302.

Duarte Martino, H.S., Dos Santos Dias, M.M., Noratto, G., Talcott, S., Mertens-Talcott, S. U. Anti-lipidaemic and anti-inflammatory effect of açai (Euterpe oleracea Martius) polyphenols on 3T2-L1 adipocytes. *Journal of Functional Foods*. 2016, 23, 432-443.

Elendran, S., Wang. L.W., Prankered, R., Palanisamy, U.D. The physicochemical properties of geraniin, a potential antihyperglycemic agent. *Pharmaceutical Biology*. 2015, 53, 1719-1726.

Erickson, D.R., Degumming and Lecithin Processing and Utilization, in Practical Handbook Soybean Processing and Utilization, edited by D.R. Erickson, AOCS Press, Champaign, 1995, 174- 183. (Book—Copy Not Provided).

Everette, J.D., Bryant, Q.M., Green, A.M., Abbey, Y.A., Wangila, G.W., Walker, R.B. Thorough study of reactivity of various compund classes toward the Folin-Ciocalteu reagent. *J. Agric. Food Chem*. 2010, 58, 8139-8144.

F. D. Gunstone; John L. Harwood; Albert J. Dijkstra (2007). The Lipid Handbook. Boca Raton, FL: CRC Press. pp. 319-320. (Book—Copy NOt Provided).

Fossen, T., Cabrita, L., Andersen, O.M. Colour and stability of pure anthocyanins influenced by pH including the alkaline region. *Food Chem*. 1998, 63, 435-440.

García-Lafuente, A., Guillamón, E., Villares, A., Rostagno, M.A., Martínez, J.A. Flavonoids as anti-inflammatory agents: implication in cancer and cardiovascular disease. *Inflamm. Res*. 2009, 58, 537-552.

Ghasemzadeh A., Ghasemzadeh N. Flavonoids and phenolic acids: Role and biochemical activity in plants and human. *J. Med. Plants Res*. 2011, 5, 6697-6703.

Giusti, M.M., Wrolstad, R. E. Anthocyanins. Characterization and measurement with UV-visible spectroscopy. In R.E. Wrolstad (Ed.), Current Protocols in Food Analytical Chemistry, NewYork:Wiley (2001). (Book—Copy Not Provided).

Gould, S.B. Membranes and evolution. *Curr. Biol*. 2018, 28, 381-385.

Graf, B.A., Milbury, P.E., Blumberg, J.B. Flavonols, flavones, flavanones, and human health: epidemiological evidence. *J. Med. Food*. 2005, 8, 281-90.

Grand View Research Global Polyphenols Market Analysis by Product, by Application and Region Forecasts to 2025 (2020). Available online at: https://www.grandviewresearch.com/press-release/global-polyphenols-market.

Griffin, William C. (1954), "Calculation of HLB Values of Non-Ionic Surfactants" (PDF), *Journal of the Society of Cosmetic Chemists*, 5 (4):249-56.

Gu, L., Kelm, M.A., Hammerstone, J.F., Beecher, G., Holden, J., Haytowitz, D., Gebhardt, S., Prior, R.L. Concentrations of proanthocyanidins in common foods and estimations of normal consumption. *J. Nutr*. 2004, 134, 613-617.

Hackman, R.M., Polagruto, J.A., Zhu, Q.Y. et al. Flavanols: digestion, absorption and bioactivity. *Phytochem. Rev*. 2008, 7, 195-208.

Hashimoto, T., Kumazawa, S., Nanjo, F., Hara, Y., Nakayama, T. Interaction of Tea Catechins with Lipid Bilayers Investigated with Liposome Systems. *Biosci. Biotechnol. Biochem*. 1999, 63, 2252-2255.

He, J., Giusti, M. M. Anthocyanins: Natural colorants with health-promoting properties. *Annual Review of Food Science and Technology*. 2010, 1, 163-187.

He, J.L., Luo, L.Y., Zeng, L. Recent Advances in Research on Preparation Technologies and Application of Tea Polyphenol Nanoparticales. *Food Sci*. 2011, 32, 317-322.

Heleno, S.A., Martins, A., Queiroz, M.J., Ferreira, I.C. Bioactivity of phenolic acids: metabolites versus parent compounds: a review. *Food Chem*. 2015, 173, 501-513.

Herbette, L., Napolitano, C., McDaniel, R. Direct determination of the calcium profile structure for dipalmitoyllecithin multilayers using neutron diffraction. *Biophysical journal*. 1984, 46, 677.

Hernández, E., Quezada, N., in: F.D. Gunstone (Ed.), Phospholipid Technology and Applications, The Oily Press, Bridgwater (UK) 2008. (Book—Copy Not Provided).

Herrero, M., Mendiola, J.A., Cifuentes, A., Ibáñez, E. Supercritical fluid extraction: recent advances and applications. *J. Chromatogr. A*. 2010, 1217, 2495-2511.

Herrmann, K. Occurrence and content of hydroxycinnamic and hydroxybenzoic acid compounds in foods. *Crit. Rev. Food Sci. Nutr*. 1989, 28, 315-347.

Hertog, M.G.L., Hollman, P.C.H., Katan, M.B. Content of potentially anticarcinogenic flavonoids of 28 vegetables and 9 fruits commonly consumed in the Netherlands. *J. Agric. Food Chem*. 1992, 40, 2379-2383.

Hertog, M.G.L., Hollman, P.C.H., van de Putte, B. Content of potentially anticarcinogenic flavonoids of tea infusions, wines and fruit juices. *J. Agric. Food Chem*. 1993, 41, 1242-1246.

Huang C.J., Zayas J.F. Phenolic acids contribution to tast characteristic of corn germ protein flour products. *J. Food Sci*. 1991, 56, 1308-1310.

Johansson, D., Bergenstahl, B. Lecithins in Oil-Continuous Emulsions—Fat Crystal Wetting and Interfacial Tension. J. Am. Oil Chem Soc. 1995, 72, 205-211.

Kajiya, K., Hojo, H., Suzuki, M., Nanjo, F., Kumazawa, S., Nakayama, T. Relationship between antibacterial activity of (+)-catechin derivatives and their interaction with a model membrane. *J. Agric. Food Chem*. 2004, 52, 1514-1519.

Kajiya, K., Kumazawa, S., Naito, A., Nakayama, T. Solid-state NMR analysis of the orientation and dynamics of epigallocatechin

(56) References Cited

OTHER PUBLICATIONS gallate, a green tea polyphenol, incorporated into lipid bilayers. Magn. Reson. Chem. 2008, 46, 174-177.

Kang, X., Zhang, Q., Wang, S., Huang, X., Jin, S. Effect of soy isoflavones on breast cancer recurrence and death for patients receiving adjuvant endocrine therapy. Can. Med. Assoc. J. 2010, 182, 1857-1862.

Kentish, S., Feng, H. Applications of power ultrasound in food processing. Annu. Rev. Food Sci. Technol. 2014, 5, 263-284.

King, J.W. Modern supercritical fluid technology for food applications. Annu. Rev. Food Sci. Technol. 2014, 5, 215-238.

Kong, J. M., Chia, L. S., Goh, N. K., Chia, T. F., Brouillard, R. Analysis and Biological Activities of Anthocyanins. Phytochemistry. 2003, 64, 923-933.

Košinová, P., Berka, K., Wykes, M. et al. Positioning of antioxidant Quercetin and its metabolites in lipid bilayer membranes: implication for their lipid-peroxidation inhibition. J. Phys. Chem. B. 2012, 116, 1309-1318.

Krishna, G., Wood, G.C., Sheth, B.B. Improving emulsification efficacy of lecithin by formulation design, I: Effect of adding a secondary surfactant. PDA. J. Pharm. Sci. Technol. 1998, 52, 331-336.

Krog, N.J. Food Emulsifiers and Their Chemical and Physical Properties. in Food Emulsions, edited by S.E. Friberg and K. Larsson, Marcel Dekker, New York, 1997, 141-188 (Book—Copy Not Provided).

Kuiper, G.G., Carlsson, B., Grandien, K., Enmark, E., Haggblad, J., Nilsson, S., Gustafsson, J.A. Comparison of the ligand binding specificity and transcript tissue distribution of estrogen receptors alpha amd beta. Endocrinology. 1997, 138, 863-870.

Kuiper, G.G., Lemmen, J.G., Carlsson, B., Corton, J.C., Safe, S.H., van der Saag, P.T., van der Burg, B., Gustafsson, J.A. Interaction of estrogenic chemicals and ohytoestrogens with estrogen receptor beta. Endocrinology. 1998, 139, 4252-4263.

Larsson, L. Stability of Emulsions Formed by Polar Lipids. Prog. Chem. Fats Other Lipids. 1987, 16m 163-169.

Lattanzio, V., De Cicco, V., Di Venere, D., Lima, G., Salerno, M. Antifungal activity of phenolics against fungi commonly encountered during storage. Ital. J. Food Sci. 1994, 6, 23-30.

Le Bourvellec, C., Guyot, S., Renard, C. M. G. C. Interactions Between Apple (Malus x domestica Borkh.) Polyphenols and Cell Walls Modulate the Extractability of Polysaccharides. Carbohydrate Polymers. 2009, 75, 251-261.

Lechtenberg, M., Zumdick, S., Gerhards, C., Schmidt, T.J., Hensel, A. Evaluation of analytical markers characterization different drying methods of parsley leaves (Petroselinum crispum L.). Pharmazie, 2007, 62, 949-954.

Lee, J., Durst, R. W., Wrolstad, R. E. Determination of Total Monomeric Anthocyanin Pigment Content of Fruit Juices, Beverages, Natural Colorants, and Wines by the pH Differential Method: Coolaborative Study. Journal of AOAC International. 2005, 88, 1269-1278.

Liu, D., Ma, F. Soybean Phospholipids. In Recent Trends for Enhancing the Diversity and Quality of Soybean Products; Krezhova, D., Ed.; InTech: Rijeka, Croatia (2011).

Lu, M., Qiu, Q., Luo, X., Liu, X., Sun, J., Wang, C., Lin, X., Deng, Y., Song, Y. Phyto-phospholipid complexes (phytosomes): A novel strategy to improve the bioavailability of active constituents. Asian Journal of Pharmaceutical Sciences. 2019, 14, 265-274.

Lundberg, B., Svens, E., Ekman, S. The hydration of phospholipids and phospholipid-cholesterol complexes. Chem. Phys. Lipids. 1978, 22, 285-292.

Maiti, K., Mukherjee, K., Gantait, A., Saha, B.P., Mukherjee, P.K. Curcumin-phospholipid complex: preparation, theraoeutic evaluation and pharmacokinetic study in rats. Int J Pharma. 2007, 330, 155-163.

Manach, C., Scalbert A., Morand C., Remesy C., Jimenez L. Polyphenols: Food sources and bioavailability. Am. J. Clin. Nutr. 2004, 79, 727-747.

Martin, D. A., Smyth, J. A., Liu, Z., Bolling, B. W. (2018). Aronia Berry (Aronia mitschurinii 'Viking') Inhibits Colitis in Mice and Inhibits T Cell Tumor Necrosis Factorα Secretion. Journal of Functional Foods, 44(February), 48-57. doi: 10.1016/j.jff.2018.02.025.

McIntosh, T.J., Magid, A.D. Phospholipid Hydration. In Phospholipids Handbook; Cecv, G., Ed.; Marcel Dekker, Inc: New York, NY, USA. 1993, 553-577.

Melcrová, A., Pokorna, S., Pullanchery, S., Kohagen, M., Jurkiewicz, P., Hof, M., Jungwirth, P., Cremer, P. S., Cwiklik, L. The Complex Nature of Calcium Cation Interations with Phospholipid Bilayers. Sci Rep. 2016, 6, 38035-38047.

Calcium Cation Interactions with Phospholipid Bilayers. Sci Rep. 2016, 6, 38035-38047.

Mrazkova, E., Hobza, P., Bohl, M., Gauger, D. R., Pohle, W. Hydration-Induced Changes of Structure and Vibrational Frequencies of Methylphosphocholine Studied as a Model of Biomembrane Lipids. J. Phys. Chem. B. 2005, 109, 15126-15134.

Mueller-Harvey, I., Mlambo, V., Sikosana, J.L.N., Smith, T. et al. Octanol-water partition coefficients for predicting the effects of tannins in ruminant nutrition. J. Agri. Food Chem. 2007, 55, 5436-5444.

Mullen, W., Marks, S., Crozier, A. Evaluation of phenolic compounds in commercial fruit juices and fruit drinks. J. Agri. Food Chem. 2007, 55, 3148-3157.

Neilson, Andrew P., O'Keefe, Sean F., and Bolling, Bradley W. High-Molecular-Weight Proanthocyanidins in Foods: Overcoming Analytical Challenges in Pursuit of Novel Dietary Bioactive Components Annu. Rev. Food Sci. Technol. 2016. 7:3.1-3.22.

Nonaka, G., Sakai, R., Nishioka, I. Hydrolysable tannins and proanthocyanidins from green tea. Phytochemistry. 1984, 23, 1753-1755.

Norn, Emulsifiers in Food Technology, Second Edition. Ed. Viggo Norn, 2015, John Wiley & Sons, Ltd., Chapter 3, "Ammonium Phosphatides," pp. 61-72. (Book—Coy Not Provided).

Nose, A., Hojo, M. Hydrogen bonding of water-ethanol in alcoholic beverages. J. Biosci. Bioeng. 2006, 102, 269-280.

Nyankson, E., DeCuir, M.J., Gupta, R.B. Soybean lecithin as a dispersant for crude oil spills. ACS Sustainable Chem. Eng. 2015, 3, 920-931.

Oancea, S., Stoia, M., Coman, D. Effects of extraction conditions on bioactive anthocyanin content of Vaccinium Corymbosum in the perspective of food application. Procedia Engineering. 2012, 42, 489-495.

Olivas-Aguirre, F.J., Rodrigo-García, J., Martúnez-Ruiz, N.D., Cárdenas-Robes, A.I. et al. Cyanidin-3-O-glucoside: Physical—Chemistry, Foodomics and Health Effects. Molecules. 2016, 21, 1264-1294.

Padayachee, A., Netzel, G., Netzel, M., Day, L., Zabaras, D., Mikkelsen, D., Gidley, M. J. Binding of Polyphenols to Plant Cell Wall Analogues—Part 1: Anthocyanins. Food Chemistry. 2012, 134, 155-161.

Padayachee, A., Netzel, G., Netzel, M., Day, L., Zabaras, D., Mikkelsen, D., Gidley, M. J. Binding of Polyphenols to Plant Cell Wall Analogues—Part 2: Phenolic Acids. Food Chemistry. 2012, 135, 2287-2292.

Pawlikowska-Pawlega, B., Kapral, J., Gawron, A. et al. Interaction of a quercetin derivative—lensoside Aβ with liposomal membranes. Biochimica et Biophysica Acta (BBA)—Biomembranes. 2018, 1860, 292-299.

Pekkinen, J., Rosa, N. N., Savolainen, O. I., Keski-Rahkonen, P., Mykkänen, J., Poutanen, K., Micard, V., Hanhineva, K. Distintegration of Wheat Aleurone Structure Has an Impact on the Bioavailability of Phenolic Compounds and Other Phytochemicals as Evidenced by Altered Urinary Metabolite Profile of Diet-induced Obese Mice. Nutrition and Metabolism. 2014, 11, 1-15.

Pereira, C., Hünenberger, P.H. Interaction of the sugars trehalose, maltose and glucose with a phospholipid bilayer: a comparative molecular dynamics study. J. Phys. Chem. B. 2006, 110, 15572-15581.

Perez-Jimenez, J., Neveu, V., Vos, F., Scalbert, A. Systematic analysis of the content of 502 polyphenols in 452 foods and beverages: An application of the phenol-explorer database. J. Agric. Food Chem. 2010, 58, 4959-4969.

(56) References Cited

OTHER PUBLICATIONS

Perrissoud, D., Testa, B. Inhibting or potentiating effects of flavonoids on carbon tetrachloride-induced toxicity in isolated rat hepatocytes. *Arzneimittelforschung.* 1986, 36, 1249-1253.

Phan, H.T.T., Yoda, T., Chahal, B., Morita, M. et al. Structure-dependent interactions of polyphenols with a biomimetic membrane system. *Biochimica et Biophysica Acta (BBA)—Membranes.* 2014, 1838, 2670-2677.

Pietta, R.G. Flavonoids as antioxidants. *J. Nat. Prod.* 2000, 63, 1035-1042.

Pires, L.N., Brandão, G.C., Teixeira, L.S.G. Determination of phospholipids in soybean lecithin samples via the phosphorus monoxide molecule by high-resolution continuum source graphite furnace molecular absorption spectrometry. *Food Chemistry.* 2017, 225, 162-166.

Plaza, M., Turner, C. Pressurized hot water extraction of bioactives. *Trend Anal Chem.* 2015, 71, 39-54.

Plaza. M., Abrahamsson, V., Turner, C. Extraction and neoformation of antioxidant compounds by pressurized hot water extraction from apple byproducts. *J. Agric. Food Chem.* 2013, 61, 5500-5510.

Price, K.R., Rhodes, M.J.C. Analysis of the major flavonol glycosides present in four varieties of onion (*Allium cepa*) and changes in composition resulting from autolysis. *J. Sci. Food Agric.* 1997, 74, 331-339.

Prior, R.L., Wu, X., Schaich, K. Standardized methods for the determination of antioxidant capacity and phenolics in foods and dietary supplements. *J. Agric. Food Chem.* 2005, 53, 4290-4302.

Prior, R.L.; Fan, E.; Ji, H.; Howell, A.; Nio, C.; Payne, M.J.; Reed, J. Multi-laboratory Validation of a Standard Method for Quantifying Proanthocyanidins in Cranberry Powders. *J. Sci. Food Agri.* 2010, 90, 1473-1478.

Pu, Y., Zhang, X., Zhang, Q. 20(S)-Proropanaxadiol Phospholipid Complex: Process Optimization, Characterization, in vitro Dissolution and Molecular Docking Studies. *Molecules,* 2016, 21, 1396-1417.

Ravindranath, M.H., Ramasamy, V., Moon, S., Ruiz, C., Muthugounder, S. Differential growth suppression of human melanoma cellse by tea (*Camellia sinensis*) epicatechins (ECG, EGC and EGCG). *Evid. Based Complement Alternat. Med.* 2009, 6, 523-530.

Renaud, S., de Lorgeril, M. Wine, alcohol, platelets, and the French paradox for coronary heart disease. *Lancet.* 1992, 339,1523-1526.

Revilla, E., Ryan, J.M., Martin, O.G. Comparison of several procedures used for the extraction of anthocyanins from red grapes. *J. Agric. Food Chem.* 1998, 46, 4592-4596.

Rodriguez-Saona, L., & Wrolstad, R. (2001). Extraction, Isolation, and Purification of Anthocyanins. In R.E. Wrolstad, T. E. Acree, E. A. Decker, M. H. Penner, D. S. Reid, S. J. Schwartz, C. F. Shoemaker, D. Smith, P. Spors (Eds.), *Handbook of Food Analytical Chemistry: Pigments, Colorants, Flavors, Texture, and Bioactive Food Components* (pp. 5-69). Hoboken, NJ: John Wiley & Sons, Inc (Book—Copy Not Provided).

Roobha, J.J., Saravanakumar, M., Aravindhan, K.M., Devi, P.S. The effect of light, temperature, pH on stability of anthocyanin pigments in Musa Acuminata Bract. *Research in Plant Biology.* 2011, 1, 5-12.

Rosa, N. N., Dufour, C., Lullien-Pellerin, V., Micard, V. Exposure or Release of Ferulic Acid from Wheat Aleurone: Impact on Its Antioxidant Capacity. *Food Chemistry.* 2013, 141, 2355-2362.

Rothwell, J.A., Day, A.J., Morgan, M.R. Experimental determination of octanol-water partition coefficients of quercetin and related flavonoids. J. Agric. *Food Chem.* 2005, 53, 4355-4360.

Sairam, P., Ghosh, S., Jena, S., Rao, K.N.V., Banji, D. Supercritical fluid extraction (SFE)—an overview. *J. Res. Pharma. Sci.* 2012, 2, 112-120.

Sakai, T., Kogiso, M. Soy isoflavones and immunity. *J. Med. Investig.* 2008, 55, 167-173.

Sanchez, M.C., Cao, G., Ou, B., Prior, R.L. Anthocyanin and proanthocyanidin content in selected white and red wines. Oxygen radical absorbance capacity comparison with nontraditional wines obtained from highbush blueberry. *Journal of Agricultural and Food Chemistry.* 2003, 51, 4889-4896.

Santos-Buelga, C., Scalbert, A. Proanthocyanidins and tannin-like compunds in human nutrition. *J. Food Sci. Agric.* 2000, 80, 1094-1117.

Scalbert A. Quantitative methods for the estimation of tannins in plant tissues. In: Plant polyphenols: synthesis, properties, and significance. Hemmingway RW and Laks PS. (ed). Plenum Press. New York, NY. 1992, 259-280. (Book—Copy Not Provided).

Schneider, M. Fractionation and Purification of Lecithin, in Lecithins: Sources, Manufacture, & Uses, edited by B.F. Szuhaj, American Oil Chemists' Society, Champaign, 1989, 109-130.

Scholfield, C. R. (Oct. 1981). "Composition of Soybean Lecithin". *Journal of the American Oil Chemists' Society.* 58 (10): 889-892.

Shahidi, F., Nacsk, M. Food Phenolics: Sources, Chemistry, Effects, and Application. Technomic Publishing Co., Inc., Lancaster, PA (1995). (Book—Copy Not Provided).

Singleton, V.L., Rossi, J.A. Colorimetry of total phenolics with phosphomolybdic-phosphotungstic acid reagents. *Am. J. Enol. Vitic.* 1965, 16, 144-158.

Singleton, V.L.; Orthofer, R.; Lamuela-Raventós, R.M. Analysis of Total Phenols and Other Ocidation Substrated and Antioxidants by Means of Folin-Ciocalteu Reagent. *Methods Enzymol.* 1999, 299, 152-178.

Sirk, T.W., Brown, E.F., Sum, A.K., Friedman, M. Molecular dynamics study on the biophysical interactions of seven green tea catechins with lipid bilayers of cell membranes. *J. Agric. Food. Chem.* 2008, 56, 7750-7758.

Souquet, J., Cheynier, V., Brossaud, F., Moutounet, M. Polymeric proanthocyanidins from grape skins. *Phytochemistry.* 1996, 43, 509-512.

Srivastava, J.K., Gupta, S. Extraction, characterization, stability and biological activity of flavonids isolated from chamomile flowers. *Mol. Cell Pharmacol.* 2009, 1(3), 138.

Stalikas, C.D. Extraction, separation, and detection methods for phenolic acids and flavonoids. *J. Sep. Sci.* 2007, 30, 3268-3295.

Suetsugu, S., Kurisu, S., Takenawa, T. Dynamic Shaping of Cellular Membranes by Phospholipids and Membrane-Deforming Proteins. *Physiological Reviews.* 2014, 94, 1219-1248.

Svehlíková V., Repcák M. Apigenin chemotypes of *Matricaria chamomilla.* L. *Biochem. Syst. Ecol.* 2006, 34, 654-657.

Tadeo, J.L., Sánchez- Brunete, C., Albero, B., García-Valcárcel, A.I. Application of ultrasound-assisted extraction to the determination of contaminants in food and soil samples. *J. Chromatogr. A.* 2010, 1217, 2415-2440.

Tamba, Y., Ohba, S., Kubota, M., Yoshioka, H., Yamazaki, M. Single GUV method reveals interaction of tea catechin (-)-epigallocatechin gallate with lipid membranes. *Biophys. J.* 2007, 92, 3178-3194.

Tanaka, Y., Sasaki, N., Ohmiya, A. Biosynthesis of Plant Pigments: Anthocyanins, Betalains, Carotenoids. *Plant J.* 2008, 54, 733-749.

Teo, C.C., Tan, S.N., Yong, J.W., Hew, C.S., Ong, E.S. Pressurized hot water extraction (PHWE). *J. Chromatogr. A.* 2010, 1217, 2484-2494.

Tian, B.R., Liu, J.Y., Ge, H.R., Wang, Z.Z. et al. The design, synthesis and characterization of resveratol derivatives modified by different γ-Aminobutyric Acid Esters. *Journal of Chemistry.* 2019, 2019, 1-6.

Tomas-Barberan, F.A., Clifford, M.N. Flavanones, chalcones and dihydrochalcones—nature, occurrence and dietary burden. *J. Sci Food. Agric.* 2000, 80, 1073-1080.

Trouillas, P., Sancho-García, J.C., De Freitas, V., et al. Stabilizing and modulating color by copigmentation: insights from theory and experiment. *Chem Rev.* 2016, 116, 4937-4982.

Tsuchiya, H. Effects of Greent Tea Catechins on Membrane Fluidity. *Pharmacology.* 1999, 59, 34-44.

Tsuchiya, H. Structure-dependent membrane interaction of flavonoids associated with their bioactivity. *Food Chem.* 2010, 120, 1089-1096.

Tsui, F. C., Ojcius, D. M., Hubbell, W. L. The Intrinsic pKa Values for Phosphatidylserine and Phosphatidylethanolamine in Phosphatidylcholine Host Bilayers. *Biophys J.* 1986, 49, 459-68.

Uekusa, Y., Kamihira, M., Nakayama, T. Dynamic Behavior of Tea Catechins Interacting with Lipid Membranes as Determined by NMR Spectroscopy. *J. Agric. Food Chem.* 2007, 55, 9986-9992.

(56) References Cited

OTHER PUBLICATIONS

Uhrikova, D., Kucerka, N., Teixeira, J., Gordeliy, V., Balgave, P. Structural changes in dipalmitoylphosphatidylcholine bilayer promoted by Ca2+ ions: a small-angle neutron scattering strudy. *Chemistry and physics of Lipids*. 2008, 155, 80-89.

Van Nieuwenhuyzen, W. Lecithin production and properties. *J. Am Oil Chem Soc*. 1976, 53, 425-427.

Van Nieuwenhuyzen, W., Tomás, M.C. Update on vegetable lecithin and phospholipid technologies. *Eur. J. Lipid Sci. Technol*. 2008, 110, 472-486.

Vergara-Salinas, J.R., Cuevas-Valenzuela, J., Pérez-Correa, J.R. Pressurized hot water extraction of polyphenols from plant material. In: Kumar VG, Tuohy MG, Lohani M, O'Donovan A, editors. Biotechnology of bioactive compounds: sources and applications. New Jersey: John Wiley & Sons Inc. 2015, 63-101.

Vilkhu, K., Mawson, R., Simons, L., Bates, D. Applications and opportunities for ultrasound-assisted extraction in the food industry—a review. *Innov. Food Sci. Emerg. Technol*. 2008, 9, 161-169.

Vita, J.A. Polyphenols and cardiovascular disease: effects on endothelial and platelet function. *Am. J. Clin. Nutr*. 2005, 81(suppl), 292S-297S.

Wang, Y., Singh, A.P., Hurst, W.J., Glinski, J.A., Koo, H., Vorsa, N. Influence of degree-of-polymerization and linkage on the quantification of proanthocyanidins using 4-Dimethylaminocinnamaldehyde (DMAC) *Assay. J. Agric. Food Chem*. 2016, 64, 2190-2199.

Weete, J.D., Betageri, S., Griffith, G.L. Improvement of Lecithin as an Emulsifier for Water-in-Oil Emulsions by Thermalization. *J. Am. Oil Chem Soc*. 1994, 71, 731-737.

Wei, L., Kelly, A.L., Song, M. Emulsion-based Encapsulation and Delivery Systems for Polyphenols. *Trends Food Sci Tech*. 2016, 47, 1-9.

West, M.E., Mauer, L.J. Color and chemical stability of a variety of anthocyanins and ascorbic acid in solution and powder forms. *Journal of Agricultural and Food Chemistry*. 2013, 61, 4169-4179.

Wu, X., Prior, R. L. Systematic identification and characterization of anthocyanins by HPLC-ESI-MS/MS in common foods in the United States: Fruits and berries. *Journal of Agricultural and Food Chemistry*. 2005, 53, 2589-2599.

Wu. Y., Wang, T. Soybean Lecithin Fractionation and Functionality. *J. Am Oil Chem Soc*. 2003, 80, 319-326.

Wu, Serena. (2020). Phospholipid Induced Polyphenol Precipitation and Its Potential Reaction Mechanism. Department of Food Science, University of Wisconsin—Madison.

Yang, R., Lin, S., Kuo, G. Content and distribution of flavonoids among 91 edible plant species. *Asia Pac. J. Clin. Nutr*. 2008, 17, 275-279.

Yoshioka, H., Haga, H., Kubota, M., Sakai, Y. Interaction of (+)-Catechin with a Lipid Bilayer Studied by the Spin Probe Method. *Biosci. Biotechnol. Biochem*. 2006, 70, 395-400.

Yu, X., Chu, S., Hagerman, A. E., Lorigan, G. A. Probing the interaction of polyphenols with lipid bilayers by solid-state NMR Spectroscopy. *J. Agric. Food Chem*. 2011, 59, 6783-6789.

Zhang, L., Zhang, X., Cheng, M., Cao, J., Wu, Z., Weng, P., Yan, M. Oolong Tea Polyphenols-Phospholipids Complex Reduces Obesity in High Fat Diet-Induced Mice Model. *European Hournal of Lipid Science and Technology*. 2017, 119, 1600394.

Ziaei, S., Halaby, R. Dietary Isoflavones and Breast Cancer Risk. *Medicines*. 2017, 4, 18-28.

Złotek, U., Mikulska, S., Nagajek, M., Świeca, M. The effect of different solvents and number of extraction steps on the polyphenol content and antioxidant capacity of basil leaves (*Ocimum basilicum* L.) extracts. *Saudi Journal of Biological Sciences*. 2016, 23, 628-633.

https://chemaxon.com.

Phenolic Acids

Flavonoids

Proanthocyanidin $R_1=R_2=OH, R_3=H$ : Protocatechuic acid
$R_1=R_2=R_3=OH$ : Gallic acid $R_1=OH$ : Coumaric acid
$R_1=R_2=OH$ : Caffeic acid
$R_1=OCH_3, R_2=OH$ : Ferulic acid Chlorogenic acid (a)

(b)

Resveratrol

Gallic acid

Anthocyanin (basic)

Genistein

Rutin

Quercetin-3-galactoside (+)-Catechin

Quercetin

US 11,548,845 B2

METHODS OF ISOLATING PHENOLS FROM PHENOL-CONTAINING MEDIA

STATEMENT REGARDING FEDERALLY SPONSORED RESEARCH

This invention was made with government support under 2016-67017-24428 awarded by the USDA/NIFA. The government has certain rights in the invention.

FIELD OF THE INVENTION

The invention is generally directed to methods of isolating phenols and other compounds from phenol-containing compositions.

BACKGROUND

Many naturally occurring phenols, particularly polyphenols, are useful as dyes, colorants, pigments, pigment stabilizers, and ingredients in foods, dietary supplements, and cosmetics, among other uses. Simple, efficient methods for isolating phenols from phenol-containing media are needed.

SUMMARY OF THE INVENTION

The present invention provides methods for isolating phenols from phenol-containing media. An exemplary method includes combining a phospholipid-containing composition such as lecithin with a phenol-containing medium such as a fruit or vegetable juice to generate a combined medium, incubating the combined medium to precipitate phenols in the combined medium and thereby form a phenol precipitate phase and a phenol-depleted phase, and separating the phenol precipitate phase and the phenol-depleted phase. A schema of an exemplary version of the invention is shown in FIG. 1.

The methods can further include extracting phenols from the separated phenol precipitate phase. The extracting can include mixing the separated phenol precipitate phase with an extraction solvent to solubilize in the extraction solvent at least a portion of the phenols originally present in the phenol precipitate phase.

The invention also provides a phenol isolate generated from the methods described herein, wherein the phenol isolate comprises the separated phenol precipitate phase, the phenol solubilized in the extraction solvent, or phenol separated from the extraction solvent.

The objects and advantages of the invention will appear more fully from the following detailed description of the preferred embodiment of the invention made in conjunction with the accompanying drawings.

DETAILED DESCRIPTION OF THE INVENTION

Figure 1:
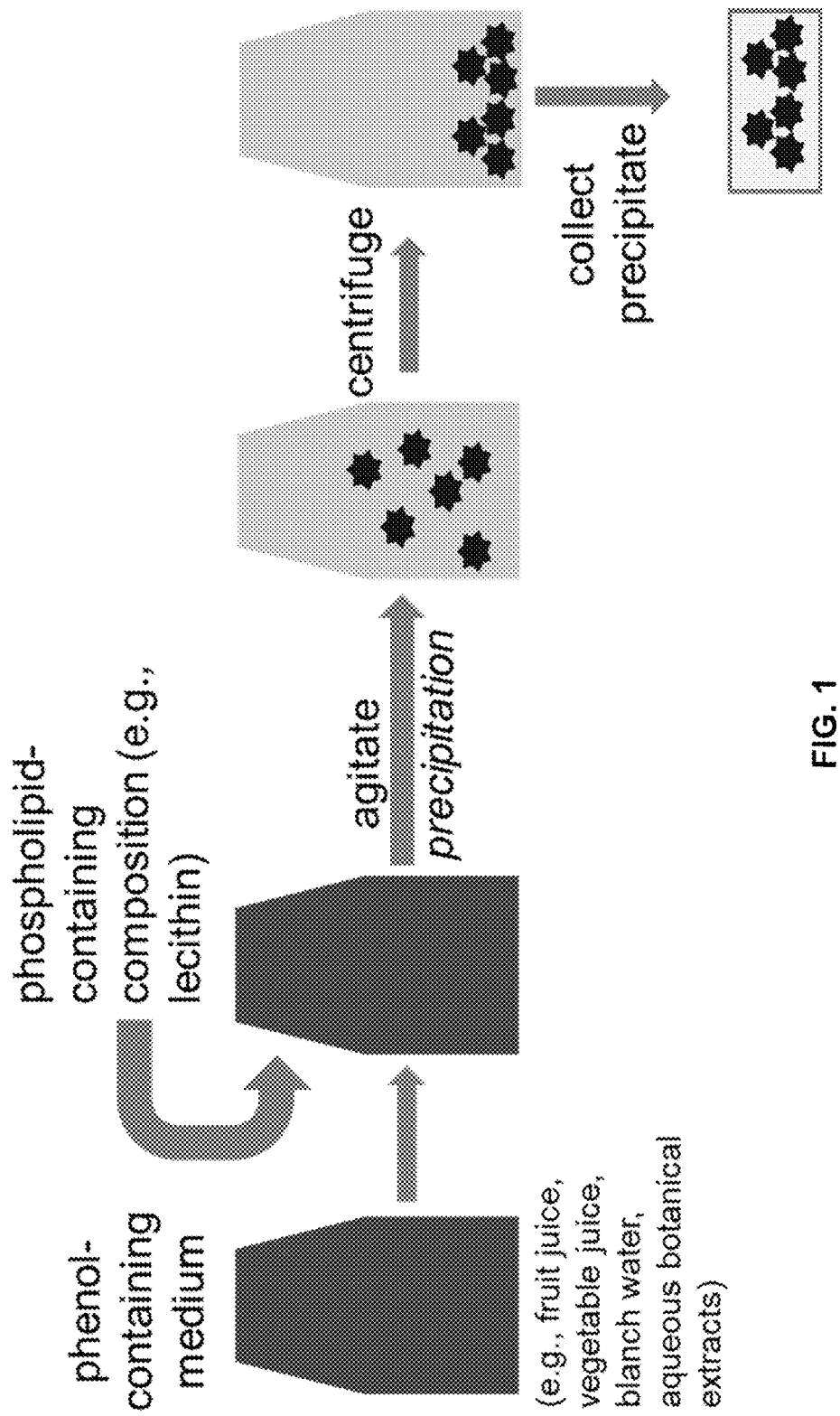
FIG. 1. Schema of an exemplary version of the invention.

The invention provides methods of isolating phenols from a phenol-containing medium. Preferred methods comprise combining a phospholipid-containing composition with the phenol-containing medium to generate a combined medium, incubating the combined medium to precipitate phenols in the combined medium and thereby form a phenol precipitate phase and a phenol-depleted phase, and separating the phenol precipitate phase and the phenol-depleted phase. The term "depleted" in the phrase "phenol-depleted phase" encompasses a partial or complete depletion of phenol refers to a reduced amount of phenol by percent weight in the phenol-depleted phase compared to the amount of phenol by percent weight in phenol-containing medium, and can imply a partial or complete depletion of phenol in the phenol-depleted phase.

The phospholipid-containing composition includes any composition containing a phospholipid. The phospholipid-containing composition can contain pure phospholipid (100% w/w phospholipid) or can contain phospholipid with a carrier and/or other active components. The phospholipid-containing composition is preferably provided in a solid, semi-solid, or liquid state. Exemplary solid forms include powders and granules. Exemplary semi-solid forms include gels and pastes.

Phospholipids are well known in the art and include compounds comprising one or two hydrophobic tails connected to a phosphate group via glycerol or sphingosine moiety. The phosphate group can be modified with various groups. The phosphate group and any moieties other than the hydrophobic tails attached to it are often referred to as the "head." Such groups can include amine-containing groups such as choline and ethanolamine, amino acids such as serine, and/or sugars such as inositol. The hydrophobic tails can include unsubstituted or substituted hydrocarbon chains. The hydrocarbon chains can have a range of carbon lengths, can be saturated or unsaturated, and can be substituted with hydroxyl groups, halogens (bromine, etc.), sulfonates, or other substituents. Lysophospholipids are phospholipids comprising only one hydrocarbon chain rather than two and are encompassed by the term "phospholipid" as used herein. General classes of phospholipids include glycerophospholipids, which connect the hydrophobic tail(s) to the phosphate group via a glycerol moiety, and phosphosphingolipids, which connect the hydrophobic tail(s) to the phosphate group via a sphingosine moiety. General classes of glycerophospholipids include phosphatidates, in which the hydrocarbon chains are attached to the glycerol moiety via ester linkages, and plasmalogens, in which a hydrocarbon chain is attached to the glycerol moiety via an ether rather than an ester linkage. Exemplary phospholipids include phosphatidic acid (PA), phosphatidylethanolamine (PE), phosphatidylcholine (PC), phosphatidylserine (PS), phosphatidylinositol (PI), phosphatidylinositol phosphate (PIP, also known as phosphatidylinositol monophosphate: e.g., phosphatidylinositol 3-phosphate, also known as PtdIns3P or PI(3)P; phosphatidylinositol 4-phosphate, also known as PtdIns4P or PI(4)P; phosphatidylinositol 5-phosphate, also known as PtdIns5P or PI(5)P)), phosphatidylinositol bisphosphate (PIP2: phosphatidylinositol 3,4-bisphosphate, also known as PtdIns(3,4)$P_2$ or PI(3,4)$P_2$; phosphatidylinositol 3,5-bisphosphate, also known as PtdIns(3,5)$P_2$ or PI(3,5)$P_2$; phosphatidylinositol 4,5-bisphosphate, also known as PtdIns(4,5)$P_2$, PI(4,5)$P_2$ or often simply referred to as $PIP_2$), and phosphatidylinositol trisphosphate (PIP3, phosphatidylinositol 3,4,5-trisphosphate, also known as PtdIns(3,4,5) $P_3$ or PI(3,4,5)$P_3$), ceramides, sphingomyelins, and glycosphingolipids such as cerebrosides and gangliosides. All phospholipids based on phosphatidylinositol (e.g., phosphatidylinositol (PI), phosphatidylinositol phosphate (PIP), phosphatidylinositol bisphosphate (PIP2), and phosphatidylinositol trisphosphate (PIP3)) are known as inositides, or sometimes phosphoinositides.

In some versions of the invention, the phospholipid-containing composition comprises one or more of phosphatidylcholine, phosphoinositide, phosphatidylethanolamine, phosphatidylserine, and phosphatidic acid, such as one or more of phosphatidylcholine, phosphoinositide, and phosphatidylethanolamine or each of phosphatidylcholine, phosphoinositide, and phosphatidylethanolamine. The phosphoinositide in each case can comprise phosphatidylinositol.

In some versions, the phospholipid-containing composition comprises hydroxylated phospholipids. Hydroxylated phospholipids are phospholipids with hydroxyl substitutions on the hydrocarbon chains. Hydroxylated phospholipids can be made, for example, by treating phospholipids with hydrogen peroxide and an organic acid such as acetic or lactic acid (F. D. Gunstone; John L. Harwood; Albert J. Dijkstra (2007). The Lipid Handbook. Boca Raton, Fla.: CRC Press. pp. 319-320.).

The phospholipid-containing composition in some versions includes phospholipid in an amount of at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w, at least about 99% w/w, or about 100% w/w of the phospholipid-containing composition. The phospholipid-containing composition in some versions includes phospholipid in an amount less than about 10% w/w, less than about 15% w/w, less than about 20% w/w, less than about 25% w/w, less than about 30% w/w, less than about 35% w/w, less than about 40% w/w, less than about 45% w/w, less than about 50% w/w, less than about 55% w/w, less than about 60% w/w, less than about 65% w/w, less than about 70% w/w, less than about 75% w/w, less than about 80% w/w, less than about 85% w/w, less than about 90% w/w, less than about 95% w/w, less than about 99% w/w, or less than about 100% w/w of the phospholipid-containing composition.

The phospholipid-containing composition in some versions includes negatively charged phospholipid in an amount of at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w, at least about 99% w/w, or about 100% w/w of the phospholipid-containing composition. The phospholipid-containing composition in some versions includes negatively charged phospholipid in an amount less than about 10% w/w, less than about 15% w/w, less than about 20% w/w, less than about 25% w/w, less than about 30% w/w, less than about 35% w/w, less than about 40% w/w, less than about 45% w/w, less than about 50% w/w, less than about 55% w/w, less than about 60% w/w, less than about 65% w/w, less than about 70% w/w, less than about 75% w/w, less than about 80% w/w, less than about 85% w/w, less than about 90% w/w, less than about 95% w/w, less than about 99% w/w, or less than about 100% w/w of the phospholipid-containing composition. "Negatively charged phospholipid" refers to phospholipids with a head carrying a net-negative charge. Exemplary negatively charged phospholipids include phosphatidylserine (PS), phosphatidic acid (PA), phosphatidylglycerol (PG) cardiolipin (CL), and phosphoinositides. The negatively charged phospholipid in the phospholipid-containing composition can comprise or consist of phosphatidylserine (PS), phosphatidic acid (PA) (including salts thereof), ammonium phosphatides (see, e.g., Norn, *Emulsifiers in Food Technology*, Second Edition. Ed. Viggo Norn, 2015, John Wiley & Sons, Ltd., Chapter 3, "Ammonium Phosphatides," pp. 61-72), phosphatidylglycerol (PG) cardiolipin (CL), any phosphoinositide described herein or known in the art, and any lysophospholipid forms thereof.

The phospholipid-containing composition in some versions includes phosphoinositide in an amount of at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w, at least about 99% w/w, or about 100% w/w of the phospholipid-containing composition. The phospholipid-containing composition in some versions includes phosphoinositide in an amount less than about 10% w/w, less than about 15% w/w, less than about 20% w/w, less than about 25% w/w, less than about 30% w/w, less than about 35% w/w, less than about 40% w/w, less than about 45% w/w, less than about 50% w/w, less than about 55% w/w, less than about 60% w/w, less than about 65% w/w, less than about 70% w/w, less than about 75% w/w, less than about 80% w/w, less than about 85% w/w, less than about 90% w/w, less than about 95% w/w, less than about 99% w/w, or less than about 100% w/w of the phospholipid-containing composition. Exemplary phosphoinositides are described elsewhere herein and include phosphatidylinositols (PIs), phosphatidylinositol phosphates (PIPs), phosphatidylinositol bisphosphates (PIP2s), and phosphatidylinositol trisphosphates (PIP3s) The phosphoinositide in the phospholipid-containing composition can comprise or consist of any phosphoinositide described herein or known in the art.

The phospholipid-containing composition in some versions includes hydroxylated phospholipid in an amount of at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w, at least about 99% w/w, or about 100% w/w of the phospholipid-containing composition. The phospholipid-containing composition in some versions includes hydroxylated phospholipid in an amount less than about 10% w/w, less than about 15% w/w, less than about 20% w/w, less than about 25% w/w, less than about 30% w/w, less than about 35% w/w, less than about 40% w/w, less than about 45% w/w, less than about 50% w/w, less than about 55% w/w, less than about 60% w/w, less than about 65% w/w, less than about 70% w/w, less than about 75% w/w, less than about 80% w/w, less than about 85% w/w, less than about 90% w/w, less than about 95% w/w, less than about 99% w/w, or less than about 100% w/w of the phospholipid-containing composition.

In addition to the phospholipid, the phospholipid-containing composition can include a number of non-phospholipid components. Exemplary non-phospholipid components may comprise triglycerides, sterols, glycolipids, and free carbohydrates. Accordingly, the non-phospholipid components may comprise any one or more of triglycerides, sterols, glycolipids, and free carbohydrates in any combination. In some versions, the amount of the non-phospholipid components in the phospholipid-containing composition is at least about 1% w/w, at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, or at least about 80% w/w of the phospholipid-containing composition. In some versions, the amount of the non-phospholipid components in the phospholipid-containing composition is less than about 1% w/w, less than about 5% w/w, less than about 10% w/w, less than about 15% w/w, less than about 20% w/w, less than about 25% w/w, less than about 30% w/w, less than about 35% w/w, less than about 40% w/w, less than about 45% w/w, less than about 50% w/w less than about 55% w/w, less than about 60% w/w, less than about 65% w/w, less than about 70% w/w, less than about 75% w/w, or less than about 80% w/w of the phospholipid-containing composition.

In some versions, the phospholipid-containing composition comprises lecithin. Lecithins are mixed phospholipid compositions that are well-known in the art. See Bueschelberger et al., Emulsifiers in Food Technology, Second Edition. Ed. Viggo Norn., 2015, John Wiley & Sons, Ltd., Chapter 2, "Lecithins," pp. 21-60. Lecithin compositions typically contain mixtures of phosphatidylcholine, phosphatidylinositol, phosphatidylethanolamine, phosphatidylserine, and phosphatidic acid, but can be devoid of one or more of these phospholipids and can also contain additional components such as triglycerides, glycolipids, sterols, and free carbohydrates, among other components. An exemplary composition of soy lecithin is (by mass): 33-35% soybean oil, 20-21% phosphatidylinositols, 19-21% phosphatidylcholine, 8-20% phosphatidylethanolamine, 5-11% other phosphatides, 5% free carbohydrates, 2-5% sterols, and 1% moisture (Scholfield, C. R. (October 1981). "Composition of Soybean Lecithin". *Journal of the American Oil Chemists' Society*. 58 (10): 889-892). Other exemplary lecithin compositions are found in Bueschelberger et al., 2015. Common sources of lecithin include soybeans, egg yolk, milk, marine sources, rapeseed, cottonseed, sunflower oil, fish eggs, fish roe, and chicken and sheep brain. Lecithin can be extracted chemically from these and other sources using solvents such as hexane, ethanol, acetone, petroleum ether or benzene or can be extracted mechanically.

In some versions, the lecithin in the phospholipid-containing composition comprises chemically modified lecithin. Chemically modified lecithin is lecithin that is or has been subjected to a chemical treatment that modifies the chemical structure of any one or more of its components. Chemically modified lecithin can include hydrolyzed lecithin, hydroxylated lecithin, acetylated lecithin, hydrogenated lecithin, halogenated lecithin, among other examples, and is encompassed by the general term "lecithin" as used herein. The lecithin can be a powdered and/or de-oiled lecithin, which are also encompassed by the general term "lecithin" as used herein.

In some versions, hydroxylated lecithin is used in or as the phospholipid-containing composition. Hydroxylated lecithin comprises phospholipids with hydroxyl substitutions on the hydrocarbon chains. Hydroxylated lecithin can be made, for example, by treating lecithin with hydrogen peroxide and an organic acid such as acetic or lactic acid (F. D. Gunstone; John L. Harwood; Albert J. Dijkstra (2007). The Lipid Handbook. Boca Raton, Fla.: CRC Press. pp. 319-320.).

In some versions, the lecithin is enriched or spiked with a negatively charged phospholipid, such as an inositide.

As outlined in the following examples, phospholipids and phospholipid-containing compositions having higher hydrophilic-lipophilic balance (HLB) values are more effective at precipitating phenols in phenol-containing media. Accordingly, in some versions, the phospholipid-containing composition has an HLB greater than about 3, greater than about 4, greater than about 5, greater than about 6, greater than about 7, greater than about 8, greater than about 9, greater than about 10, greater than about 11, greater than about 12, greater than about 13, greater than about 14, greater than about 15, greater than about 16, greater than about 17, greater than about 18, greater than about 19, greater than about 20, greater than about 21, greater than about 22, greater than about 23, greater than about 24, greater than about 25, greater than about 26, greater than about 27, or greater than about 28. Additionally or alternatively, the phospholipid-containing composition in some versions optionally has an HLB less than 28, less than 27, less than 26, less than 25, less than 24, less than 23, less than 22, less than 21, less than 20, less than 19, less than 18, less than 17, less than 16, less than 15, less than 14, less than 13, less than 12, less than 11, or less than 10. Exemplary HLB ranges for the phospholipid-containing composition include 4-37, 7-35, 10-32, 17-37, 22-32, 4-12, 7-11, and 8-10.

The HLB scale ranks the tendency of a surfactant (such as the phospholipids of the invention) or a compositional mixture containing such a surfactant to be hydrophilic or hydrophobic (lipophilic). The HLB of a single non-ionic surfactant can be determined by the method of Griffin (Griffin, William C. (1954), "Calculation of HLB Values of Non-Ionic Surfactants" (PDF), Journal of the Society of Cosmetic Chemists, 5 (4): 249-56), which employs the following equation:

$$HLB=20*M_h/M,$$

where $M_h$ is the molecular mass of the hydrophilic portion of the molecule, and M is the molecular mass of the whole molecule. A single HLB value for an ionic surfactant can also be estimated by method of Davies (Davies, J. T. (1957), "A Quantitative Kinetic Theory of Emulsion Type. I. Physical Chemistry of the Emulsifying Agent", Gas/Liquid and Liquid/Liquid Interfaces. Proceedings of $2^{nd}$ International Congress Surface Activity, 1: 426-438) by the following equation:

$$HLB=\Sigma(\text{hydrophilic group numbers})-n(\text{group number per } CH_2 \text{ group})+7$$

where hydrophilic group numbers are from 0.33-38.7 and $CH_2$ group numbers=0.475. See also Becher, P. (2001) *Emulsions: theory and Practice*, $3^{rd}$ edn., American Chemical Society, Washington, D.C. The HLB of a mixture of surfactants can be determined by multiplying the concentration of each surfactant by its HLB, taking the sum of these numbers, and dividing the sum by the total concentration of surfactant. HLB calculators for performing this calculation are widely available in the art. See, e.g., https://chemaxon.com.

The formulas given above are satisfactory for most surfactants. Some ionic surfactants, non-ionic surfactants, and mixtures of surfactants do not follow this "weight percentage" HLB basis. The HLB of any surfactant or mixture thereof can alternatively be determined experimentally. A number of methods for experimentally determining HLB are known in the art. One method involves "aligning" a surfactant or surfactant mixture with unknown HLB with common nonionic surfactants of known HLB based on emulsification properties. Another method involves emulsifying oils of known "required HLBs"; the oil in which the surfactant or surfactant mixture emulsifies best indicates the HLB Another method determines HLB according to solubility or dispersibility characteristics of the surfactant or surfactant mixture in water as shown in Table 1.

TABLE 1

| HLB by Dispersibility | |
|---|---|
| Effect | HLB |
| No dispersibility in water | 1-4 |
| Poor dispersion | 3-6 |
| Milky dispersion after vigorous agitation | 6-8 |
| Stable milky dispersion | 8-10 |
| Stable milky dispersion | 10-13 |
| Clear solution | 13+ |

In some versions of the invention, the phospholipid-containing composition is combined with the phenol-containing medium in an amount of at least about 0.01% w/v, at least about 0.05% w/v, at least about 0.1% w/v, at least about 0.5% w/v, at least about 1% w/v, at least about 1.5% w/v, at least about 2% w/v, at least about 2.5% w/v, at least about 3% w/v, at least about 3.5% w/v, at least about 4% w/v, at least about 4.5% w/v, or at least about 5% w/v of the phenol-containing medium. In some versions of the invention, the phospholipid-containing composition is combined with the phenol-containing medium in an amount less than about 2% w/v, less than about 2.5% w/v, less than about 3% w/v, less than about 3.5% w/v, less than about 4% w/v, less than about 4.5% w/v, less than about 5% w/v, less than about 7.5% w/v, less than about 10% w/v, less than about 15% w/v, less than about 20% w/v, less than about 25% w/v, less than about 30% w/v, less than about 40% w/v, less than about 50% w/v, less than about 60% w/v, or less than about 70% w/v of the phenol-containing medium.

In some versions of the invention, the phospholipid-containing composition is combined with the phenol-containing medium in an amount of at least about 0.01% w/v, at least about 0.05% w/w, at least about 0.1% w/w, at least about 0.5% w/w, at least about 1% w/w, at least about 1.5% w/w, at least about 2% w/w, at least about 2.5% w/w, at least about 3% w/w, at least about 3.5% w/w, at least about 4% w/w, at least about 4.5% w/w, or at least about 5% w/w of the phenol-containing medium. In some versions of the invention, the phospholipid-containing composition is combined with the phenol-containing medium in an amount less than about 2% w/w, less than about 2.5% w/w, less than about 3% w/w, less than about 3.5% w/w, less than about 4% w/w, less than about 4.5% w/w, less than about 5% w/w, less than about 7.5% w/w, less than about 10% w/w, less than about 15% w/w, less than about 20% w/w, less than about 25% w/w, less than about 30% w/w, less than about 40% w/w, less than about 50% w/w, less than about 60% w/w, or less than about 70% w/w of the phenol-containing medium.

In some versions of the invention, the phenol-containing medium is an aqueous medium. The term "aqueous medium" is used herein to refer to a medium containing at least 70% v/v water.

In some versions of the invention, the phenol-containing medium is a medium containing water in an amount of at least about 40% v/v, at least about 45% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, or at least about 99% v/v of the phenol-containing medium.

The phenol-containing medium can contain various amounts of solvents other than water. The non-water solvents can include organic solvents. The non-water solvents can include alcohols such as methanol, ethanol, propanol, or others. The non-water solvent in some versions is present in the phenol-containing medium in an amount of at least about 1% v/v, at least about 5% v/v, at least about 10% v/v, at least about 15% v/v, at least about 20% v/v, at least about 25% v/v, or at least about 30% v/v of the phenol-containing medium. The non-water solvent in some versions is present in the phenol-containing medium in an amount less than 1% v/v, less than 5% v/v, less than 10% v/v, less than 15% v/v, less than 20% v/v, less than 25% v/v, or less than 30% v/v of the phenol-containing medium.

In some versions of the invention, the phenol-containing medium is a liquid. In some versions of the invention, the phenol-containing medium is a semi-solid, such as a gel. The phenol-containing medium can comprise any medium containing phenols.

Preferred media include media derived from plants or plant matter. Exemplary media derived from plants or plant matter include fruit juice, vegetable juice, blanch water, and botanical extracts. Such media can be in a concentrated, diluted, or non-concentrated/non-diluted form. For the purposes of the present invention, media such as coffee and tea are considered botanical extracts. Exemplary fruit and vegetable juices are provided in the following examples.

The methods of the invention are capable of precipitating and, ultimately, isolating phenols from phenol-containing media. Examples of phenols that can be precipitated and isolated include polyphenols. Examples of polyphenols that can be precipitated and isolated include flavonoids. Examples of flavonoids that can be precipitated and isolated include anthocyanins, anthocyanidins, flavan-3-ols, and proanthocyanidins. Examples of polyphenols that can be precipitated and isolated also include tannins. Examples of tannins that can be precipitated and isolated include hydrolysable tannins, phlorotannins, condensed tannins, phlobatannins, and monomers thereof. Accordingly, the phenol-containing medium, the combined medium, and/or the phenol precipitate phase can include any of the above-mentioned phenols in any combination.

By virtue of isolating phenols from the phenol-containing medium, the methods of the invention are capable of reducing the mass concentration of any phenol described herein. As used herein, "mass concentration" refers to the concentration of a component in w/v.

In some versions, the total phenol mass concentration in the phenol-depleted phase is at least about 10% less, at least about 15% less, at least about 20% less, at least about 25% less, at least about 30% less, at least about 35% less, at least about 40% less, at least about 45% less, at least about 50% less, at least about 55% less, at least about 60% less, at least about 65% less, at least about 70% less, at least about 75% less, at least about 80% less, at least about 85% less, at least about 90% less, or at least about 95% less than the total phenol mass concentration in the phenol-containing medium. In some versions, the total phenol mass concentration in the phenol-depleted phase is up to about 75% less, up to about 80% less, up to about 85% less, up to about 90% less, up to about 95% less, or up to about 99% less than the total phenol mass concentration in the phenol-containing medium. Methods of determining total phenol mass concentration are provided in the following examples, wherein the total phenol mass concentration can be expressed as equivalents to mass of gallic acid per mL.

In some versions, the monomeric anthocyanin mass concentration in the phenol-depleted phase is at least about 10% less, at least about 15% less, at least about 20% less, at least about 25% less, at least about 30% less, at least about 35% less, at least about 40% less, at least about 45% less, at least about 50% less, at least about 55% less, at least about 60% less, at least about 65% less, at least about 70% less, at least about 75% less, at least about 80% less, at least about 85% less, at least about 90% less, or at least about 95% less than the monomeric anthocyanin mass concentration in the phenol-containing medium. In some versions, the monomeric anthocyanin mass concentration in the phenol-depleted phase is up to about 75% less, up to about 80% less, up to about 85% less, up to about 90% less, up to about 95% less, or up to about 99% less than the monomeric anthocyanin mass concentration in the phenol-containing medium. Methods of determining monomeric anthocyanin mass concentration are provided in the following examples.

In some versions, the proanthocyanidin mass concentration in the phenol-depleted phase is at least about 10% less, at least about 15% less, at least about 20% less, at least about 25% less, at least about 30% less, at least about 35% less, at least about 40% less, at least about 45% less, at least about 50% less, at least about 55% less, at least about 60% less, at least about 65% less, at least about 70% less, at least about 75% less, at least about 80% less, at least about 85% less, at least about 90% less, or at least about 95% less than the proanthocyanidin mass concentration in the phenol-containing medium. In some versions, the proanthocyanidin mass concentration in the phenol-depleted phase is up to about 75% less, up to about 80% less, up to about 85% less, up to about 90% less, up to about 95% less, or up to about 99% less than the proanthocyanidin mass concentration in the phenol-containing medium. Methods of determining proanthocyanidin mass concentration are provided in the following examples, wherein the proanthocyanidin mass concentration can be expressed as equivalents to mass of catechin per mL.

The term "separating" used herein at least with reference to separating the phenol precipitate phase and the phenol-depleted phase refers to physical separation such that at least one physical medium other than the phenol precipitate phase and the phenol-depleted phase is disposed between at least a substantial portion of the phenol precipitate phase and a substantial portion of the phenol-depleted phase. "Substantial portion" refers to an amount of at least 5% by weight of a given phase. The physical medium disposed between the respective media can be any medium that is not the phenol precipitate phase and the phenol-depleted phase. Exemplary media include a gas such as air, nitrogen, etc.; a solid such as plastic or glass, or a liquid medium in which the phenol precipitate phase and the phenol-depleted phase are generally insoluble. In some versions, the phenol precipitate phase and the phenol-depleted phase are separated to an extent that at least one physical medium other than the phenol precipitate phase and the phenol-depleted phase is disposed between at least about 10% by weight, at least about 20% by weight, at least about 30% by weight, at least about 40% by weight, at least about 50% by weight, at least about 60% by weight, at least about 70% by weight, at least about 80% by weight, at least about 90% by weight, at least about 95% by weight, or at least about 99% by weight of the phenol precipitate phase and at least about 90% by weight of the phenol-depleted phase. In some versions, the phenol precipitate phase and the phenol-depleted phase are separated to an extent that at least one physical medium other than the phenol precipitate phase and the phenol-depleted phase is disposed between at least about 10% by weight, at least about 20% by weight, at least about 30% by weight, at least about 40% by weight, at least about 50% by weight, at least about 60% by weight, at least about 70% by weight, at least about 80% by weight, at least about 90% by weight, at least about 95% by weight, or at least about 99% by weight of the phenol-depleted phase and at least about 90% by weight of the phenol precipitate phase.

The phenol precipitate phase and the phenol-depleted phase as described herein are substantially immiscible in each other. In exemplary versions, the phenol precipitate phase is a solid phase, and the phenol-depleted phase is a liquid phase.

The separating can be performed using any method known in the art used to separate two immiscible substances, such as solid precipitate in a liquid. One example includes centrifugation to consolidate the phases and decanting or suctioning one phase from the other. In such a method the phenol precipitate phase would form a pellet, and the phenol-depleted phase could then be decanted or suctioned from the pellet. Another example includes filtering one phase from the other. In such a method, the phenol precipitate phase could be filtered as a retentate from the phenol-depleted phase. Accordingly, the separating step may comprise one or more of centrifuging the phenol precipitate phase and the phenol-depleted phase to pellet the phenol precipitate phase, decanting or aspirating the phenol-depleted phase from the phenol precipitate phase, and filtering the phenol precipitate phase from the phenol-depleted phase.

In some versions of the invention, a further step of mixing the phospholipid-containing composition and the phenol-containing medium is performed between the combining and the separating steps. The mixing can be performed by vortexing, stirring, shaking, swirling, or other methods. The term "mixing" refers to an active step performed or initiated by human intervention to integrate the phospholipid-containing composition and the phenol-containing medium together. Mere diffusion unaided by human intervention after the initial combination does not constitute "mixing" as used herein.

The separated phenol precipitate phase can comprise phospholipid and phenols in an amount by weight of at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 99%.

As shown in the examples, phenol precipitation and depletion are aided by lower temperatures. Thus, in some versions of the invention, the incubating is performed at a temperature less than about 25° C., less than about 20° C., less than about 17° C., less than about 15° C., less than about 10° C., or less than about 5° C. Although it is possible to freeze-thaw the combined medium before the separating step, it is preferred for efficiency purposes not to freeze the combined medium. Accordingly, the incubating step is preferably performed at a temperature greater than the freezing point of the combined medium. In some versions, such as when the combined medium is comprised mostly of water, the incubating step is preferably performed at a temperature greater than about 0° C.

In some versions, the phenol-containing medium has a sugar content of less than about 50° Brix, less than about 40° Brix, less than about 30° Brix, less than about 20° Brix, less than about 15° Brix, or less than about 10° Brix. Methods for determining degrees Brix are well known in the art.

As shown in the examples, addition of pectin with the phospholipid-containing composition and the phenol-containing medium enhances phenol depletion from the phenol containing medium. Accordingly, in some versions of the invention, pectin is combined with the phospholipid-containing composition and the phenol-containing medium to generate the combined medium. The pectin is preferably combined with the phospholipid-containing composition and the phenol-containing medium in an amount effective to increase precipitation of the phenols in the combined medium compared to precipitation in an otherwise identical medium lacking the pectin. In some versions, pectin is combined with the phospholipid-containing composition and the phenol-containing medium in an amount of at least about 0.001% w/v, at least about 0.003% w/v, at least about 0.01% w/v, at least about 0.03% w/v, at least about 0.1% w/v, at least about 0.3% w/v, at least about 1% w/v, at least about 3% w/v, or at least about 10% w/v of the combined medium and up to about 3% w/v, about 5% w/v, about 7% w/v, about 10% w/v, or about 15% w/v of the combined medium.

The methods of the invention can further include a step of extracting phenols from the separated phenol precipitate phase. The extracting can comprises mixing the separated phenol precipitate phase with an extraction solvent to solubilize in the extraction solvent at least a portion of the phenols originally present in the phenol precipitate phase. "Extraction solvent" refers to any solvent in which phenols, such as the polyphenols described herein, are soluble. In preferred versions, the separated phenol precipitate phase comprises phenols and phospholipid, and mixing the separated phenol precipitate phase with the extraction solvent preferentially solubilizes the phenols over the phospholipid in the extraction solvent. "Preferentially solubilizes" in this context means that the ratio of phenols to phospholipid in the extraction solvent after mixing with the separated phenol precipitate phase is greater than the ratio of phenols to phospholipid in the phenol precipitate phase prior to mixing with the extraction solvent. Accordingly, extraction solvents in which phenols have a higher solubility than phospholipid (including in such forms as lecithin) are preferred.

In some versions, the extraction solvent comprises an organic solvent. Exemplary organic solvents include ethanol, acetone, methanol, tetrachloroethylene, toluene, methyl acetate, ethyl acetate, hexane, benzene, and dimethylsulfoxide, among others. In some versions, the extraction solvent can include acidic water. "Acidic water," refers to water having a pH less than 5, such as less than 4, less than 3, less than 2, or less than 1.

In some versions, the extraction solvent comprises an alcohol, such as ethanol. The extraction solvent can comprise the alcohol in an amount of at least about at least about 5% v/v, at least about 10% v/v, at least about 15% v/v, at least about 20% v/v, at least about 25% v/v, at least about 30% v/v, at least about 35% v/v, at least about 40% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, at least about 96% v/v, at least about 97 v/v, at least about 98 v/v, or at least about 99% v/v.

In some versions, the extraction solvent comprises acetone. The extraction solvent can comprise the acetone in an amount of at least about at least about 5% v/v, at least about 10% v/v, at least about 15% v/v, at least about 20% v/v, at least about 25% v/v, at least about 30% v/v, at least about 35% v/v, at least about 40% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, at least about 96% v/v, at least about 97 v/v, at least about 98 v/v, or at least about 99% v/v.

In some versions, the extraction solvent comprises an alcohol, such as ethanol, and acetone in a combined amount of at least about 25% v/v, at least about 30% v/v, at least about 35% v/v, at least about 40% v/v, at least about 50% v/v, at least about 55% v/v, at least about 60% v/v, at least about 65% v/v, at least about 70% v/v, at least about 75% v/v, at least about 80% v/v, at least about 85% v/v, at least about 90% v/v, at least about 95% v/v, at least about 96% v/v, at least about 97 v/v, at least about 98 v/v, or at least about 99% v/v.

In some versions, the extraction solvent comprises water in an amount less than about 80% v/v, less than about 75% v/v, less than about 70% v/v, less than about 65% v/v, less than about 60% v/v, less than about 55% v/v, less than about 50% v/v, less than about 45% v/v, less than about 40% v/v, less than about 35% v/v, less than about 30% v/v, less than about 25% v/v, less than about 20% v/v, less than about 15% v/v, less than about 10% v/v, less than about 5% v/v, less than about 4% v/v, less than about 3% v/v, less than about 2% v/v, or less than about 1% v/v, or is completely devoid of water.

In some versions, at least about 5% w/w, at least about 10% w/w, at least about 15% w/w, at least about 20% w/w, at least about 25% w/w, at least about 30% w/w, at least about 40% w/w, or at least about 50% w/w of the total phenols originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the total phenols originally present in the phenol-containing medium is solubilized in the extraction solvent.

In some versions, at least about 5% w/w, at least about 10% w/w, at least about 15% w/w, at least about 20% w/w, at least about 25% w/w, at least about 30% w/w, at least about 40% w/w, or at least about 50% w/w of the polyphenols originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the polyphenols originally present in the phenol-containing medium is solubilized in the extraction solvent.

In some versions, at least about 5% w/w, at least about 10% w/w, at least about 15% w/w, at least about 20% w/w, at least about 25% w/w, at least about 30% w/w, at least about 40% w/w, or at least about 50% w/w of the anthocyanins originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the anthocyanins originally present in the phenol-containing medium is solubilized in the extraction solvent.

In some versions, at least about 5% w/w, at least about 10% w/w, at least about 15% w/w, at least about 20% w/w, at least about 25% w/w, at least about 30% w/w, at least about 40% w/w, or at least about 50% w/w of the anthocyanidins originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the anthocyanidins originally present in the phenol-containing medium is solubilized in the extraction solvent.

In some versions, at least about 5% w/w, at least about 10% w/w, at least about 15% w/w, at least about 20% w/w, at least about 25% w/w, at least about 30% w/w, at least about 40% w/w, or at least about 50% w/w of the flavonoids originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the flavonoids originally present in the phenol-containing medium is solubilized in the extraction solvent.

In some versions, at least about 5% w/w, at least about 10% w/w, at least about 15% w/w, at least about 20% w/w, at least about 25% w/w, at least about 30% w/w, at least about 40% w/w, or at least about 50% w/w of the proanthocyanidins originally present in the phenol-containing medium and/or up to about 40%, up to about 45%, up to about 50%, up to about 55%, up to about 60%, up to about 65%, up to about 70%, up to about 75%, up to about 80%, up to about 85%, up to about 90%, or up to about 95% of the proanthocyanidins originally present in the phenol-containing medium is solubilized in the extraction solvent.

A further step can include separating at least a portion of the extraction solvent from the phenols solubilized therein. This can be performed by evaporating the extraction solvent from the phenols, among other methods.

The phenols described herein can be or comprise polyphenols.

The reference to any phospholipid or compound herein can encompass both non-salt and salt forms, unless explicitly indicated otherwise.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Overview

Polyphenols are bioactives present in plants and are associated with a number of health benefits. Upon extraction and purification, polyphenols can be used as ingredients or colorants in foods. The examples show a method where phospholipids can extract polyphenols from aqueous systems via precipitation. We show that phospholipid-induced precipitation of polyphenols can be affected by phospholipid type, polyphenol polarity, molecular size, and location of phenolic hydroxyl groups. Soy lecithin and purified phospholipids were added to cranberry juice or other aqueous systems containing polyphenols to induce polyphenol precipitation. Soy lecithin precipitated cranberry juice anthocyanins and tannins. Increased hydrophilic-lipophilic balance (HLB) value of soy lecithin increased precipitation of cranberry juice anthocyanins, up to 73.1±2.2% at 5 w/v lecithin in juice. Furthermore, phosphatidylinositol (PI) was more effective than phosphatidylcholine (PC) or phosphatidylethanolamine (PE) at inducing cranberry juice anthocyanin precipitation. Among purified polyphenols, polarity, molecular size, and geometry of phenolic hydroxyl groups affected the proportional precipitation. The phospholipid-polyphenol interaction was affected by solution pH, ionic strength, sugar content and alcohol content. The phenolic profile of lecithin-induced precipitate from cranberry juice included phenolic acids, anthocyanins, and flavonoids. These data suggest that the phospholipid-polyphenol interaction is affected by 1) the phospholipid head and fatty acid composition; 2) hydrophobic interactions and hydrogen bonding between polyphenols and lecithin; and 3) polyphenol type. In conclusion, these examples show a new strategy to isolate the polyphenols from polyphenol-rich aqueous systems utilizing phospholipids and enhanced the understanding of phospholipid-polyphenol interactions.

LIST OF ABBREVIATIONS

EGC: (−)-epigallocatechin
ECG: (−)-epicatechin gallate
EGCG: (−)-epigallocatechin gallate
DMAC: 4-dimethylaminocinnamaldehyde
DP: degree of polymerization
CSE: conventional solvent extraction
SE: Soxhlet extraction
SLE: solid-liquid extraction
SFE: supercritical fluid extraction
UAE: ultrasound-assisted extraction
MAE: microwave-assisted extraction
PLE: pressurized liquid extraction
PHWE: pressurized hot water extraction
PC: phosphatidylcholine
PI: phosphatidylinositol
LPC: lysophosphatidylcholine
PE: phosphatidylethanolamine
PA: phosphatidic acid
HLB: hydrophile-lipophile balance
O/W: oil-in-water
W/O: water-in-oil
MA: monomeric anthocyanin Example 1: Introduction Overview The increasing demand for healthy and clean-label foods has increased the interest in polyphenols as food ingredients. The most common application of polyphenol extracts is fortification of bioactives in functional foods and beverages. It is estimated that by 2025, the polyphenols market size is expected to reach 2.08 billion globally [1]. The desirable properties of polyphenols include their ability to act as antioxidants in foods and their potential health effects in preventing inflammation, neurodegenerative diseases, coronary heart diseases and cardiovascular diseases [2-6]. Although there are many studies on beneficial effects of polyphenols, their mechanisms are yet to be well understood. Some recent studies have suggested that polyphenols may interact with phospholipid membranes and that the interaction could be the basis of the bioactivities of the polyphenols [7-13].

Limitations to the widespread use of polyphenols in foods are the cost-effective extraction and purification from complex food matrices. Recently, our group found that soy lecithin can be used to extract polyphenols via precipitation from aqueous solutions. The goal of the examples is to show the understanding of how this method can be used for extracting polyphenols. Specifically, the examples show the following:

1. Show how surfactants interact with anthocyanins in cranberry juice. We show that surfactant polarity affects interactions with anthocyanins.
2. Characterize which types of polyphenols are precipitated by lecithin. The interaction between polyphenols with different polarity, molecular size and geometry of phenolic hydroxyl groups furthers the understanding of the mechanism that explains the phospholipid-polyphenol interaction.
3. Identify how solution composition affects phospholipid-polyphenol interaction. We show effects of the polyphenol-phospholipid interaction with pH, alcohol content, ionic strength, and sugar content in the aqueous solutions.
4. Determine the polyphenol profile of a purified polyphenol fraction resulting from the precipitate. Depending on the composition of the extract, we expect that the polyphenol extract could be applied to a variety of food matrix such as bakery goods, chocolate, and beverages, as well as ingredients for dietary supplements.

REFERENCES

[1]. Grand View Research Global Polyphenols Market Analysis by Product, by Application and Region Forecasts to 2025 (2020). Available online at: https://www.grandviewresearch.com/press-release/global-polyphenols-market.
[2]. Vita, J. A. Polyphenols and cardiovascular disease: effects on endothelial and platelet function. Am. J. Clin. Nutr. 2005, 81, 292-297.
[3]. Renaud, S., de Lorgeril, M. Wine, alcohol, platelets, and the French paradox for coronary heart disease. Lancet. 1992, 339, 1523-1526.
[4]. Pietta, R. G. Flavonoids as antioxidants. J. Nat. Prod. 2000, 63, 1035-1042.
[5]. Graf, B. A., Milbury, P. E., Blumberg, J. B. Flavonols, flavones, flavanones, and human health: epidemiological evidence. J. Med. Food. 2005, 8, 281-90.
[6]. Garcia-Lafuente, A., Guillamón, E., Villares, A., Rostagno, M. A., Martinez, J. A. Flavonoids as anti-inflammatory agents: implications in cancer and cardiovascular disease. Inflamm. Res. 2009, 58, 537-552.
[7]. Tsuchiya, H. Structure-dependent membrane interaction of flavonoids associated with their bioactivity. Food Chem. 2010, 120, 1089-1096.
[8]. Brittes, J., Lucio, M., Nunes, C., Lima, J. L. F. C., Reis, S. Effects of resveratrol on membrane biophysical properties: relevance for its pharmacological effects. Chem. Phys. Lipids. 2010. 163, 747-754.
[9]. Phan, H. T. T., Yoda, T., Chahal, B., Morita, M. et al. Structure-dependent interactions of polyphenols with a biomimetic membrane system. Biochimica et Biophysica Acta (BBA)-Membranes. 2014, 1838, 2670-2677.
[10]. Sirk, T. W., Brown, E. F., Sum, A. K., Friedman, M. Molecular dynamics study on the biophysical interactions of seven green tea catechins with lipid bilayers of cell membranes. J. Agric. Food. Chem. 2008, 56, 7750-7758.
[11]. Uekusa, Y., Kamihira, M., Nakayama, T. Dynamic behavior of tea catechins interacting with lipid membranes as determined by NMR spectroscopy. J. Agric. Food Chem. 2007, 55, 9986-9992.
[12]. Kajiya, K., Kumazawa, S., Naito, A., Nakayama, T. Solid-state NMR analysis of the orientation and dynamics of epigallocatechin gallate, a green tea polyphenol, incorporated into lipid bilayers. Magn. Reson. Chem. 2008, 46, 174-177.
[13]. Tamba, Y., Ohba, S., Kubota, M., Yoshioka, H., Yamazaki, M. Single GUV method reveals interaction of tea catechin (−)-epigallocatechin gallate with lipid membranes. Biophys. J. 2007, 92, 3178-3194.

Example 2: Background

Types and Distribution of Polyphenols in Food

Figure 2:
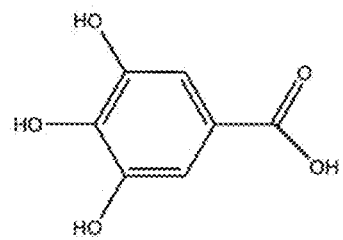
FIG. 2. Representative chemical structures of polyphenols.
Figure 2:
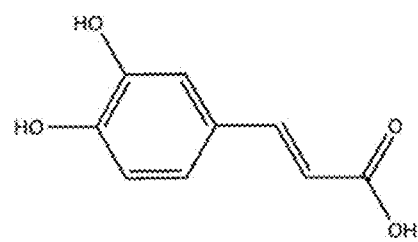
Figure 2:
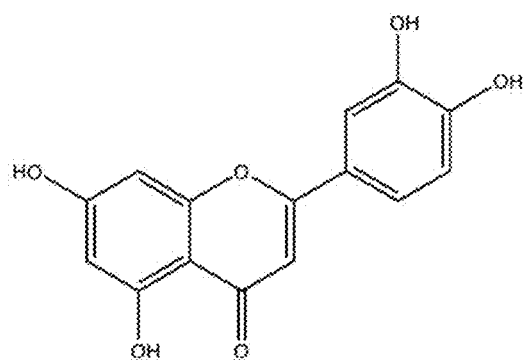
Figure 2:
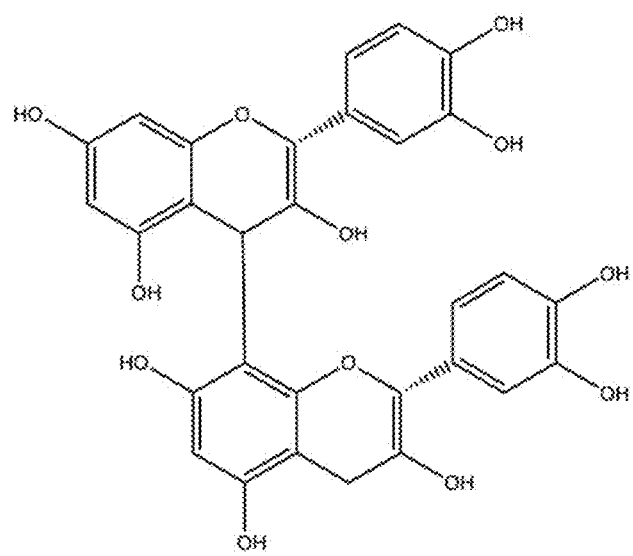

More than 8,000 polyphenolic compounds have been identified in plants. These polyphenolic compounds are secondary metabolites of plants and are generally involved in defense against ultraviolet radiation, viruses, or bacteria, as well as coping with environments by developing colors, smell, and flavor in plants [1]. The compounds can be classified into different groups by their structures and functional groups. The main classes of dietary polyphenols are phenolic acids, flavonoids and proanthocyanidins (FIG. 2).

Phenolic Acids

Figure 3:
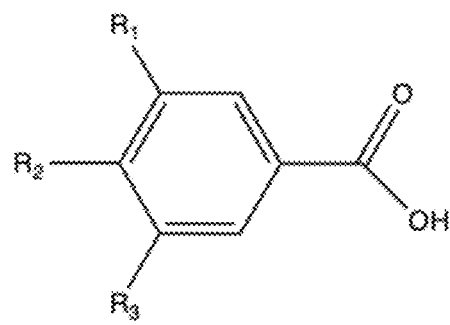
FIG. 3. Common chemical structures of phenolic acids.
Figure 3:
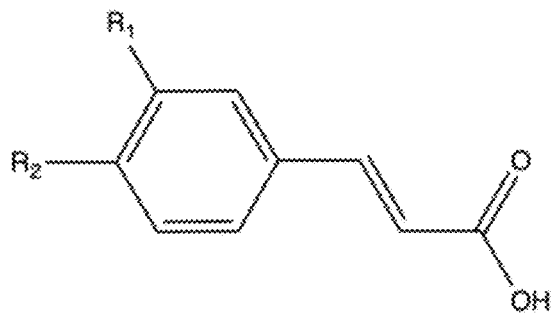
Figure 3:
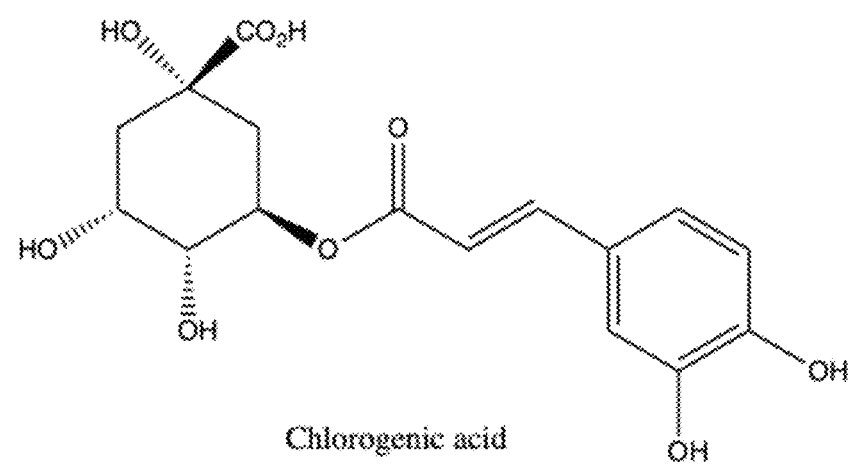
Figure 4A:
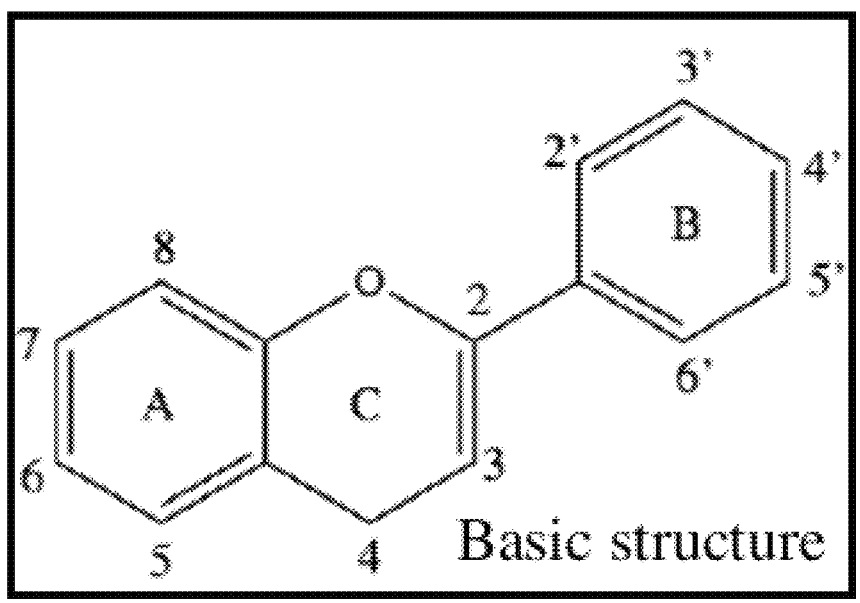
FIGS. 4A-4G. Chemical structures of flavonoids and its subclasses.
Figure 4B:
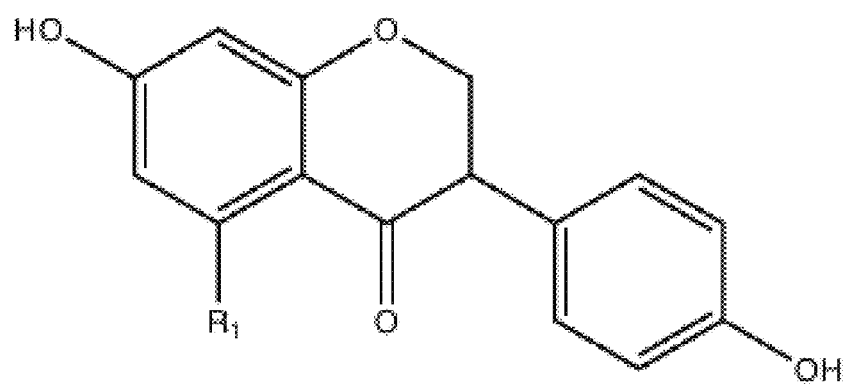
Figure 4C:
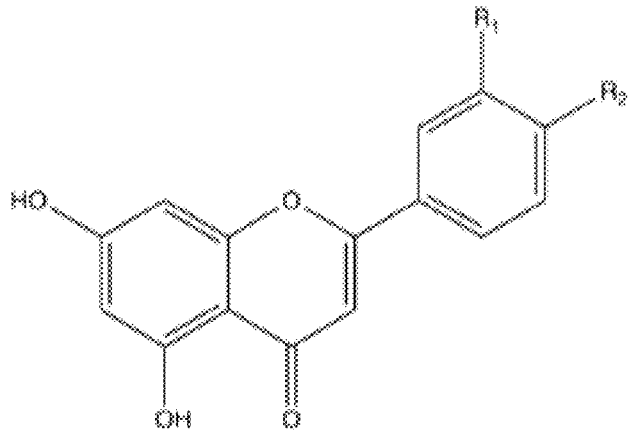
Figure 4D:
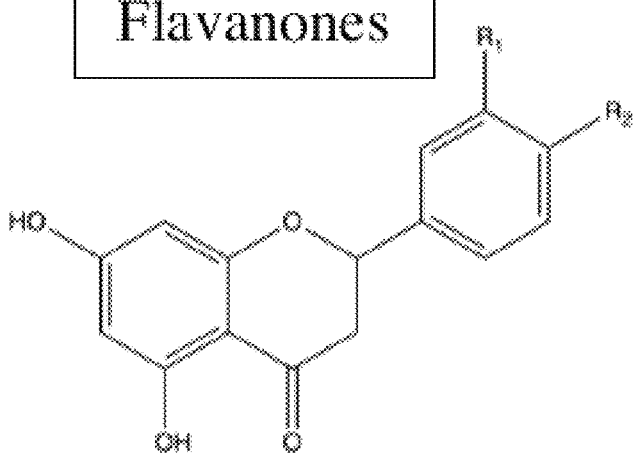
Figure 4E:
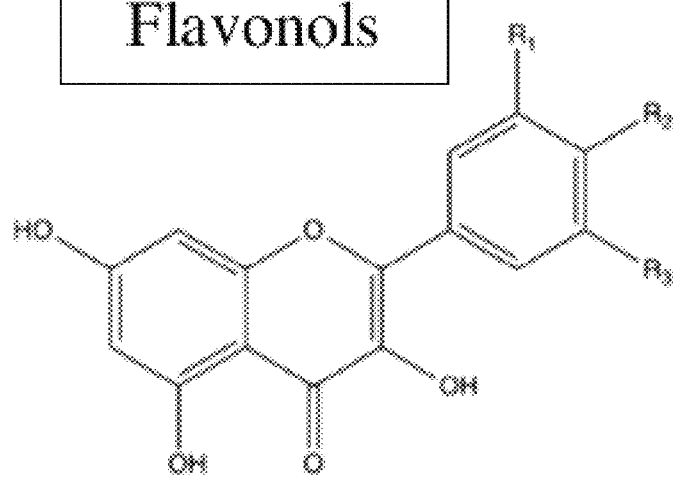
Figure 4F:
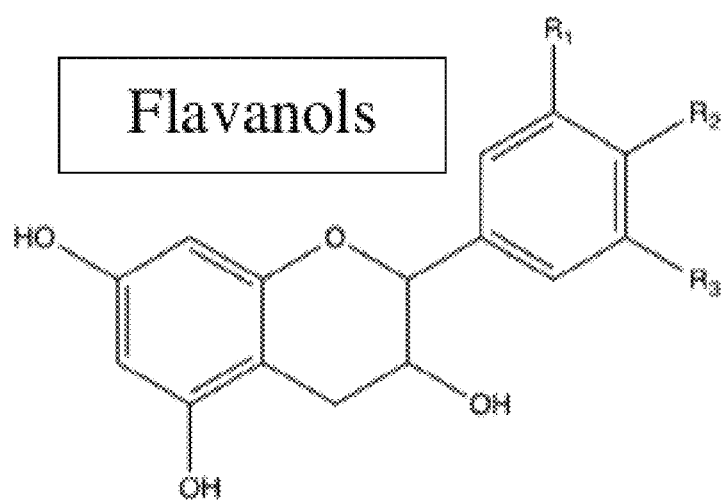
Figure 4G:
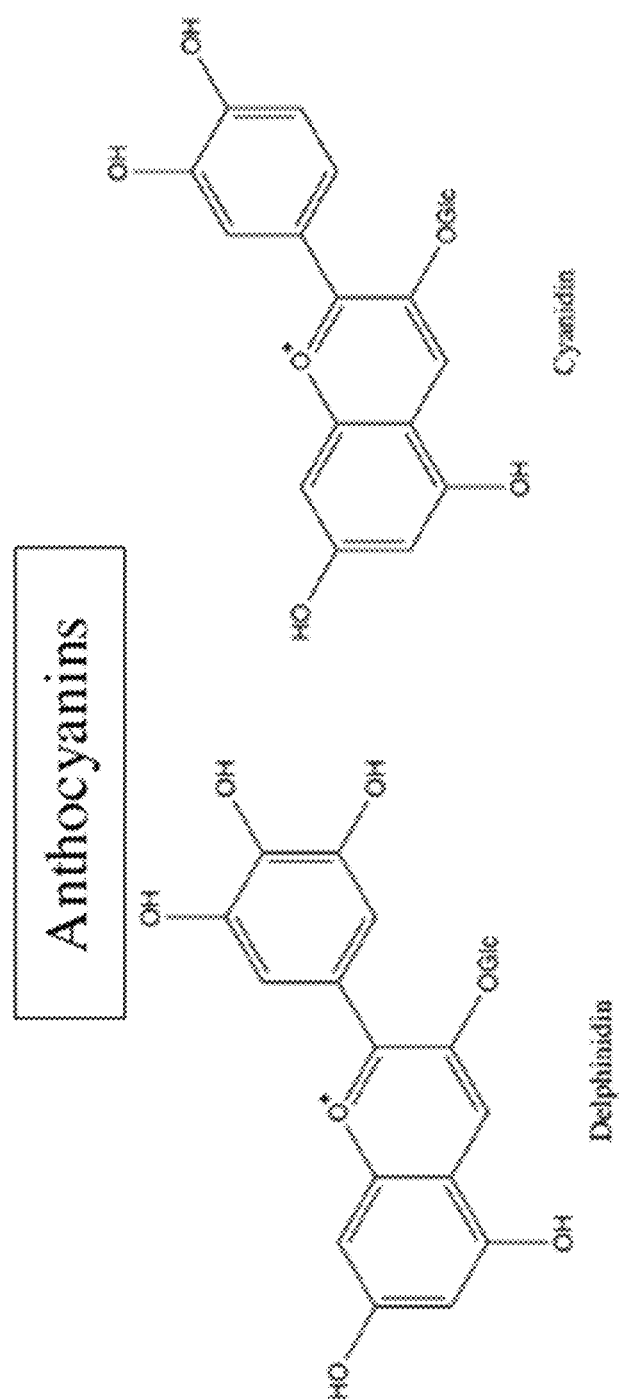

Phenolic acids are phenolic compounds having one or more carboxylic acid group. They are found in high concentrations in seeds, skins of fruits and leaves of vegetables and plants [2]. Phenolic acids are divided into two subgroups: hydroxybenzoic and hydroxycinnamic acid (FIG. 3). Hydroxybenzoic acids are derived from benzoic acid and they are in the form of C6-C1. They are bound to glycosides, cell wall lignins and rarely exist in free form [3]. The four commonly found hydroxybenzoic acids are p-hydroxybenzoic, protocatechuic, vanillic and syringic acids. On the other hand, hydroxycinnamic acids, derived from cinnamic acids, are the most common phenolics acids in plant tissues. They occur mostly in the associated form as esters with quinic acid, shikimic acid and tartaric acid or glucosides associated with glucose [4-8]. The four most common hydroxycinnamic acids are ferulic, caffeic, p-coumaric, and sinapic acids. Caffeic and quinic acid combine to form chlorogenic acid, which is the most abundant soluble bound hydroxycinnamic acid present. A single cup of coffee may contain 70-350 mg chlorogenic acid [9].

Flavonoids

Flavonoids share a common basic structure comprising two aromatic rings (A and B) separated by an oxygen-containing six membered heterocyclic ring (C). They can be subdivided into subgroups depending on the carbon of the C ring where the B ring is attached and the degree of unsaturation and oxidation of the C ring. The subgroups are therefore divided as: flavones, flavonols, flavanones, isoflavones, flavanols and anthocyanins (FIGS. 4A-4G). In nature, flavonoids are also widely distributed in plant kingdom. They constitute one of the most characteristic classes of compounds in higher plants because the flavonoid anthocyanins are recognized for their attractive colors in flowers, fruits, and leaves [10]. They are also abundant in foods and beverages, such as fruits, vegetables, tea, cocoa, and wine.

Flavones have a double bond between C2 and C3 in the flavonoid skeleton and a ketone group at C4. They consist mainly of glycosides of luteolin and apigenin. Celery, parsley, red peppers, chamomile, and mint are among the major sources of flavones. Chamomile and parsley have the highest flavone concentrations, with 5320 mg apigenin O-glycoside/100 g dried chamomile flowers or 1350 mg/100 g dried parsley leaf [11, 12]. Along with other flavonoids, flavones can act as UVB protectants in plants because they exhibit absorption band in the range of 280-315 nm [13, 14]. Flavones can also protect against insects, fungal diseases, and act as natural pesticides [15].

Flavanones, also known as dihydroflavones, are one of the important subgroups of flavonoids. Unlike flavones, they have a single bond between C2 and C3 on the heterocyclic C ring. Flavanones are present in high concentrations in citrus fruits. The main aglycones are naringenin in grapefruit, hesperidin in oranges and eriodictyol in lemons. Orange juice contains 200-600 mg hesperidin/L and grapefruit juice contains 18-53 naringenin mg/L [16, 17]. These compounds are responsible for the bitter taste of the juice and the peel of the citrus fruits.

Isoflavones are predominantly found in soybeans and legumes. The three main isoflavones are genistein, daidzein and glycitein. They are diphenolic compounds with a chemical structure similar to estrogen that binds to estrogen receptors alpha (ERα) and beta (ERβ) [18, 19]. Therefore, isoflavones are also refer to as phytoestrogens. They can have estrogenic or anti-estrogenic activity depending on estrogen levels. The isoflavones block the binding of potent estrogens because of the structural similarity, potentially preventing hormone-related cancer like breast cancer [20, 21]. Soy foods contain 25-466 mg/100 g isoflavones [22-24].

Flavonols are flavonoids with a ketone and a hydroxyl group on the heterocyclic six-membered ring. These compounds are generally present in foods as C3-glycosides. They are abundant in a variety of fruits and vegetables, such as onions, kale, lettuce, tomatoes, apples, grapes, and berries [25-28]. Apart from food sources, red wine and tea are important sources of flavonols [29]. The most common flavonols are kaempferol, quercetin and myricetin. In mixed green and black tea, the total flavonol content is 21.0 to 32.8 mg/L containing conjugated quercetin, kaempferol and myricetin [30].

Figure 5:
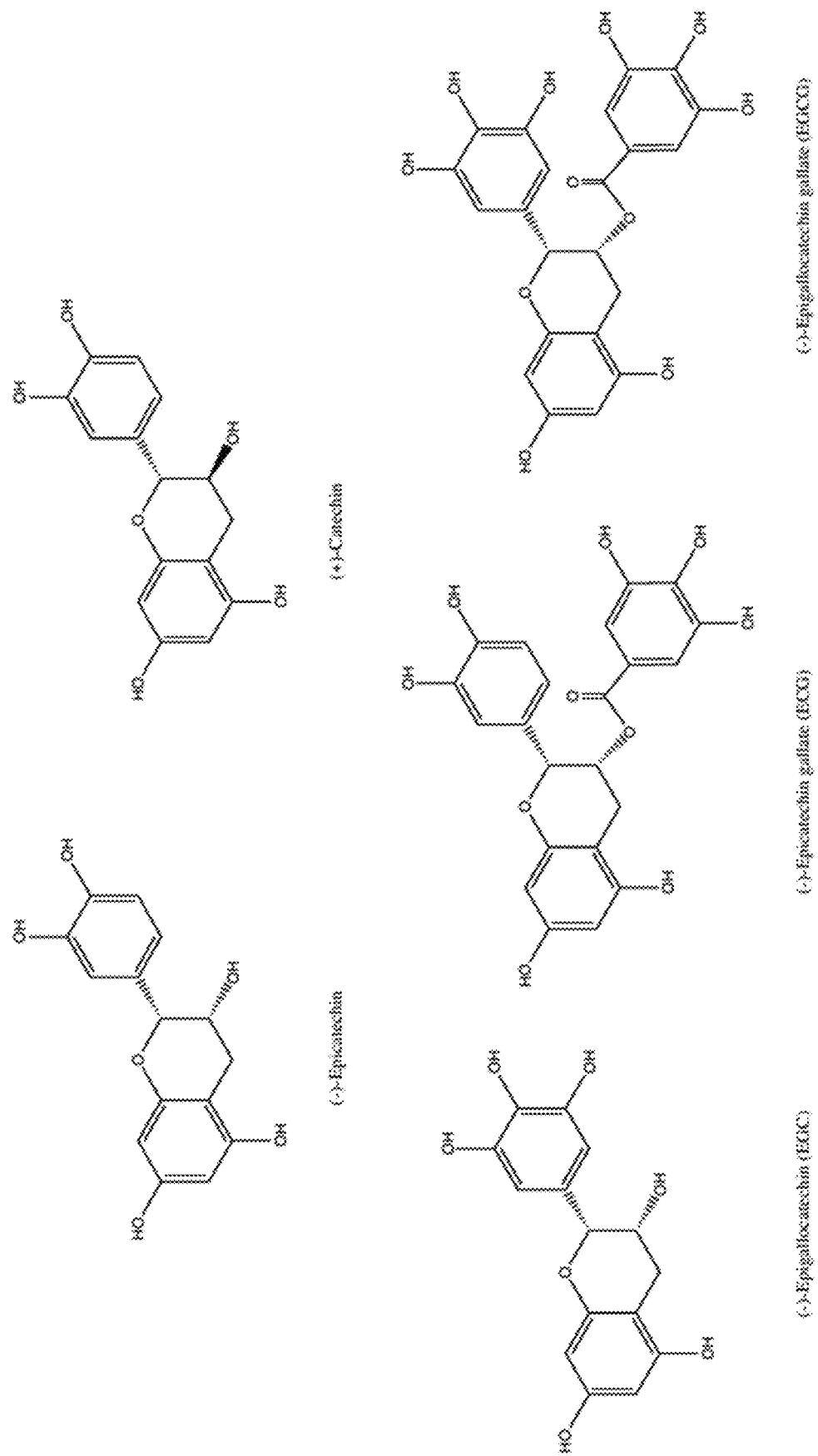
FIG. 5. Chemical structures of representative flavanols.

Flavanols, also known as dihydroflavonols, are referred to as flavan-3-ols, the monomer form of catechin. They are the building blocks for proanthocyanidins. (−)-Epicatechin and (+)-catechin are flavanol monomers. Unlike other flavonoids that usually exist in glucoside forms, flavanols are present in the aglycone form as monomers, oligomers or esterified with gallic acid to form (−)-epigallocatechin (EGC), (−)-epicatechin gallate (ECG) and (−)-epigallocatechin gallate (EGCG) (FIG. 5). (−)-Epicatechin and (+)-catechin are the main flavanols in fruits such as apples, blueberries, peaches, and apricots, whereas EGC, ECG and EGCG occur in grapes, red wine, and tea. Cocoa is also an important source of flavanols [31-33]. In cocoa, (−)-epicatechin is the major monomeric flavanol, having 116-730 mg/kg which is 35% of its total flavonoid content [34].

Figure 6:
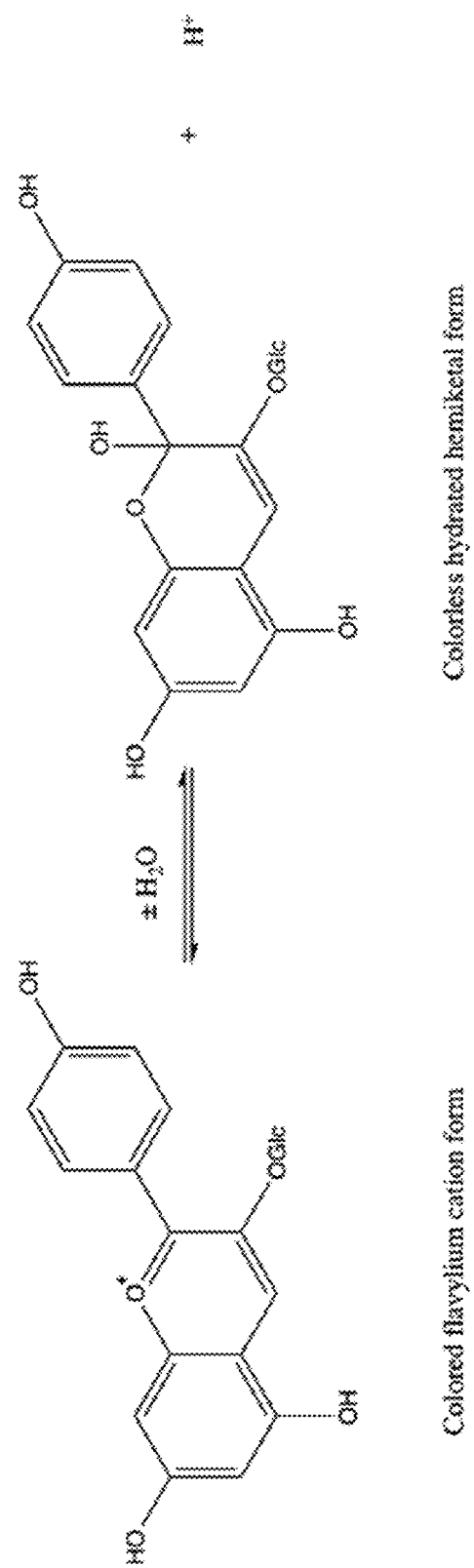
FIG. 6. Transformation of anthocyanin flavylium cation.

Anthocyanins are water-soluble pigments in higher plants that impart a pink, red, blue, or purple color. It has the same C6-C3-C6 structure as other flavonoids, except that it contains positive charge at the oxygen atom in the middle ring, known as the flavylium (2-phenylchromenylium) ion (FIG. 6). In acidic conditions, anthocyanins appear to be red and are predominantly in the form of flavylium cations. Under neutral conditions anthocyanins are predominately hydrated into hemiketal forms and appear to be colorless. Under basic conditions, anthocyanins are predominately quinoidal bases, and also pigmented [35]. Most of the anthocyanins have higher stability in acidic conditions compared with basic conditions as anthocyanins are very sensitive to pH. They are highly reactive molecules and therefore sensitive to degradation caused by light, temperature, oxygen, pH, and enzymes that affect their stability and color [36-38]. The stability can be improved by glycosylation, esterification with organic acids, the addition of amino acids or by formation of complexes with other flavonoids through copigmentation [39, 40]. Generally, anthocyanins exist in forms of glycosides and aglycones. The most common anthocyanins are cyanidin, delphinidin, pelargonidin, peonidin, malvidin and petunidin and their distribution in fruits and vegetables is 50%, 12%, 12%, 12%, 7% and 7% respectively [41].

Proanthocyanidins

Proanthocyanidins are also known as condensed tannins. Proanthocyanidins include procyanidins, prodelphinidinins, and propelargonidins. On the basis of B-ring hydroxylation, PACs can be further classified as properlargonidins (4-OH), procyanidins (3,4-OH), or prodelphinidins (3,4,5-OH). Neilson et al. 2016 (Andrew P. Neilson, Sean F. O'Keefe, and Bradley W. Bolling. High-Molecular-Weight Proanthocyanidins in Foods: Overcoming Analytical Challenges in Pursuit of Novel Dietary Bioactive Components *Annu. Rev. Food Sci. Technol.* 2016. 7:3.1-3.22). Proanthocyanidins are dimers, oligomers and polymers of flavan-3-ols (+)-catechin, (−)-epicatechin, (+)-afzelechin, (+)-gallocatechin, (+)-fisetinidol, and (+)-robinetinidol that are bound between C4 and C8 or C4 and C6. Both are called B-type proanthocyanidins. A-type proanthocyanidins are flavan-3-ol monomers and are linked by an ether bond between C2 and O7 in addition to C4 and C6 or C4 and C8. Their molecular weight is dependent on the degree of polymerization, generally between 3 and 11 [42,43]. It is found that the degree of polymerization could be as high as 80 in grape skins extract [44]. Proanthocyanidins are responsible for the astringent taste of foods such as grapes, apples, berries, chocolate, and beverages such as wine beer and tea through the formation of complexes with salivary proteins. Proanthocyanidins are also important in generating the flavor and the taste of wine. Because grape skin is rich in proanthocyanidins, the inclusion of the skins during wine fermentation retains high proanthocyanidins content in red wines, with an average of 175 mg/L, which is around 20 times higher than that of white wines where the skins are removed [45].

Analytical Methods for Polyphenol Quantification

Polyphenols play a critical role in the functional properties and physical properties in fruits and vegetables. Therefore, accurate measurement is very useful for the identification and quantification of polyphenols. Several analytical methods are commonly used to determine the polyphenol content in fruit juices and beverages. The pH differential, Folin-Ciocalteu and 4-dimethylaminocinnamaldehyde (DMAC) are the most widely used methods for polyphenol quantification.

pH Differential Method

The pH differential method is used to determine the anthocyanin content in fruit juices and beverages [46]. It is based on the structural transformation of anthocyanin pigments by a change in pH. The colored flavylium cation form dominates at pH 1.0. Where at pH 4.5 the hemiketal form dominates. The difference in the absorbance at 520 nm of anthocyanin pigments is proportional to the concentration of the anthocyanin pigments.

Folin-Ciocalteu Method

The Folin-Ciocalteu method is widely used for quantification of total phenols content [47]. Phenols are responsible for the oxidation/reduction reaction, which involves a transfer of electrons between phenols and quinone. The Folin-Ciocalteu reagent contains phosphomolybdic/phosphotungstic acid which forms a blue chromophore when the phenols are oxidized to quinone. The reduced Folin-Ciocalteu reagent is detected spectroscopically at 765 nm and the total phenol content is expressed using gallic acid equivalents. However, as an electron transfer based assay, Folin-Ciocalteu measures the activity of all reducing agents in present in the matrix. Reducers such as thiols, amino acids, proteins, some vitamins, and inorganic ions could interfere the accuracy of this assay [48-50].

4-Dimethylaminocinnamaldehyde (DMAC) Method

The DMAC method is used for total proanthocyanidin quantification [51]. It measures both A and B-type proanthocyanidins together. In comparison to the vanillin and acid butanol assays, DMAC assay is by far the most reliable method to measure proanthocyanidin content because of less interference at the detecting wavelength. The aldehyde DMAC is protonated in the presence of a strong acid solution and forms a carbocation that react with the terminal units on proanthocyanidins. The colored DMAC-proanthocyanidin complex is detected at 640 nm and the total proanthocyanidin content is expressed in catechin monomer equivalents. However, DMAC method has some limitations. It cannot provide exact information on the degree of polymerization (DP). Furthermore, it exhibited different reactivity towards proanthocyanidins with different DP and structural type [52]. Using monomer as quantification standards, the proanthocyanidin content can be underestimated on mass and molar basis.

Current Extraction Methods for Polyphenols

Traditional techniques involve conventional solvent extraction (CSE) and solid-liquid extraction (SLE), which encompasses methods like Soxhlet extraction (SE), percolation and maceration extraction. These methods have been utilized for more than a century for the isolation of polyphenols. However, the disadvantages pertaining to CSE and SLE such as excessive consumption of time, energy and solvents triggered the development of current cost-effective and greener techniques for the extraction of polyphenols [53]. Supercritical fluid extraction (SFE), ultrasound-assisted extraction (UAE), microwave-assisted extraction (MAE), pressurized liquid extraction (PLE) and pressurized hot water extraction (PHWE) are currently used as alternatives to the conventional extraction methods.

Supercritical Fluid Extraction (SFE)

The modern techniques have been increasingly popular due to their cost-effectiveness, eco-friendliness, and rapidity. SFE utilizes supercritical fluid that has the property of 2 individual phases: gaseous and liquid simultaneously. During the extraction, raw materials are contained in an extraction vessel. The extraction conditions can be adjusted by a pressure release valve and temperature controller in order to modify the viscosity, density, and solvation of the supercritical fluid. Finally, the polyphenol compounds dissolved in the fluid are separated from the fluid in a CO2-extract separator with an CO2 outlet valve. SFE effectively cuts down the usage of organic solvent and allows the recovery of the solvent due to its two-phase nature [54-56].

Ultrasound-Assisted Extraction (UAE)

Another extraction method commonly is UAE, where the ultrasonic waves generated by the operational frequencies transmit massive energy and pressure to the solid plant materials and cause cavitation. The ultrasonic waves break up solid particles so that the liquid solutes could leach out to the extraction phase. This method reduces the extraction time and increases the extraction rate of thermolabile polyphenols at mild temperature [57-60].

Pressurized Hot Water Extraction (PHWE)

PHWE is another popular green extraction method among the modern techniques using eco-friendly water as extractant [61-64]. It has a comparative advantage over conventional, time-consuming extraction methods. Nevertheless, disadvantages such as dissolution of polyphenols in nonpolar solvent CO2, dissolution of hydrophobic compounds in water, requirement for high pressure and costly infrastructure, degradation caused by hydroxyl radicals in ultrasound have restricted the widely acceptance of these techniques [53].

Extraction by Soybean Lecithin An alternative polyphenol extraction method, as shown herein, is with the use of lecithin or other phospholipid-containing compositions, such as soybean lecithin. We show that soybean lecithin induced polyphenol precipitation in both cranberry juice and grape juice.

Soybean Lecithin

Soybean lecithins are important natural emulsifiers used in the food, feed, and pharmaceutical industries. The world market for lecithin is estimated to surpass 530 kilo tons by 2024, propelling by the need to reduce calorie and sugar intake. Generally, lecithins can be obtained from egg yolk, various oilseeds such as rapeseed, soybeans, and sunflower seeds. Soybeans have been the primary source of lecithin because they are one of the most widely grown crops in the United States. However, lecithins derived from sunflower seeds are becoming increasingly popular because of the allergens in soy and the fact that most of the soy crop is genetically modified. Chemicals, including acetone and hexane, are used to extract the lecithin from soybean, whereas a gentler extraction process, cold press, is used to expel the oil from sunflower seeds and rapeseeds, followed by solvent extraction of the lecithin [65]. Among all vegetable oils, soybean oil contains the greatest amount of lecithin [66].

Production of Soy Lecithin

Crude soybean oil contains 2-3% phospholipids. The process to remove the phospholipids in the crude oil and further process it into lecithin uses four operations: hydration of phosphatides, separation of lecithin sludge, drying of sludge and cooling. For hydration, water (2-3%) is mixed thoroughly with the oil at 50-70° C. The phospholipids hydrate to form a sludge within an hour. The easily hydratable phospholipids are phosphatidylcholine (PC), phosphatidylinositol (PI) and lysophosphatidylcholine (LPC). Phosphatidylethanolamine (PE) and phosphatidic acid (PA) have poor hydration and therefore marked as non-hydratable phospholipids (NHP), which requires another degumming step with citric acid or phospholipase in order to hydrate them from the water-degummed oil [67, 68]. Next, the sludge is removed from the oil by centrifugation at 50-70° C. This step gives a crude soybean oil containing 0.3% non-hydratable phospholipids and lecithin gum containing 40-50% water [69]. After centrifugation, lecithin gum is dried to a low moisture content, <1% with a film evaporator or batch dryer. Natural lecithin has a brown color because of the presence of carotenoids and melanoids as well as Maillard reaction products from reducing sugars and PE [70]. Therefore, conditions like temperature and processing time are controlled in order to obtain lightly colored lecithin. Alternatively, a bleaching step is added before drying where the lecithin gum is treated with 35% $H_2O_2$. Finally, lecithin is cooled to below 50° C. in order to prevent further darkening. The ideal condition to store lecithin is at 20-30° C. and the lecithin can be easily stored for over a year without degradation of the product quality and functionality.

Composition of Soy Lecithin

Commercial soy lecithin is a complex mixture of 65-75% phospholipids, 35% triglycerides and smaller amounts of other substances containing carbohydrates, pigments, sterols, and sterol glycosides [71]. Phospholipids are a class of lipids that are formed by two hydrophobic hydrocarbon chains and a hydrophilic phosphate headgroup. Phospholipids can be divided into glycerophospholipids and sphingomyelins depending on the backbone. Major glycerophospholipids include PC, PE, PI, and PA.

Figure 7:
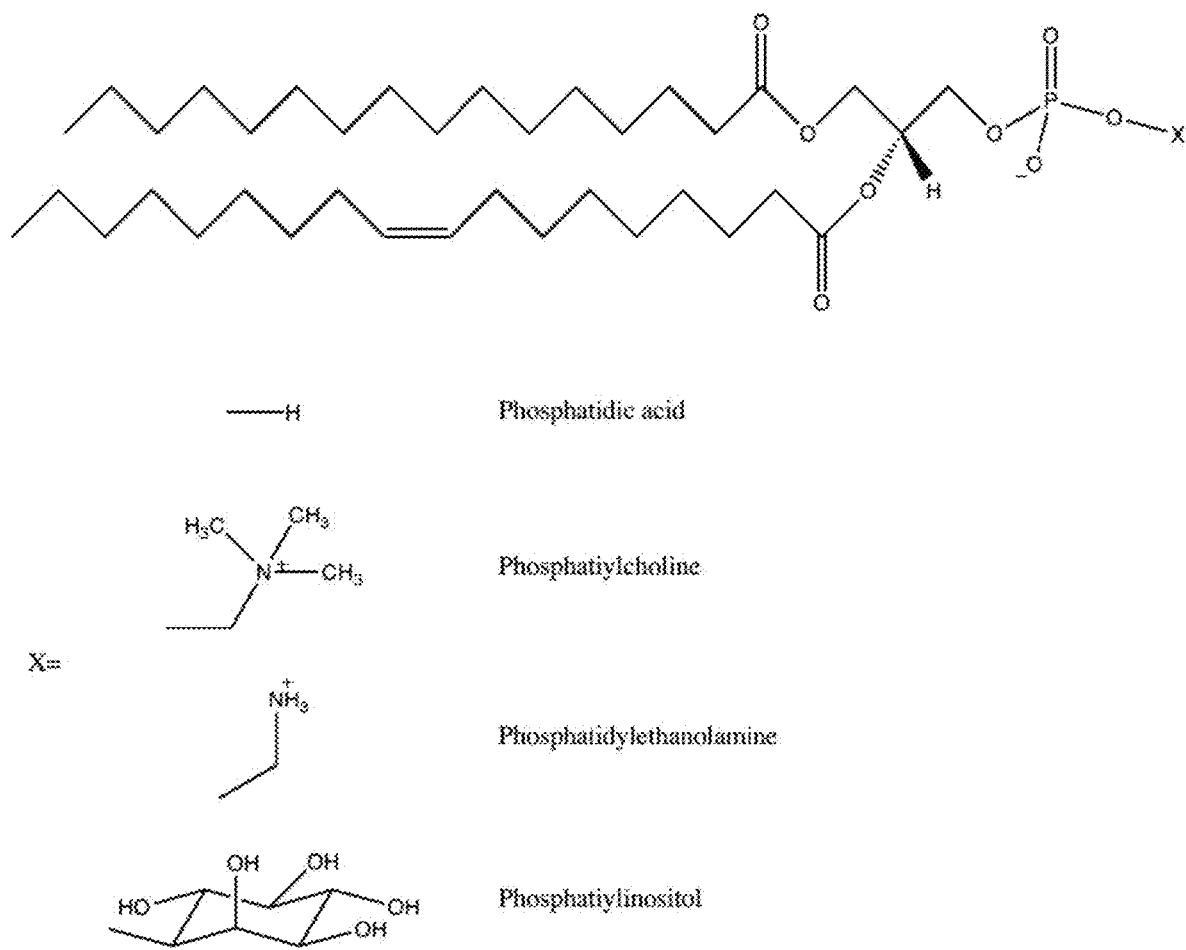
FIG. 7. Primary phospholipids in lecithin.

Phospholipids are amphiphilic compounds. Its main structure is constructed on a glycerol backbone linked to a phosphate headgroup as the hydrophilic region and fatty acid chains as the hydrophobic region (FIG. 7). The phosphate group of PA exhibits unique ionization property, depending on pH. Below a pH of 4.0, it carries a charge of zero, whereas above pH 12.0, it is fully deprotonated to a charge of −2. Because of the charge variation in response to deprotonation, it serves a critical role in binding of proteins and small compounds by hydrogen bonding. PC adds the additional choline cation, to the phosphate anion, which makes it a neutral zwitterion. PC is the most abundant phospholipid in cells and subcellular organelles amongst these phospholipids. In general, PC comprises of 40-50% of total phospholipids. PE is the second most abundant phospholipid in mammalian membranes. It has the basic structure of phosphatidic acid with an ethanolamine group. The pKa of the amino group is about 9.5. Under physiological pH, PE is also a zwitterion. PI has a unique headgroup that is made up by a cyclohexane carbohydrate named inositol. Therefore, PI has a −1 charge with the negatively charged phosphate group.

Properties of Phospholipids

The amphiphilic nature of phospholipids gives it the ability to form unique structures in water and lipids. The solubility of phospholipids in water depends on both the hydrophilic headgroup and the hydrophobic fatty acid chain [72, 73]. The phospholipids can be divided into four classes as a function of its solubility: class I, insoluble phospholipids that is very hydrophobic and has no solubility in water at all; class II, phospholipids with very low solubility, which swell in water; class IIIA, soluble phospholipids forming liquid crystals in water; class IIIB, soluble phospholipids forming micelles above the critical micelle concentration with no crystalline structure.

Figure 8:
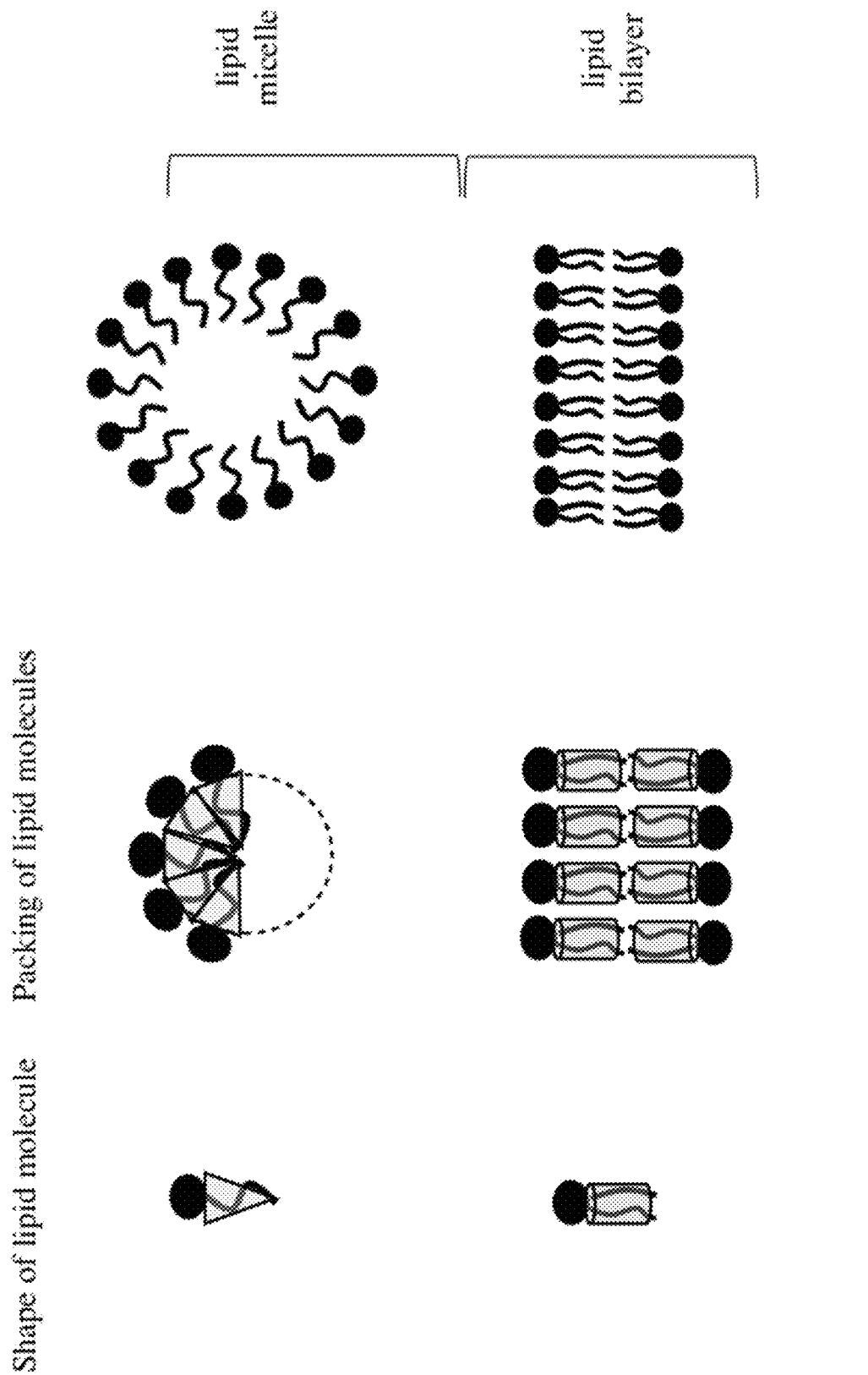
FIG. 8. Packing of lipid molecules.

When dispersed in water, phospholipid molecules spontaneously expose their hydrophilic heads to water and fold their hydrophobic tails away from water. Unlike the wedge-shaped lipid molecules where they form into spherical micelles with tails inward, cylinder-shaped phospholipid molecules form bilayers with the tails stacked between the hydrophilic headgroups [74]. The hydrophilic headgroups face towards water and the hydrophobic tails are buried in the interior, spontaneously forming lipid bilayer once exposed to water (FIG. 8).

Hydrophile-lipophile balance (HLB) is defined as the balance of the strength of the hydrophilicity and lipophilicity of a surfactant molecule on a scale of 1 to 20 [75]. It determines the type of preferred phospholipid emulsifiers to a given system, whether they are more suitable for oil-in-water (O/W) emulsions or water-in-oil (W/O) emulsions. Surfactants with high HLB values have a stronger ability to form O/W emulsions. Lecithin has varying HLB values of the based on the composition of the phospholipid molecules, as introduced by Davies [76]. Typical HLB values for soy lecithins are in the range of 1-12 [77].

Roles of Phospholipids on Cell Membranes

Membranes are important for cell survival by enclosing the critical cellular materials such as proteins, nucleic acids, and carbohydrates in the cell [79]. This structural barrier is made possible by the abundant phospholipids in the cell membrane. The phospholipid bilayers provide the structure to the cell membrane and also enable essential molecules to cross the membrane through diffusion, osmosis, and active transport [80]. Phospholipids also contribute to the membrane's flexibility and fluidity. Some phospholipids can form negative curvature, while some can form positive curvature depending on the molecular shape of the phospholipids. Membrane fluidity depends on the composition of phospholipids [81]. The membrane shows more fluidity if the hydrocarbon chains on the phospholipids are short or have double bonds that create kinks Phospholipids can also regulate cellular processes such as cell growth, signal transmission and immune surveillance. Therefore, the phospholipids render the membrane function rather dynamic.

Activity of Polyphenols in Association with Cell Membranes

Polyphenols are widely studied for their antioxidant, anti-inflammatory, anti-diabetes activities [82, 83]. Besides, they also exhibit strong superoxide-radical scavenging activity, allowing them to have anticarcinogenic properties [84]. There are many reports on the health benefits of polyphenols, the mechanisms in biological systems are complex. The interaction between polyphenols and cell membranes may partially explain the bioactivity of polyphenols. For example, the antibacterial effect of green tea catechins may result from increased membrane fluidity induced by polyphenols that associate with membrane phospholipids [85]. Furthermore, Sirk et al. proposed that green tea catechins associate with the polar phospholipid headgroup on the membrane surface by forming hydrogen bonds, with the phenolic hydroxyl group serving as hydrogen bond donors and oxygen atoms on the phosphate headgroups serving as hydrogen acceptors [86]. Results from solid-state NMR spectroscopy studies by Yu et al. showed that catechin, epigallocatechin (EGC) and tannin incorporated into the lipid membrane either on the surface or to the hydrophobic region based on the polyphenol polarity [87]. The quadrupolar splitting in the NMR spectra upon tannin addition indicated significant disorders of the acyl chains of the lipid bilayers, which suggested the membrane structure was disrupted by hydrophobic interaction, while the polar catechin and EGC interacted weakly with the acyl chain and retained on the membrane surface [88]. Phan et al. demonstrated that polyphenols induced transformation of lipid membranes hydrogen bonding and hydrophobic interaction depending on the polyphenol structural properties [89]. They discovered that flavonoids were able to form hydrogen bonds with head groups of the membrane phospholipids on the surface. The side chains of the polyphenols could also impact this interaction. The more hydrophilic moieties polyphenols have (e.g. hydroxyl, gallate, galloyl, glucoside), the more interactive they are with the membrane. Comparatively, trans-stilbenes tended to penetrate the membrane lipids so that the benzyl ring structure interacted with the hydrophobic region deeply to the interior [89]. These findings are critical for understanding how polyphenols exhibit health benefits through biological membrane activity and to provide insights about the important role of the phospholipid-polyphenol interaction demonstrated by various structurally different polyphenols upon absorption.

Conclusion

Polyphenols have shown promising in vitro pharmacological effects, but poor absorption in vivo. However, structures formed with phospholipid and polyphenols could enhance the bioavailability of the polyphenols. Phospholipid emulsions, liposomes and nanoparticles may be used to deliver or stabilize polyphenols. The membrane permeability can be greatly improved, and the bioactive polyphenols can be more readily absorbed.

REFERENCES

[1]. Heleno, S. A., Martins, A., Queiroz, M. J., Ferreira, I. C. Bioactivity of phenolic acids: metabolites versus parent compounds: a review. Food Chem. 2015, 173, 501-513.

[2]. Shahidi, F., Nacsk, M. Food Phenolics: Sources, Chemistry, Effects, and Application. Technomic Publishing Co., Inc., Lancaster, Pa. (1995).

[3]. Dey, P. M., Harborne, J. B. Phenolic metabolism (Eds.). Plant Biochemistry, Academic, London (1997).

[4]. Manach, C., Scalbert A., Morand C., Remesy C., Jimenez L. Polyphenols: Food sources and bioavailability. Am. J. Clin. Nutr. 2004, 79, 727-747.

[5]. Huang C. J., Zayas J. F. Phenolic acids contribution to taste characteristic of corn germ protein flour products. J. Food Sci. 1991, 56, 1308-1310.

[6]. Ghasemzadeh A., Ghasemzadeh N. Flavonoids and phenolic acids: Role and biochemical activity in plants and human. J. Med. Plants Res. 2011, 5, 6697-6703.

[7]. Herrmann, K. Occurrence and content of hydroxycinnamic and hydroxybenzoic acid compounds in foods. Crit. Rev. Food Sci. Nutr. 1989, 28, 315-347.

[8]. de Simón, B. F., Hernández, T., Estrella, I. et al. Variation in phenol content in grapes during ripening: low-molecular-weight phenols. Z Lebensm. Unters. Forch. 1992, 194, 351-354.

[9]. Clifford, M. N. Chlorogenic acids and other cinnamates—nature, occurrence and dietary burden. J. Sci. Food Agric. 1999, 79, 362-72.

[10]. de Groot, H., Rauen, U. Tissue injury by reactive oxygen species and the protective effects of flavonoids. Fundam. Clin. Pharmacol. 1998, 12, 249-255.

[11]. Yang, R., Lin, S., Kuo, G. Content and distribution of flavonoids among 91 edible plant species. Asia Pac. J. Clin. Nutr. 2008, 17, 275-279.

[12]. Srivastava, J. K., Gupta, S. Extraction, characterization, stability and biological activity of flavonoids isolated from chamomile flowers. Mol. Cell Pharmacol. 2009, 1, 138.

[13]. Svehlíková V., Repcák M. Apigenin chemotypes of Matricaria chamomilla. L. Biochem. Syst. Ecol. 2006, 34, 654-657.

[14]. Lechtenberg, M., Zumdick, S., Gerhards, C., Schmidt, T. J., Hensel, A. Evaluation of analytical markers characterizing different drying methods of parsley leaves (Petroselinum crispum L.). Pharmazie, 2007, 62, 949-954.

[15]. Lattanzio, V., De Cicco, V., Di Venere, D., Lima, G., Salerno, M. Antifungal activity of phenolics against fungi commonly encountered during storage. Ital. J. Food Sci. 1994, 6, 23-30.

[16]. Tomas-Barberan, F. A., Clifford, M. N. Flavanones, chalcones and dihydrochalcones—nature, occurrence and dietary burden. J. Sci Food. Agric. 2000, 80, 1073-1080.

[17]. Alam, M. A., Subhan N., Rahman, M. M., Uddin, S. J., Reza, H. M., Sarker, S. D. Effect of Citrus Flavonoids, Naringin and Naringenin, on Metabolic Syndrome and Their Mechanisms of Action. Advances in Nutrition, 2014, 5, 404-417.

[18]. Kuiper, G. G., Carlsson, B., Grandien, K., Enmark, E., Haggblad, J., Nilsson, S., Gustafsson, J. A. Comparison of the ligand binding specificity and transcript tissue distribution of estrogen receptors alpha and beta. Endocrinology. 1997, 138, 863-870.

[19]. Kuiper, G. G., Lemmen, J. G., Carlsson, B., Corton, J. C., Safe, S. H., van der Saag, P. T., van der Burg, B., Gustafsson, J. A. Interaction of estrogenic chemicals and phytoestrogens with estrogen receptor beta. Endocrinology. 1998, 139, 4252-4263.

[20]. Kang, X., Zhang, Q., Wang, S., Huang, X., Jin, S. Effect of soy isoflavones on breast cancer recurrence and death for patients receiving adjuvant endocrine therapy. Can. Med. Assoc. J. 2010, 182, 1857-1862.

[21]. Ziaei, S., Halaby, R. Dietary Isoflavones and Breast Cancer Risk. Medicines. 2017, 4, 18-28.

[22]. Sakai, T., Kogiso, M. Soy isoflavones and immunity. J. Med. Investig. 2008, 55, 167-173.

[23]. Cassidy, A., Hanley, B., Lamuela-Raventos, R. M. Isoflavones, lignans and stilbenes—Origins, metabolism and potential importance to human health. J. Sci. Food Agric. 2000, 80, 1044-1062.

[24]. Perez-Jimenez, J., Neveu, V., Vos, F., Scalbert, A. Systematic analysis of the content of 502 polyphenols in 452 foods and beverages: An application of the phenol-explorer database. J. Agric. Food Chem. 2010, 58, 4959-4969.

[25]. Manach, C., Scalbert, A., Morand, C., Rémésy, C., Jimenez, L. Polyphenols: food sources and bioavailability. Am. J. Clin. Nutr. 2004, 79, 727-747.

[26]. Hertog, M. G. L., Hollman, P. C. H., Katan, M. B. Content of potentially anticarcinogenic flavonoids of 28 vegetables and 9 fruits commonly consumed in the Netherlands. J. Agric. Food Chem. 1992, 40, 2379-2383.

[27]. Price, K. R., Rhodes, M. J. C. Analysis of the major flavonol glycosides present in four varieties of onion (*Allium cepa*) and changes in composition resulting from autolysis. J. Sci. Food Agric. 1997, 74, 331-339.

[28]. Crozier, A., Lean, M. E. J., McDonald, M. S., Black, C. Quantitative analysis of the flavonoid content of commercial tomatoes, onions, lettuce, and celery. J. Agric. Food Chem. 1997, 45, 590-595.

[29]. Hertog, M. G. L., Hollman, P. C. H., van de Putte, B. Content of potentially anticarcinogenic flavonoids of tea infusions, wines and fruit juices. J. Agric. Food Chem. 1993, 41, 1242-1246.

[30]. Crozier, A., Burns, J., Aziz, A. A., Stewart, A. J., Rabiasz, H. S., Jenkins, G. I., Edwards, C. A., Lean, M. E. J. Antioxidant flavonols from fruits, vegetables and beverages: measurements and bioavailability. Biol. Res. 2000, 33, 79-83.

[31]. Gu, L., Kelm, M. A., Hammerstone, J. F., Beecher, G., Holden, J., Haytowitz, D., Gebhardt, S., Prior, R. L. Concentrations of proanthocyanidins in common foods and estimations of normal consumption. J. Nutr. 2004, 134, 613-617.

[32]. Nonaka, G., Sakai, R., Nishioka, I. Hydrolysable tannins and proanthocyanidins from green tea. Phytochemistry. 1984, 23, 1753-1755.

[33]. Ravindranath, M. H., Ramasamy, V., Moon, S., Ruiz, C., Muthugounder, S. Differential growth suppression of human melanoma cells by tea (*Camellia sinensis*) epicatechins (ECG, EGC and EGCG). Evid. Based Complement Alternat. Med. 2009, 6, 523-530.

[34]. Hackman, R. M., Polagruto, J. A., Zhu, Q. Y. et al. Flavanols: digestion, absorption and bioactivity. Phytochem. Rev. 2008, 7, 195-208.

[35]. Brouillard, R., Dubois, J. E. Mechanism of the structural transformations of anthocyanins in acidic media. J. Am. Chem. Soc. 1977, 99, 1359-1364.

[36]. Roobha, J. J., Saravanakumar, M., Aravindhan, K. M., Devi, P. S. The effect of light, temperature, pH on stability of anthocyanin pigments in Musa *Acuminata* Bract. Research in Plant Biology. 2011, 1, 5-12.

[37]. Fossen, T., Cabrita, L., Andersen, O. M. Colour and stability of pure anthocyanins influenced by pH including the alkaline region. Food Chem. 1998, 63, 435-440.

[38]. West, M. E., Mauer, L. J. Color and chemical stability of a variety of anthocyanins and ascorbic acid in solution and powder forms. Journal of Agricultural and Food Chemistry. 2013, 61, 4169-4179.

[39]. Chung, C., Rojanasasithara, T., Mutilangi, W., McClements, D. J. Enhanced stability of anthocyanin-based color in model beverage systems through whey protein isolate complexation. Food Res Int. 2015, 76, 761-768.

[40]. Trouillas, P., Sancho-Garcia, J. C., De Freitas, V., et al. Stabilizing and modulating color by copigmentation: insights from theory and experiment. Chem Rev. 2016, 116, 4937-4982.

[41]. Castaneda-Ovando, A., Pacheco-Hernandez, M. D., Paez-Hernandez, M. E., Rodriguez, J. A., Galan-Vidal, C. A. Chemical Studies of anthocyanins: A review. Food Chemistry. 2009, 113, 859-871.

[42]. Gu, L., Kelm, M. A., Hammerstone, J. F., Beecher, G., Holden, J., Haytowitz, D., Gebhardt, S., Prior, R. L. Concentrations of proanthocyanidins in common foods and estimations of normal consumption. Journal of Nutrition. 2004, 134, 613-617.

[43]. Santos-Buelga, C., Scalbert, A. Proanthocyanidins and tannin-like compounds in human nutrition. J. Food Sci. Agric. 2000, 80, 1094-1117.

[44]. Souquet, J., Cheynier, V., Brossaud, F., Moutounet, M. Polymeric proanthocyanidins from grape skins. Phytochemistry. 1996, 43, 509-512.

[45]. Sanchez, M. C., Cao, G., Ou, B., Prior, R. L. Anthocyanin and proanthocyanidin content in selected white and red wines. Oxygen radical absorbance capacity comparison with nontraditional wines obtained from highbush blueberry. Journal of Agricultural and Food Chemistry. 2003, 51, 4889-4896.

[46]. Giusti, M. M., Wrolstad, R. E. Anthocyanins. Characterization and measurement with UV-visible spectroscopy. In R. E. Wrolstad (Ed.), Current Protocols in Food Analytical Chemistry, NewYork: Wiley (2001).

[47]. Singleton, V. L., Rossi, J. A. Colorimetry of total phenolics with phosphomolybdic-phosphotungstic acid reagents. Am. J. Enol. Vitic. 1965, 16, 144-158.

[48]. Prior, R. L., Wu, X., Schaich, K. Standardized methods for the determination of antioxidant capacity and phenolics in foods and dietary supplements. J. Agric. Food Chem. 2005, 53, 4290-4302.

[49]. Everette, J. D., Bryant, Q. M., Green, A. M., Abbey, Y. A., Wangila, G. W., Walker, R. B. Thorough study of reactivity of various compound classes toward the Folin-Ciocalteu reagent. J. Agric. Food Chem. 2010, 58, 8139-8144.

[50]. Chen, L. Y., Cheng, C. W., Liang, J. Y. Effect of esterification condensation on the Folin-Ciocalteu method for the quantitative measurement of total phenols. Food Chem. 2015, 170, 10-15.

[51]. Scalbert A. Quantitative methods for the estimation of tannins in plant tissues. In: Plant polyphenols: synthesis, properties, and significance. Hemmingway R W and Laks P S. (ed). Plenum Press. New York, N.Y. 1992, 259-280.

[52]. Wang, Y., Singh, A. P., Hurst, W. J., Glinski, J. A., Koo, H., Vorsa, N. Influence of degree-of-polymerization and linkage on the quantification of proanthocyanins using 4-Dimethylaminocinnamaldehyde (DMAC) Assay. J. Agric. Food Chem. 2016, 64, 2190-2199.

[53]. Cravotto, G., Binello, A., Orio, L. Green extraction techniques. Agro. Food Ind. Hi-Tech. 2011, 22, 57-59.

[54]. Herrero, M., Mendiola, J. A., Cifuentes, A., Ibáñez, E. Supercritical fluid extraction: recent advances and applications. J. Chromatogr. A. 2010, 1217, 2495-2511.

[55]. Sairam, P., Ghosh, S., Jena, S., Rao, K. N. V., Banji, D. Supercritical fluid extraction (SFE)—an overview. J. Res. Pharma. Sci. 2012, 2, 112-120.

[56]. King, J. W. Modern supercritical fluid technology for food applications. Annu. Rev. Food Sci. Technol. 2014, 5, 215-238.

[57]. Vilkhu, K., Mawson, R., Simons, L., Bates, D. Applications and opportunities for ultrasound-assisted extraction in the food industry—a review. Innov. Food Sci. Emerg. Technol. 2008, 9, 161-169.

[58]. Tadeo, J. L., Sánchez-Brunete, C., Albero, B., García-Valcárcel, A. I. Application of ultrasound-assisted extraction to the determination of contaminants in food and soil samples. J. Chromatogr. A. 2010, 1217, 2415-2440

[59]. Kentish, S., Feng, H. Applications of power ultrasound in food processing. Annu. Rev. Food Sci. Technol. 2014, 5, 263-284.

[60]. Awad, T. S., Moharram, H. A., Shaltout, O. E., Asker, D., Youssef, M. M. Applications of ultrasound in analysis, processing and quality control of food: a review. Food Res. Int. 2012, 48, 410-427.

[61]. Teo, C. C., Tan, S. N., Yong, J. W., Hew, C. S., Ong, E. S. Pressurized hot water extraction (PHWE). J. Chromatogr. A. 2010, 1217, 2484-2494.

[62]. Plaza, M., Turner, C. Pressurized hot water extraction of bioactives. Trend Anal Chem. 2015, 71, 39-54.

[63]. Plaza. M., Abrahamsson, V., Turner, C. Extraction and neoformation of antioxidant compounds by pressurized hot water extraction from apple byproducts. J. Agric. Food Chem. 2013, 61, 5500-5510

[64]. Vergara-Salinas, J. R., Cuevas-Valenzuela, J., Perez-Correa, J. R. Pressurized hot water extraction of polyphenols from plant material. In: Kumar V G, Tuohy M G, Lohani M, O'Donovan A, editors. Biotechnology of bioactive compounds: sources and applications. New Jersey: John Wiley & Sons Inc. 2015, 63-101.

[65]. van Nieuwenhuyzen, W., Tomás, M. C. Update on vegetable lecithin and phospholipid technologies. Eur. J. Lipid Sci. Technol. 2008, 110, 472-486.

[66]. Pires, L. N., Brandao, G. C., Teixeira, L. S. G. Determination of phospholipids in soybean lecithin samples via the phosphorus monoxide molecule by high-resolution continuum source graphite furnace molecular absorption spectrometry. Food Chemistry. 2017, 225, 162-166.

[67]. Ringers, H. J., Seegers, J. C. Degumming process for triglyceride oils. U.S. Pat. No. 4,049,686 (1977).

[68]. Buchold, H., Boensch, R., Schroeppel, J. Process for enzymatically degumming vegetable oil. European Patent 0654527 (1994).

[69]. Erickson, D. R., Degumming and Lecithin Processing and Utilization, in Practical Handbook Soybean Processing and Utilization, edited by D. R. Erickson, AOCS Press, Champaign, 1995, 174-183.

[70]. van Nieuwenhuyzen, W. Lecithin production and properties. J. Am Oil Chem Soc. 1976, 53, 425-427.

[71]. Scholfield, C. R. Composition of soybean lecithin. J. Am Oil Chem Soc. 1981, 58, 889-892.

[72]. Lundberg, B., Svens, E., Ekman, S. The hydration of phospholipids and phospholipid-cholesterol complexes. Chem. Phys. Lipids. 1978, 22, 285-292.

[73]. McIntosh, T. J., Magid, A. D. Phospholipid Hydration. In Phospholipids Handbook; Cecv, G., Ed.; Marcel Dekker, Inc: New York, N.Y., USA. 1993, 553-577.

[74]. Suetsugu, S., Kurisu, S., Takenawa, T. Dynamic Shaping of Cellular Membranes by Phospholipids and Membrane-Deforming Proteins. Physiological Reviews. 2014, 94, 1219-1248.

[75]. Hernández, E., Quezada, N., in: F. D. Gunstone (Ed.), Phospholipid Technology and Applications, The Oily Press, Bridgwater (UK) 2008.

[76]. Davis, H. T. Factors determining emulsion type. Colloids Surfaces A: Physicochem. Eng. Aspects. 1994, 91, 9-24.

[77]. American lecithin company guide to use and select lecithins and phospholipids. (2020) Available online at: http://phosal.com/lecithin_2009.pdf.

[78]. Alberts, B., Johnson, A., Lewis J. et al. Molecular Biology of the cell. 4th ed. New York: Garland Science 2002.

[79]. Gould, S. B. Membranes and evolution. Curr. Biol. 2018, 28, 381-385.

[80]. Bloom, M., Evans, E., Mouritsen, O. G. Physical properties of the fluid lipid-bilayer component of cell membranes: a perspective. Q. Rev. Biophys. 1991, 24, 293-397.

[81]. De Kroon, A. I. P. M., Rijken, P. J., De Smet, C. H. Checks and balances in membrane phospholipid class and acyl chain homeostasis, the yeast perspective. Prog. Lipid Res. 2013, 52, 374-394.

[82]. Duarte Martino, H. S., Dos Santos Dias, M. M., Noratto, G., Talcott, S., Mertens-Talcott, S. U. Anti-lipidaemic and anti-inflammatory effect of açai (*Euterpe oleracea* Martius) polyphenols on 3T2-L1 adipocytes. Journal of Functional Foods. 2016, 23, 432-443.

[83]. He, J., Giusti, M. M. Anthocyanins: Natural colorants with health-promoting properties. Annual Review of Food Science and Technology. 2010, 1, 163-187.

[84]. Ghasemazedeh, A., Ghasemzadeh, N. Flavonoids and phenolic acids: Role and biochemical activity in plants and human. Journal of Medicinal Plants Research. 2011, 5, 6697-6703.

[85]. Kajiya, K., Hojo, H., Suzuki, M., Nanjo, F., Kumazawa, S., Nakayama, T. Relationship between antibacterial activity of (+)-catechin derivatives and their interaction with a model membrane. J. Agric. Food Chem. 2004, 52, 1514-1519.

[86]. Sirk, T. W., Brown, E. F., Sum, A. K., Friedman, M. Molecular dynamics study on the biophysical interactions of seven green tea catechins with lipid bilayers of cell membranes. J. Agric. Food. Chem. 2008, 56, 7750-7758.

[87]. Yu, X., Chu, S., Hagerman, A. E., Lorigan, G. A. Probing the interaction of polyphenols with lipid bilayers by solid-state NMR Spectroscopy. J. Agric. Food Chem. 2011, 59, 6783-6789.

[88]. Kajiya, K., Kumazawa, S., Naito, A., Nakayama, T. Solid-state NMR analysis of the orientation and dynamics of epigallocatechin gallate, a green tea polyphenol, incorporated into lipid bilayers. Magn. Reson. Chem. 2008, 46, 174-177.

[89]. Phan, H. T. T., Yoda, T., Chahal, B., Morita, M., Takagi, M., Vestergaard, C. Structure-dependent interactions of polyphenols with a biomimetic membrane system. Biochim. Biophys. Acta Biomembr. 2014, 1838, 2670-2677.

Example 3: Lipid Surfactants Induce Anthocyanin Depletion in Cranberry Juice Abstract Our experiments revealed that the addition of lecithin to anthocyanin-rich juices induced a pigmented precipitate. The objective of this example was to determine which surfactants interact with anthocyanins in cranberry juice. Interactions were tested by adding 0.01 M surfactant to single-strength 100% cranberry juice reconstituted from concentrate and mixed thoroughly. The anthocyanin content remaining in the supernatant was examined using pH differential method after centrifugation. We found that most of the surfactants had little or no effect on anthocyanins relative to lecithin. Addition of 1% lecithin to cranberry juice (w/v) depleted anthocyanins up to 73.1±2.2% via precipitation. In addition, the extent of precipitation was related to lecithin hydrophilic-lipophilic balance (HLB) values and individual phospholipids. At low w/v % lecithin, HLB was directly proportional to depletion of juice anthocyanins ($R^2=0.6808$). The individual phospholipids in lecithin also showed different degree of anthocyanin depletion possibly due to their differences in hydrophilicity. Phosphatidylinositol (PI), the most hydrophilic phospholipid, depleted 41.4±8.5% of the anthocyanins via precipitation, which is significantly higher than phosphatidylethanolamine (PE) and phosphatidylcholine (PC). Thus, these results indicate that lecithin and other phospholipids have a unique ability among surfactants to precipitate fruit juice anthocyanins from aqueous systems.

Introduction

Lecithin is a natural surfactant that is commonly used in food industry. It acts as an excellent emulsifier in ice cream, chocolate, and butter [1]. Soybean is a predominant source of lecithin. Commercial soy lecithin is a complex mixture of 65-75% phospholipids, 35% triglycerides and smaller amounts of other substances containing carbohydrates, pigments, sterols, and sterol glycosides [2]. The amphiphilic nature of the phospholipid constituents is responsible for its emulsification ability [3, 4]. Current studies have focused on lecithin-stabilized o/w and w/o emulsions and on the effects of phospholipid composition on those properties [5-7]. Using lecithin as an emulsifier, we examined its efficacy in stabilizing the pigments under the presence of seed oils in grape and cranberry juice. Surprisingly, instead of stabilizing, we discovered that lecithin induced precipitation and led to the depletion of anthocyanins in both systems.

Since the composition of cranberry juice is well studied and has a relatively simple anthocyanin profile compared to grape juice [8], cranberry juice is used in this example. The objective was to investigate how different types of surfactants interact with anthocyanins in cranberry juice. To show how polar surfactants interact with the juice anthocyanins, surfactants with varying HLB values were added to cranberry juice at room temperature. We then assessed the anthocyanin content of the juice supernatant. The resulting anthocyanin depletion was used to compare the effects of different surfactants on anthocyanins.

Materials and Methods

Reagents

Unless specified otherwise, the lecithin employed was soybean lecithin powder (Product No. J61675, Alfa Aesar, Ward Hill, Mass., U.S.A.). Other lecithins were from Cargill (Wayzata, Minn., U.S.A.) and included: standardized, liquid soy lecithin (Topcithin® 100); de-oiled, powdered soy lecithin (Emulpur® N); enzymatically hydrolyzed, liquid soy lecithin (Emulfluid® E); acetylated soy lecithin (Emulfluid® A); de-oiled, enzymatically hydrolyzed, powdered soy lecithin (Lecimulthin® 150 IP); hydroxylated, liquid lecithin (Emulfluid® HL 66). Span® 65, polyglyceryl 6 dioleate (99% purity), oleic acid (99% purity), 1-stearoyl-rac-glycerol (99% purity), sodium oleate (99% purity), sorbitan monostearate, polysorbate 60, 1-oleoyl-rac-glycerol (99% purity), triglycerol monostearate, phosphatidylcholine (EP standard), and sodium acetate trihydrate (ACS grade) were from Sigma-Aldrich (St. Louis, Mo., U.S.A.). Potassium chloride (ACS certified), hydrochloric acid (ACS certified), monolaurin (98% purity) and sucrose stearate were from Thermo Fisher Scientific (Waltham, Mass., U.S.A.). L-α-phosphatidylethanolamine from soy (99% purity) and L-α-phosphatidylinositol from soy (99% purity) were from Avanti Polar Lipids (Alabaster, Ala., U.S.A.). Ultrapure grade water was purified to at least 18.1 M Ω·cm using a Barnstead water filtration system (Thermo Fisher Scientific). All reagents were used without further purification except as noted.

Diluted Cranberry Juice Preparation

Classic Mash Cranberry Juice Concentrate with essence returned was received frozen from the supplier (Ocean Spray Cranberries Inc., Lakeville-Middleboro, Mass., U.S.A.). The concentrate came at 50.0° Brix from manufacturer. It was immediately thawed, aliquoted and stored at −20° C. until use. Prior to experiment use, the concentrate was thawed, brought to room temperature, and diluted to 7.5° Brix according to the manufacture specification. The average diluted juice pH was measured at 2.43.

Combining Surfactants or Lecithin with Juice Samples

Individual surfactants/phospholipids were added to 10 mL juice samples at a final concentration of 0.01 M. Varying amounts of lecithin were added to 10 mL juice samples at 0.05, 0.1, 0.5, 1, 2, 3, 4, or 5% w/v. Lecithin with different HLB values were added to 10 mL juice samples at 1, 2, 3, 4, or 5% w/v. All mixtures were then vortexed for 3 min and then centrifuged at 3220×g for 20 min. The centrifugation step was repeated with the supernatants. All procedures were carried out at ambient temperatures unless otherwise specified.

Determination of pH

Juice pH was measured using a Seven Compact pH/Ion meter S220 (Mettler Toledo, Columbus, Ohio, U.S.A.).

Monomeric Anthocyanin Analysis

Monomeric anthocyanin (MA) content was determined by the AOAC pH differential method [9]. Samples were placed in 96-well plates (Thermo Scientific) for spectral acquisition using a SpectraMax Plus Microplate Reader (Molecular Devices, Sunnyvale, Calif., U.S.A.). We used the SoftMax Pro 5.4.4 to scale for pathlength (Molecular Devices, Sunnyvale, Calif., U.S.A.). Juice samples were diluted such that the absorbance at 520 nm was within the linear range of the instrument. Triplicate samples were analyzed, and the average values are reported. MA content was expressed as cyanidin-3-glucoside equivalents for all juices using Eq. (1), where MW is the molecular weight of cyanidin-3-glucoside, 449.2 g/mol; DF is a dilution factor; E is the molar extinction coefficient of cyanidin-3-glucoside in aqueous buffer of pH 1.0, 26900 L/mol/cm; and b is the corrected pathlength of 1 cm.

$$MA = \frac{[(ABS_{520\,nm} - ABS_{700\,nm})_{pH\,1.0} - (ABS_{520\,nm} - ABS_{700\,nm})_{pH\,4.5}] \times MW \times DF \times (10^3 \text{ mg/g})}{\varepsilon \times b}$$

Percent Depletion

The depletion of MA expressed as a percent was determined according to the following equation:

$$\% \text{ depleted} = \frac{MA_{control} - MA_{lecithin\,treated}}{MA_{control}} \times 100$$

Statistical Analysis

The mean and standard error of each treatment were calculated from triplicates. Analysis of variance (ANOVA) was carried out to determine any significant differences between treatments (P<0.05).

Results

Interaction of Anthocyanins by Individual Surfactants/Lecithins

The cranberry juice samples were treated with the surfactants at 0.01 M individually and the anthocyanin content was measured before and after the treatment to study the effect of the surfactants on anthocyanins. The percentage difference was expressed in % depletion (Table 2). Surfactants such as oleic acid, glycerol dioleate, sorbitan tristearate, glycerol monooleate, glycerol monostearate, sorbitan monostearate, sodium stearoyl lactylate, glycerol monolaurate, triglycerol monostearate, hexaglycerol dioleate, sodium oleate, sucrose stearate, sodium dodecyl sulfate and polysorbate 60 had no significant changes in percentage depletion (P>0.05). However, by one-way ANOVA, two types of lecithins significantly depleted the anthocyanins and showed greater depletion ability compared to the other surfactants. Lecithin from Bob's Red Mill depleted 70.7±1.1% of anthocyanins, which was significantly higher than 30.8±1.4% depleted by lecithin from Alfa Aesar compared by one-way ANOVA.

Pigments Precipitation Induced by Lecithin

Figure 9:
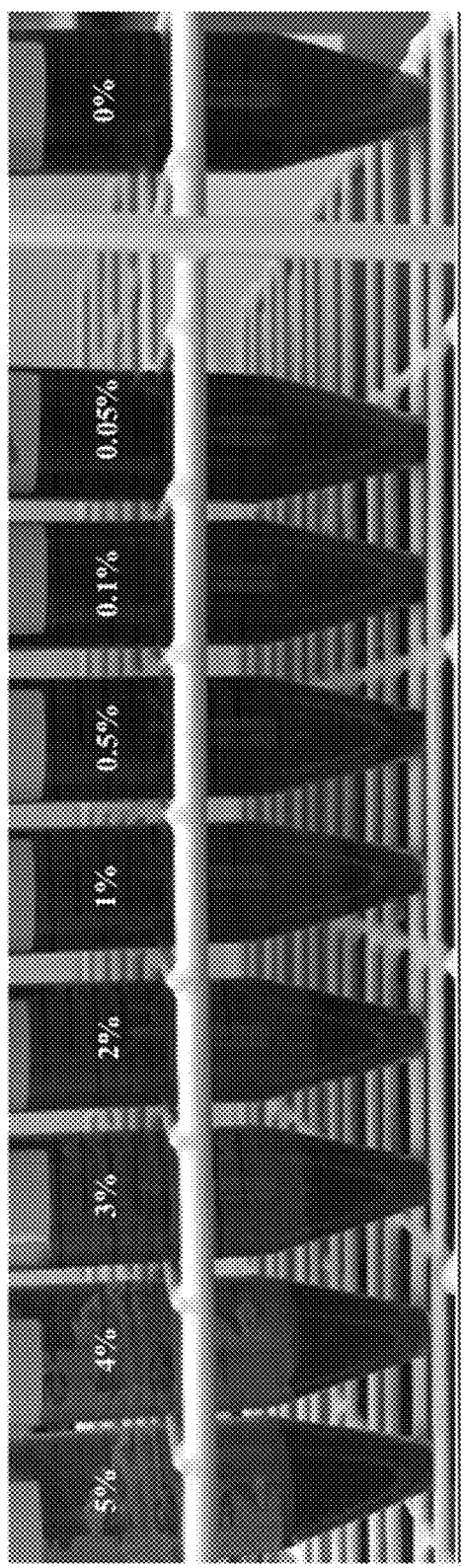
FIG. 9. Precipitation of pigments from 100% cranberry juice with powdered lecithin (0.05% to 5% w/v) after centrifugation.

When lecithin was mixed with cranberry juice, it induced precipitation of pigmented polyphenols. FIG. 9 illustrates the precipitation of polyphenols in cranberry juice over the range of 0.05% to 5% w/v lecithin. When more lecithin was introduced into the juice, the pellet containing lecithin and trapped polyphenols increased in size and an obvious color loss could be observed in the supernatant. When lecithin was added to water in the same manner, no precipitate was observed.

TABLE 2

Depletion of monomeric anthocyanins by 0.01M surfactants in diluted cranberry juice[1]

| HLB value | Surfactant | Depletion % |
|---|---|---|
| 1 | oleic acid | 0.021 ± 1.28[f, e] |
| 1.9 | glycerol dioleate | 2.10 ± 0.92[e, d, c] |
| 2.1 | sorbitan tristearate (Span 65) | 2.85 ± 2.50[e, d, c] |
| 3.4 | glycerol monooleate | 0.69 ± 1.85[f, e] |
| 3.8 | glycerol monostearate | 6.21 ± 0.90[e] |
| 4.7 | sorbitan monostearate | 2.38 ± 1.31[e, d, c] |
| 5.1 | sodium stearoyl lactylate | 0.27 ± 2.4.5[f, e] |

TABLE 2-continued

Depletion of monomeric anthocyanins by 0.01M surfactants in diluted cranberry juice[1]

| HLB value | Surfactant | Depletion % |
|---|---|---|
| 5.2 | glycerol monolaurate | −2.37 ± 1.25[f] |
| 7 | triglycerol monostearate | 0.21 ± 0.35[f, e] |
| 9 | hexaglycerol dioleate | 4.88 ± 1.26[d, c] |
| 14.9 | polysorbate 60 | 0.14 ± 2.97[f, e] |
| 18 | sodium oleate | −4.22 ± 1.01[f] |
| 20 | sucrose stearate | −2.20 ± 2.47[f] |
| 40 | sodium dodecyl sulfate | 2.04 ± 1.43[e, d, c] |
| NA | soy lecithin (Bob's Red Mill) | 70.7 ± 1.1[a] |
| NA | lecithin from soybean (Alfa Aesar) | 30.8 ± 1.4[b] |

[1]Data are reported as means ± SD, n = 3 or greater. By one-way ANOVA, the percentage depletion by two types of lecithins was significantly greater than the other surfactants (P < 0.0001).

Depletion of Anthocyanins by Various Lecithins

Figure 10:
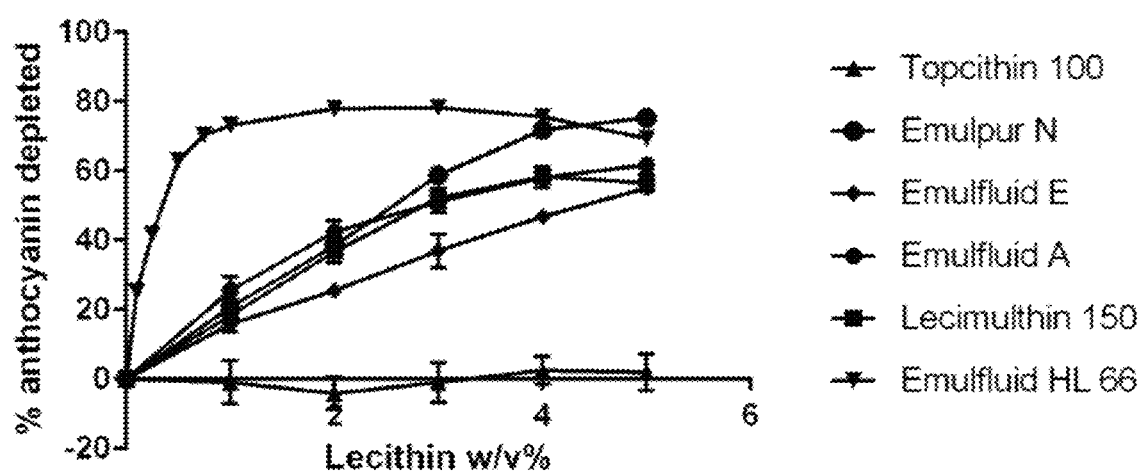
FIG. 10. Soy lecithins deplete monomeric anthocyanin in cranberry juice.

Lecithins with HLB values from 3 to 9 were added to cranberry juice to further evaluate interactions with anthocyanins (Table 3). The dose responses for anthocyanin depletion in juice was evaluated at 0, 1, 2, 3, 4, 5 w/v % for lecithins (FIG. 10). At 1% w/v, lecithins with HLB values of 4 to 9 reduced monomeric anthocyanin content by >15%. Emulfluid® E, Lecimulthin® 150 IP, Emulpur® N, Emulfluid® A, Emulfluid® HL 66 were able to deplete 15.8±1.8%, 18.5±4.6%, 20.8±2.2%, 25.7±4.1% and 73.1±2.2% of anthocyanins from the cranberry juice. Topcithin® 100 the most hydrophobic lecithin investigated, did not deplete cranberry juice anthocyanin content significantly. Emulfluid® HL 66, had the highest HLB value at 9 and depleted 73.1±2.2% of anthocyanins at 1% w/v. Among all lecithins with defined HLB values, it depleted the most juice anthocyanins at every percentage level from 1 to 3 w/v % (P<0.0001).

Linear Relationship Between Percentage Anthocyanin Depletion and HLB Values

Figure 11:
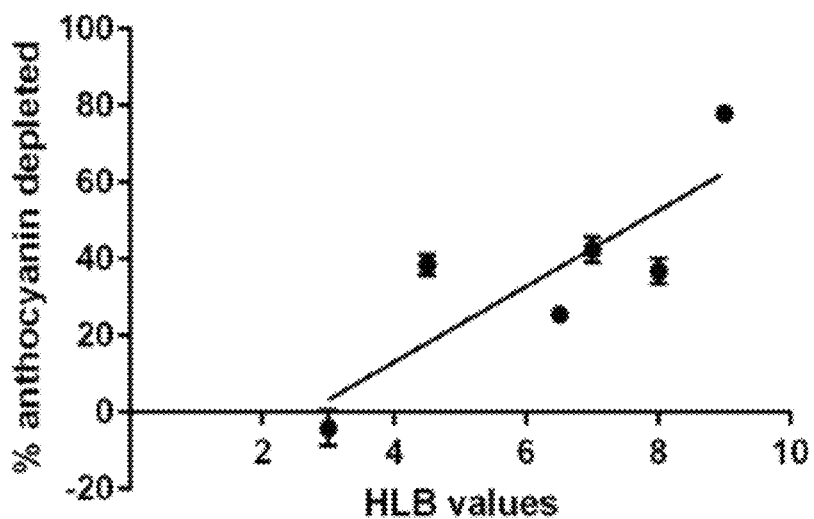
FIG. 11. Scatter plot and the corresponding regression line for the relationship between the dependent variable % MA depleted and the independent variable HLB values at (a) 2% w/v lecithin (b) 5% w/v lecithin.
Figure 11:
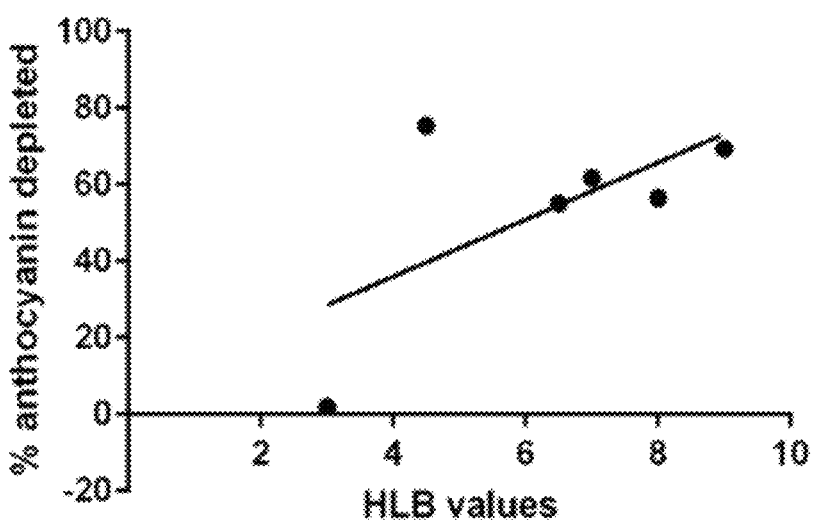

The linear relationships between HLB values and percentage monomeric anthocyanin depletion at two concentrations are illustrated in FIG. 11. At 2% w/v lecithin addition, the HLB value was positively associated with anthocyanin loss in solution (R2=0.6808). However, at 4% w/v lecithin was treated with the diluted cranberry juice, and the impact of differing HLB values was minimized (R2=0.3977).

TABLE 3

Depletion of monomeric anthocyanins by 1% w/v lecithin in cranberry juice[1]

| HLB value | Lecithin type | Depletion % |
|---|---|---|
| 3 | Topcithin ® 100 | −0.98 ± 6.20[a] |
| 4-5 | Emulpur ® N | 20.8 ± 2.20[b, c] |
| 6-7 | Emulfluid ® E | 15.8 ± 1.77[b] |
| 7 | Emulfluid ® A | 25.7 ± 4.05[c, d] |
| 8 | Lecimulthin ® 150 IP | 18.5 ± 4.64[b, c] |
| 9 | Emulfluid ® HL 66 | 73.1 ± 2.21[e] |
| NA | soy lecithin (Bob's Red Mill) | 70.7 ± 1.08[e] |
| NA | lecithin from soybean (Alfa Aesar) | 30.8 ± 1.38[d] |

[1]Depletion %, percentage depletion of monomeric anthocyanin. The values are reported as means ± SD, n = 3 or greater. By one-way ANOVA and Tukey's multiple comparison test of various types of lecithins bearing different letters, P < 0.0001 for percentage monomeric anthocyanin depletion.

Depletion of Anthocyanins by Individual Phospholipids

Because lecithin depleted anthocyanins from cranberry juice, we next investigated the effect of the main phospholipids in commercial soy lecithin (Table 4). Purified PC, PE, and PI from soy at 0.01 M was added to the cranberry juice samples and the polyphenol depletion was precipitated in the pellet. PC, the most hydrophobic phospholipid, induced 6.69±3.57% of anthocyanin loss from the cranberry juice. PE depleted the juice anthocyanins by 10.4±2.5%. There were no significant differences between PC and PE. PI exhibited the most depleting power and significantly depleted 41.4±8.5% of the anthocyanins in cranberry juice.

TABLE 4

Depletion of monomeric anthocyanins by 0.01M phospholipid in lecithin[1,2]

| Charge | ID | Surfactant | HLB value | Depletion % |
|---|---|---|---|---|
| (+/−) | PC | Phosphatidyl-choline (soy) | 27.1 | 6.69 ± 3.6[b] |
| (+/−) | PE | Phosphatidyl-ethanolamine (soy) | 17.7 | 10.4 ± 2.5[b] |
| (−) | PI | L-α-phosphatidyl-inositol (soy) | 27.2 | 41.4 ± 8.5[a] |

[1]Depletion %, percentage depletion of monomeric anthocyanin. The values are reported as means ± SD, n = 3 or greater. Different superscript letters in the same column indicate significant difference in the mean ($P < 0.05$).
[2]HLB value is calculated using ChemDraw software packages (v 16.0)

Discussion

Hydrophilic-lipophilic balance (HLB) is used as a measure of the degree to which a surfactant is hydrophilic or lipophilic, calculated based on the chemical groups of the molecule described by Davis, J T [10]. On a scale of 0-40, surfactants with higher HLB value indicates their increased hydrophilicity. We hypothesized that surfactants with HLB values similar to lecithin would affect the interactions with the anthocyanins in cranberry juice. However, no significant differences were seen between the percentage depletion among the surfactants with HLB values in the range of 1-40, except lecithins Other surfactants did not induce anthocyanin loss to the extent as soy lecithin. Soy lecithins, on the contrary, interact with the juice anthocyanins and deplete them via precipitation. The interaction between soy lecithins and juice anthocyanins takes place in two stages. First, soy lecithins are dissolved rapidly when they are in contact with the aqueous. Then, the dissolved lecithins react with the juice anthocyanins, which appears to be the rate limiting step.

On the basis of these results, we surmise that lecithin and fruit juice anthocyanins precipitate by forming unstable lipid bilayers that form spontaneously when lecithin dissolves in cranberry juice. The major phospholipid components in lecithin are phosphatidylcholine (PC), phosphatidylethanolamine (PE), and phosphatidylinositol (PI) and phosphatidic acid (PA) [11]. The headgroups of these phospholipids contains negatively charged phosphate groups. It is possible that the positively charged anthocyanins interact with the negatively charged phosphate headgroup on lipid bilayer through ionic interactions. The formation of the phospholipid-anthocyanin complexes aggregates, and the increased density and size leads to precipitation. A similar mechanism was suggested by Bonarska-Kujawa et al. [12]. This group characterized the location of the phospholipid-anthocyanin interaction on cell membranes using microscopy. The anthocyanins were incorporated into erythrocytes and modified the membrane surfaces. The anthocyanin compounds were found mainly aggregated on the outer layer of the membrane and did not permeate to the inner layer of the membrane [13].

Hydrophilicity of the lecithins also impacted the percentage anthocyanin depletion. Soy lecithins obtained from Cargill were modified to enhance their functionality. They have different hydrophilicity, in the range of 3-9. Topcithin® 100, the least hydrophilic one, is the standardized, liquid soy lecithin. It is a mixture of non-polar triglycerides and molar phospholipids. Emulfluid® E and Lecimulthin® 150 IP contain hydrolyzed lecithin and are made more hydrophilic by removing one fatty acid tail enzymatically. The only difference between these two is that Lecimulthin® 150 IP is composed mainly of polar phospholipids and lysophospholipids. Emulfluid® A contains acetylated phosphate headgroups and has an HLB value of 7. It is a mixture of non-polar triglycerides and polar phospholipids. The most hydrophilic lecithin, Emulfluid® HL 66, is modified to have hydroxyl groups on the fatty acid tails and it is a mixture of triglycerides and phospholipids as well. Our results showed that the increase in hydrophilicity of the lecithins by modification on chemical structures of soy lecithins enhanced the interaction with the anthocyanins at lower lecithin concentration. According to Carlsson, lecithins with high HLB values exhibit the best properties as emulsifying agents [14]. The modification enhances the interaction between the phospholipids and juice anthocyanins.

The results of individual phospholipids also suggest the importance of hydrophilicity of the lecithins. These phospholipids have distinctive headgroups yet similar fatty acid composition. The HLB values of PC, PE and PI are calculated to be 27.1, 17.7 and 27.2 by ChemDraw. Compared to PC and PE, PI showed greatest depletion ability due to its highest hydrophilicity. We expect PC to exhibit high percent depletion because it has similar HLB value as PI. However, the percent anthocyanin depleted by PC is significantly lower than PI. The positive charge on PC and PE might create an electrostatic hindrance to prevent the anthocyanins from interacting with the phosphate group and thus causes less percentage depletion of the anthocyanins.

To summarize, surfactants of different polarity did not interact with anthocyanins significantly as we expected. However, lecithin, due to its unique phospholipid bilayer and charged headgroups, had a destabilizing effect that accumulated anthocyanins in the precipitate. The strong interaction demonstrates a promising future direction using lipid surfactants to either protect unstable anthocyanins from degradation and modified anthocyanin absorption and bioavailability after consumption.

Conclusion

Among a variety of surfactants, lecithin depleted anthocyanins from cranberry juice. The destabilizing effect of soy lecithin in cranberry juice is related to the individual phospholipids that lecithin is composed of and the hydrophilic-lipophilic nature of the lecithin.

REFERENCES

[1]. Wu, Y., Wang, T. Soybean Lecithin Fractionation and Functionality. J. Am Oil Chem Soc. 2003, 80, 319-326.
[2]. Scholfield, C. R. Composition of soybean lecithin. J. Am Oil Chem Soc. 1981, 58, 889-892.
[3]. Krog, N. J. Food Emulsifiers and Their Chemical and Physical Properties. in Food Emulsions, edited by S. E. Friberg and K. Larsson, Marcel Dekker, New York, 1997, 141-188.
[4]. Nyankson, E., DeCuir, M. J., Gupta, R. B. Soybean lecithin as a dispersant for crude oil spills. ACS Sustainable Chem. Eng. 2015, 3, 920-931.
[5]. Larsson, K. Stability of Emulsions Formed by Polar Lipids. Prog. Chem. Fats Other Lipids. 1987, 16, 163-169.

[6]. Weete, J. D., Betageri, S., Griffith, G. L. Improvement of Lecithin as an Emulsifier for Water-in-Oil Emulsions by Thermalization. J. Am. Oil Chem Soc. 1994, 71, 731-737.

[7]. Johansson, D., Bergenstahl, B. Lecithins in Oil-Continuous Emulsions—Fat Crystal Wetting and Interfacial Tension. Ibid. 1995, 72, 205-211.

[8]. Mullen, W., Marks, S., Crozier, A. Evaluation of phenolic compounds in commercial fruit juices and fruit drinks. J. Agri. Food Chem. 2007, 55, 3148-3157.

[9]. Lee, J., Durst, R. W., Wrolstad, R. E. Determination of Total Monomeric Anthocyanin Pigment Content of Fruit Juices, Beverages, Natural Colorants, and Wines by the pH Differential Method: Collaborative Study. Journal of AOAC International. 2005, 88, 1269-1278

[10]. Davis, J. T. Factors determining emulsion type: Hydrophile-lipophile balance and beyond. Colloids and Surfaces. 1994, 91, 9-24.

[11]. Scholfield, C. R. Composition of Soybean Lecithin. Journal of AOAC Society. 1981, 58, 889-892.

[12]. Bonarska-Kujawa, D., Pruchnik, H., Kleszczyńska, H. Interaction of selected anthocyanins with erythrocytes and liposome membranes. Cell. Mol. Biol. Lett. 2012, 17, 289-308.

[13]. Krishna, G., Wood, G. C., Sheth, B. B. Improving emulsification efficacy of lecithin by formulation design, I: Effect of adding a secondary surfactant. PDA. J. Pharm. Sci. Technol. 1998, 52, 331-336.

[14]. Carlsson, A., in: F. D. Gunstone (Ed.), Phospholipid Technology and Applications, The Oily Press, Bridgwater (UK) 2008.

Example 4: Phospholipid Interaction with Polyphenols in Aqueous Systems

Abstract

The objective of this example is to show the type of polyphenols that interact with soy lecithin. Single-strength cranberry juice from concentrate was treated with lecithin and the anthocyanin and non-anthocyanin polyphenols depleted from the aqueous phase were determined. Anthocyanins were determined by the pH differential method, total phenols by the Folin method, and proanthocyanidin by the 4-dimethylaminocinnamaldehyde (DMAC) method. The dose response of 1 to 4% w/v lecithin addition depleted non-anthocyanin and anthocyanin polyphenols by 17.6-79.8%. The maximum amount of polyphenols depleted was 79.8±0.3% with 5% w/v powder lecithin. Next, we show various types of polyphenols that interact with lecithin by preparing individual polyphenols in aqueous solutions pH 2.43, and treating the polyphenol solutions with 1% w/v powdered soy lecithin. HPLC analysis was used to determine the extent of polyphenol depletion from solution. We hypothesized that polyphenols interact differently with the phospholipids depending on the physical properties of the polyphenols. Lecithin precipitated anthocyanins, quercetin-3-O-galactoside, catechin, genistein, quercetin and resveratrol, depleting 10.1±6.3% to 71.8±1.8% from solution. We expect that the hydrophobicity of the polyphenol, phenolic hydroxyl groups and the structural geometry are characteristic features that induce precipitation of lecithin-polyphenol complexes in aqueous solutions. Furthermore, the results suggest that the interaction extends beyond just anthocyanins and fruit juices. A complete juice matrix is not required for lecithin-polyphenol precipitation.

Introduction

In literature, many studies have used phospholipid liposomes to encapsulate anthocyanins and other polyphenols to improve their stability and bioavailability [1-5]. In the prior example, we discovered that lecithin effectively depletes cranberry juice anthocyanins by precipitation. The underlying nature of this phenomenon is still unclear, as little attention has been given to direct phospholipid-polyphenol interactions. Other polyphenols may also interact with lecithin and lead to precipitation. Characterizing these additional interactions are of importance in clarifying if lecithin selectively extracts polyphenols from aqueous systems.

Therefore, the objective of this example was to characterize types of polyphenols in cranberry juice and from non-juice aqueous systems that interact with lecithin. We added lecithin to cranberry juice and individual polyphenols in aqueous solutions to determine the types of polyphenols precipitated by lecithin. The composition of the residual polyphenols from these systems were determined by the pH differential assay for anthocyanins, the Total Phenols assay, the DMAC assay for proanthocyanidins, and by HPLC analysis. Purified rutin (quercetin-3-O-rutinoside, quercetin-3-O-galactoside, catechin, gallic acid, genistein, quercetin and resveratrol, were examined to determine the molecular features of polyphenols that lead to lecithin precipitation.

Materials and Methods

Reagents

Unless specified otherwise, the lecithin employed was soybean lecithin powder (Product No. J61675, Alfa Aesar, Ward Hill, Mass., U.S.A.). Quercetin dihydrate (97% purity) was from Alfa Aesar (Ward Hill, Mass., U.S.A.). Potassium chloride (ACS certified), acetic acid (ACS certified), methanol (HPLC grade), ammonium formate (ACS certified), and hydrochloric acid (ACS certified) were from Thermo Fisher Scientific (Waltham, Mass., U.S.A.). Gallic acid monohydrate (ACS reagent grade) and rutin (≥97% purity) was from Acros Organics (Morris Plains, N.J., U.S.A.) (+)-Catechin hydrate (98% purity), genistein (98% purity), and trans-resveratrol (98% purity) were obtained from Cayman Chemical (Ann Arbor, Mich., U.S.A.). Quercetin-3-galactoside (≥98% purity) was from Extrasynthese (Genay, France). Sodium acetate trihydrate (ACS grade), sodium bicarbonate (BioReagent), Folin & Ciocalteu's phenol reagent, 4-(Dimethylamino) cinnamaldehyde, formic acid (reagent grade, ≥95%), and acetone (ACS reagent grade) were purchased from Sigma-Aldrich (St. Louis, Mo., U.S.A.). Ethanol (anhydrous, USP standard) was from Decon Labs (King of Prussia, Pa., U.S.A.). Ultrapure grade water was purified to at least 18.1 M S2 cm using a Barnstead water filtration system (Thermo Fisher Scientific). All reagents were used without further purification except as noted.

Diluted Cranberry Juice Preparation

Single-strength cranberry juice was prepared freshly from frozen juice concentrates as described in Example 3.

Combining Lecithin with Juice Samples

Lecithin was added to 10 mL juice samples (pH ~2.43) at 1, 2, 3, 4, or 5% w/v. The mixture was then vortexed for 3 min and then centrifuged at 3220×g for 20 min to pellet the precipitate. The centrifugation step was repeated with the supernatants. All procedures were carried out at ambient temperatures unless otherwise specified.

Combining Lecithin with Solutions Containing Polyphenols or Phenolic Acids

Aqueous polyphenol solutions near saturation were prepared by dissolving the individual polyphenols in 50 mL ultrapure water. Depends on their solubility in water, the polyphenols solutions were made in different concentrations. Solutions containing rutin (quercetin-3-O-rutinoside), quercetin, genistein, quercetin-3-O-galactoside, gallic acid, resveratrol, (+)-catechin were prepared at 0.5 ug/mL, 0.5 ug/mL, 2.0 ug/mL, 28 ug/mL, 30 ug/mL, 15 ug/mL, 70 ug/mL, respectively. The pH of the solution was then adjusted to ~2.43 using 6 M HCl in order to approximate the pH of juice. The adjusted solution was centrifuged at 3220×g for 20 min to remove any undissolved solids. Next, 1% w/v lecithin was added to 10 mL of the supernatant containing the polyphenols or the phenolic acids. The mixture was vortexed for 1 min and then centrifuged at 3220×g for 20 min to pellet any precipitate. The supernatant was transferred to a 2 mL microcentrifuge tube and was centrifuged for another 20 min at 21130×g before HPLC analysis.

Determination of pH

Juice pH was measured using a Seven Compact pH/Ion meter S220 (Mettler Toledo, Columbus, Ohio, U.S.A.).

Monomeric Anthocyanin Analysis

Monomeric anthocyanin (MA) content was determined by the AOAC pH differential method as described in Example 3 [6].

Percent Depletion

The depletion of individual polyphenol content expressed as a percent was determined according to the following equation:

$$\% \text{ depleted} = \frac{\text{Concentration}_{before} - \text{Concentration}_{after\ lecithin\ treated}}{\text{Concentration}_{before}} \times 100$$

Total Phenol Content

Total Phenols content was determined spectrophotometrically by the Folin-Ciocalteu assay using method developed by Singleton, Orthofer and Lamuela-Raventos [7]. A 10.00 μL of diluted juice, ultrapure water as a blank, or gallic acid standard solutions were mixed with 173.0 μL of ultrapure water in each well on a 96-well plate (Thermo Scientific), followed by 15.0 μL Folin-Ciocalteu reagent. After incubating for 5 min, 45.0 μL of 20% w/v sodium bicarbonate solution and 57.0 μL of ultrapure water were added subsequently. The solutions were mixed thoroughly, and the plate was incubated at room temperature in the dark for 1 h. After incubation, the absorbance of the samples was measured at 765 nm using a SpectraMax Plus Microplate Reader (Molecular Devices, Sunnyvale, Calif., U.S.A.). Juice samples were diluted such that the absorbance was within the linear range of the instrument. Analysis was performed on triplicate samples. Total phenol content was expressed as gallic acid equivalents based on an external calibration of 16.1-2000 μg gallic acid/mL solutions.

Total Proanthocyanidin Content

Total proanthocyanidin content was determined using the 4-dimethylaminocinnam-aldehyde (DMAC) assay reported by Prior et al. (2010) with minor modification [8]. Aliquots of diluted cranberry juice each of 70.0 μL, ultrapure water as a blank, or (+)-catechin standard solutions were mixed with 210 μL DMAC solution (0.1% w/v in acidic methanol) in a well on a 96-well plate (Thermo Scientific). The absorbance of each sample at 640 nm was recorded every min for 30 min using a SpectraMax Plus Microplate Reader (Molecular Devices, Sunnyvale, Calif., U.S.A.). Juice samples were diluted such that the absorbance was within the linear range of the instrument. Analysis was performed on triplicate samples. Total proanthocyanidin content was expressed as (+)-catechin equivalents based on an external calibration of 1.56-50.0 μg (+)-catechin/mL solution.

HPLC Analysis of Polyphenol or Phenolic Acids Solutions

Polyphenol and phenolic acid content remaining in the supernatant were quantitated by reverse phase HPLC using a Dionex Ultimate 3000 HPLC equipped with an LPG-3400 quaternary pump, a WPS-3000 analytical autosampler, a DAD-3000 diode array detector, and an FLD-3100 fluorescence detector.

Cranberry anthocyanins and purified gallic acid were analyzed using a Kinetex 5 μm EVO C18, 100 A°, 250 mm×4.6 mm column (Phenomenex, Torrance, Calif., U.S.A.). Separation was with formic acid:water (5:95, v/v) (A) and methanol (B). The flow rate was set to 1 mL/min. The gradient was initially 5% B for 1 min, then increased to 35% B over 39 min, from 35% to 95% B over the next 10 min, and held constant at 95% B for 5 min, then decreased to 5% B over 2 min, and re-equilibrated at 5% B for the remaining 8 min. The column oven was set to 30° C. The absorbance was monitored at 254, 280, 370 and 520 nm. The major cranberry anthocyanins cyanidin-3-O-galactocide, cyanidin-3-O-glucocide, cyanidin-3-O-arabinoside, peonidin-3-O-galactocide, peonidin-3-O-glucoside, peonidin-3-O-arabinoside and cyanidin were identified based on known elution order in the 520 nm chromatogram [9]. The gallic acid peaks in the 280 nm chromatogram was quantitated on the basis of authentic external standards.

Supernatants contained the other polyphenol compounds were quantitated using a Kinetex 2.6 μm EVO C18, 100 A°, 50 mm×3.0 mm column (Phenomenex, Torrance, Calif, U.S.A.).

Separation was performed with mobile phase A consisting of 10 mM ammonium formate, 0.3 mM EDTA (pH 3.50) and mobile phase B consisting of 100% methanol. The flow rate was set to 0.5 mL/min. The gradient began at 15% B for 2 min, increased to 90% B over 6 min, then decreased to 15% B over 1 min and re-equilibrated at 15% B for the remaining 1 min. The column oven was set to 25° C. We collected absorbance data at 254, 280, 370 and 520 nm. All the peaks were identified in comparison to authentic external standards.

Statistical Analysis

The mean and standard error of each treatment were calculated from triplicates. Analysis of variance (ANOVA) was carried out to determine any significant differences between treatments ($P<0.05$).

Results

Figure 12:
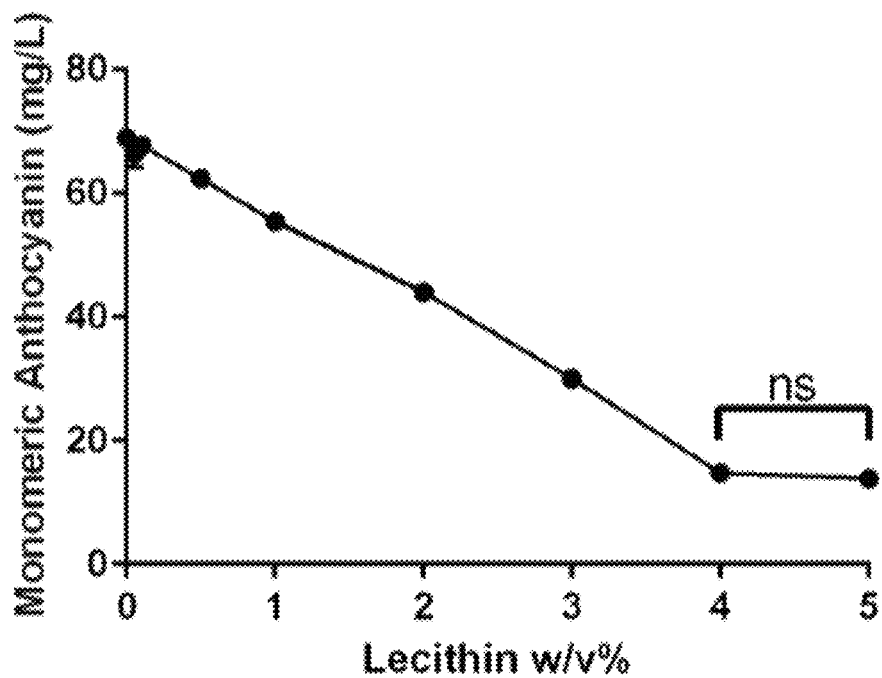
FIG. 12. Monomeric anthocyanin content of the cranberry juice supernatant after lecithin addition.

Depletion of Anthocyanins, Total Phenols, Total Proanthocyanins in Diluted Cranberry Juice The amount of anthocyanin depleted from the juice supernatant was measured after increasing lecithin addition. As the percentage weight increased, anthocyanin content in the supernatant decreased gradually and reached a plateau at 5% w/v (FIG. 12). The addition of 5% lecithin did not significantly deplete more than the 4%, thus the maximum depletion occurred at 4% w/v, where the anthocyanins in cranberry juice was depleted up to 80%.

Figure 13:
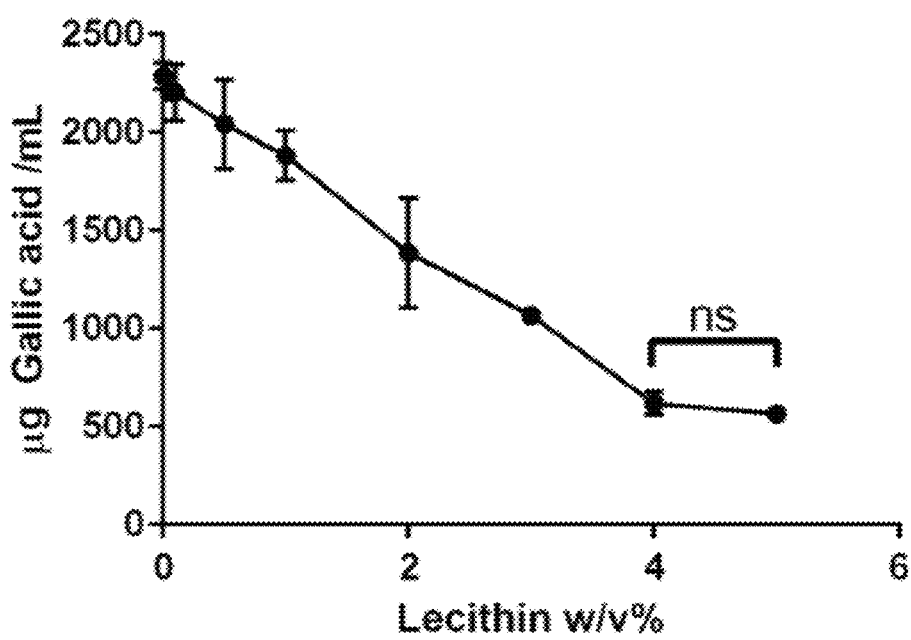
FIG. 13. Total phenol content of the cranberry juice supernatant after lecithin addition.

The Total Phenols value of lecithin-depleted cranberry juice supernatant was inversely proportional to the amount of lecithin added (FIG. 13). The total phenol content decreased consistently as the amount of lecithin increased from 0.5% to 4% w/v. At 3% w/v, lecithin was able to deplete 53.3±1.6% of the total phenols in cranberry juice. The maximum depletion of total phenols was observed at 5%. Up to 75% of the total phenols were depleted. Again, there is no statistical difference in total phenol content using 4% w/v and 5% w/v.

Figure 14:
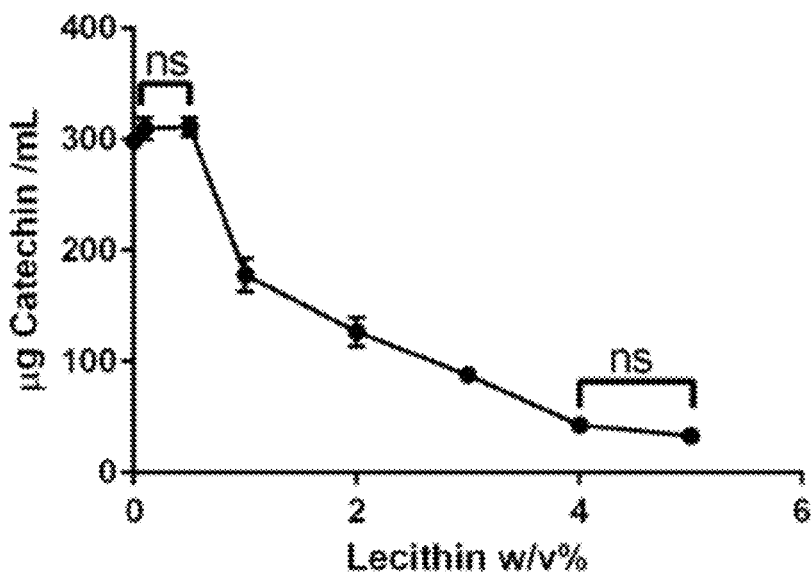
FIG. 14. Total proanthocyanidin content of the cranberry juice supernatant after lecithin addition.

Cranberry juice proanthocyanidins were also depleted by lecithin (FIG. 14). At concentrations of <1% lecithin did not deplete proanthocyanidins from cranberry juice. However, at ≥1% w/v lecithin, lecithin depleted proanthocyanidins from cranberry juice significantly compared to the untreated control. At 5% w/v lecithin, up to 89% of the proanthocyanidins were depleted. There is no statistical difference on the proanthocyanidin depletion between 4% and 5% w/v lecithin.

Lecithin Interaction with Individual Polyphenols

Figure 15:
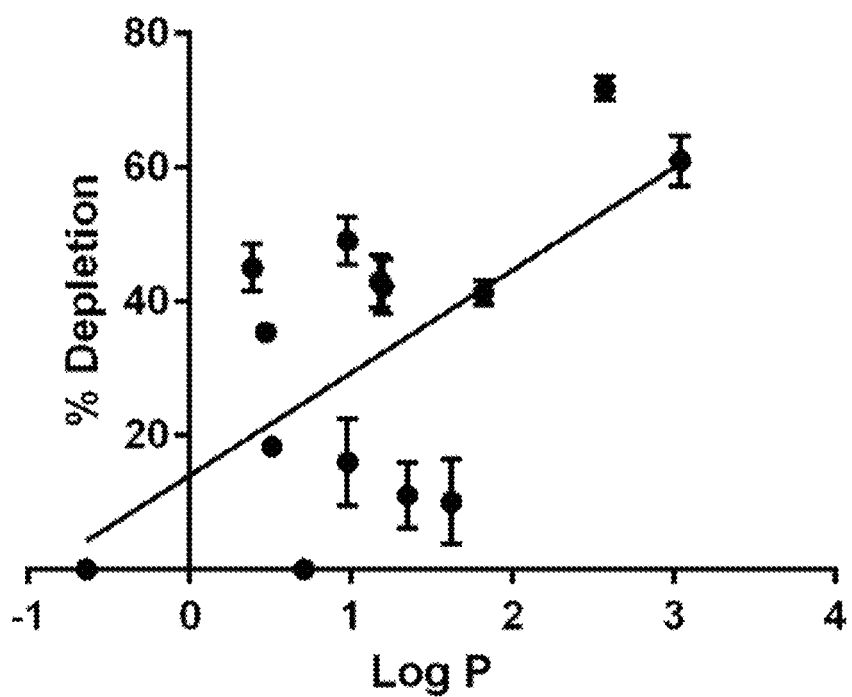
FIG. 15. Scatter plot and the corresponding regression line for the relationship between the dependent variable % depletion and the independent variable Log P values.

Polyphenols with 3' and 4' hydroxylation on the B-ring with Log P values from −0.64 to 3.04 were evaluated for their potential interactions with lecithin (Table 5). Rutin, the most hydrophilic and largest compound tested, did not induce lecithin precipitation. Gallic acid, the smallest compound tested also did not induce precipitation of lecithin. In contrast, the other polyphenols examined had different degrees of interaction with lecithin. Quercetin-3-O-galactoside was depleted moderately by 35.4±1.0%. (+)-Catechin interacted with lecithin slightly and only 18.4±0.5% of it was depleted. The concentration of individual anthocyanins in diluted cranberry juice was analyzed before and after lecithin addition. At 1% w/v lecithin, cyanidin-3-O-galactoside showed maximum depletion, 49.1±3.5%, compared to other anthocyanin compounds. Cyanidin-3-O-glucoside was depleted by 45.0±3.5%. Peonidin-3-O-galactoside and peonidin-3-O-glucoside were depleted by 42.2±4.1% and 43.0±4.0%. Delphinidin-3-O-arabinose, cyanidin-3-O-arabinose and peonidin-3-O-arabinose were depleted by only 11.1±4.9%, 16.0±6.5% and 10.1±6.3%. Genistein, the most hydrophobic compound among the list, showed moderate amount of reduction when treated with lecithin. It was depleted by 61.0±3.8% of the initial genistein in the aqueous solution. Quercetin was depleted by 41.3±1.8%. Resveratrol, a more hydrophobic compound than other polyphenols was depleted by 71.8±1.8% at 1% w/v lecithin. The linear relationship between percentage polyphenol depletion and Log P values was plotted in FIG. 15.

Discussion

Soy lecithin depletes anthocyanin and non-anthocyanin polyphenols from aqueous solutions. In cranberry juice, lecithin precipitated phenolics, proanthocyanidins and anthocyanins. Soy lecithin maximally depleted polyphenols 4% w/v. There is no significant difference in percentage depletion between total phenols, anthocyanins and proanthocyanidins at 4% and 5% w/v lecithin as juice polyphenols become the limiting substrates for the interaction. There is also no statistical difference between percentage depletion of proanthocyanidins at 0.05% and 0.5% w/v lecithin. It is probably because of the limited phospholipid bilayers at low lecithin concentration. The smaller polyphenols like phenolic compounds and anthocyanins interact more readily with the hydrophilic region of the lecithin, which inhibits proanthocyanidins from entering the hydrophobic region.

We also tested the possible interaction between phospholipids and other polyphenol compounds. Our data indicated that the interaction is not limited to anthocyanins. Total phenols and proanthocyanidins in cranberry juice also interacted with phospholipids. Unlike charged anthocyanins compounds, proanthocyanidin is extremely hydrophobic with a Log P value of 10 [15]. Log P is used to describe the hydrophobicity/hydrophilicity of the molecule. The partition coefficient P is the ratio of a solute concentration between two immiscible solvents. We hypothesized phospholipid-polyphenol interaction was related to HLB values of the polyphenols, and we tested this hypothesis using polyphenols with Log P values ranging from −0.64 to 3.04. Anthocyanins, quercetin-3-O-galactoside, (+)-catechin, genistein, quercetin and resveratrol were precipitated by lecithins in aqueous solutions. Resveratrol and genistein were the most hydrophobic purified polyphenols tested, and these were depleted the most by lecithin addition. Quercetin-3-rutinoside, on the contrary, was the most hydrophilic molecule

TABLE 5

Interaction of 1% w/v lecithin with individual phenolic acid, flavonols and anthocyanins at pH 2.43.[1]

| Compound | MW | # of phenolic —OH | Log P | Depletion % |
|---|---|---|---|---|
| quercetin-3-O-rutinoside | 610.52 | 4 | −0.64 ± 0.05[†] | 0[a] |
| cyanidin-3-O-glucoside | 484.8 | 4 | 0.39[†] | 45.0 ± 3.5[b,d] |
| quercetin-3-O-galactoside | 464.4 | 4 | 0.47[‡] | 35.4 ± 1.01[b] |
| (+)-catechin | 290.26 | 4 | 0.51[†] | 18.4 ± 0.5[c] |
| gallic acid | 170.12 | 3 | 0.71 ± 0.21[†] | 0[a] |
| cyanidin-3-O-arabinoside | 454.8 | 4 | 0.98[‡] | 16.0 ± 6.5[c] |
| cyanidin-3-O-galactoside | 449.4 | 4 | 0.98[‡] | 49.1 ± 3.5[d] |
| delphinidin-3-O-arabinoside | 470.8 | 5 | 1.35[‡] | 11.1 ± 4.9[c] |
| peonidin-3-O-glucoside | 463.4 | 3 | 1.18[‡] | 43.0 ± 4.0[b,d] |
| peonidin-3-O-galactoside | 498.9 | 3 | 1.20[‡] | 42.2 ± 4.1[b,d] |
| peonidin-3-O-arabinoside | 468.8 | 3 | 1.62[‡] | 10.1 ± 6.3[c,a] |
| quercetin | 302.2 | 4 | 1.82 ± 0.32[†] | 41.3 ± 1.8[b,d] |
| resveratrol | 228.3 | 3 | 2.57[†] | 71.8 ± 01.8[f,e] |
| genistein | 270.2 | 3 | 3.04 ± 0.02[†] | 61.0 ± 3.8[e] |

[1]The depletion % are reported as means ± SD, n = 3 or greater. Different superscript letters in the same row indicate significate differences in the mean. (P < 0.05). Anthocyanins were depleted from single-strength 100% cranberry juice.
[†]Log P values from literature [10-14]
[‡]Log P from ALOGPS software (v 2.1).

tested and had no interaction with lecithin. Quercetin-3-galactoside and quercetin had higher hydrophobicity than quercetin-3-rutinoside and were significantly depleted by lecithin. Interestingly, gallic acid, whose hydrophobicity lies in the middle of the Log P range tested, did not interact with lecithin. We initially hypothesized that the polyphenol-lecithin interaction would depend on polyphenol hydrophobicity. However, there was not a strong relationship between polyphenol Log P value and lecithin precipitation ($R2=0.3974$).

Figure 16:
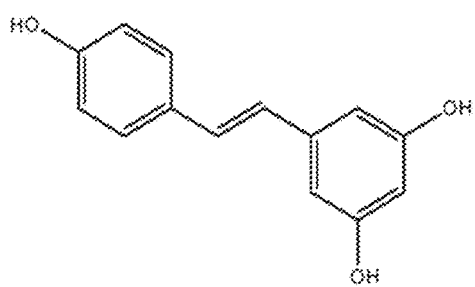
FIG. 16. Chemical structures of the individual polyphenols.
Figure 16:
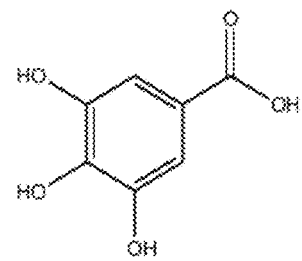
Figure 16:
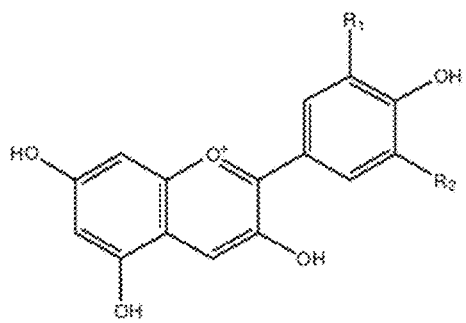
Figure 16:
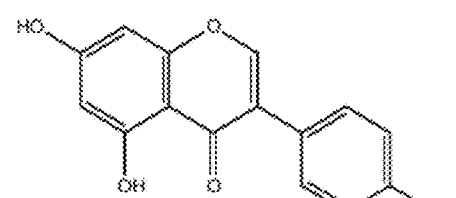
Figure 16:
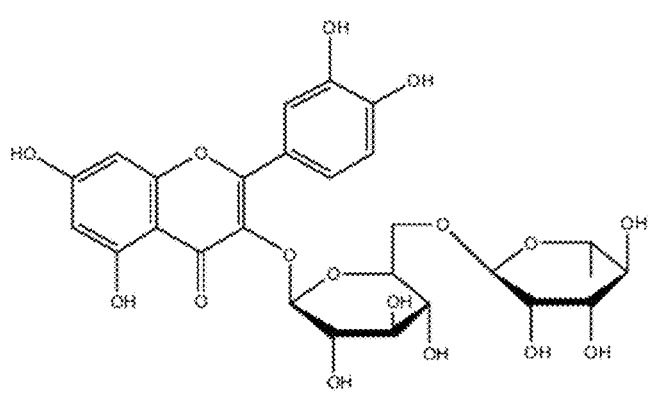
Figure 16:
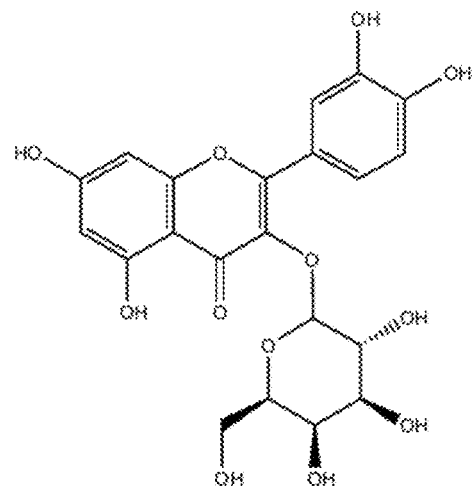
Figure 16:
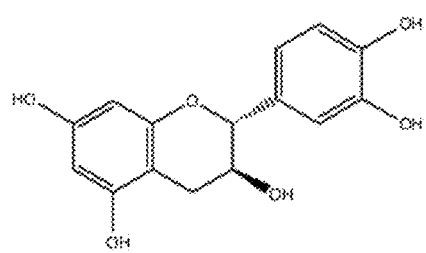
Figure 16:
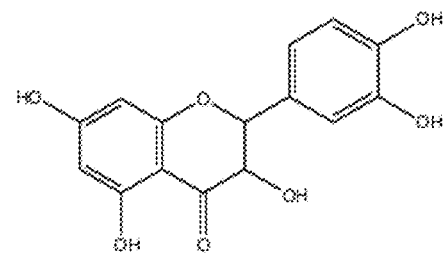
Figure 17:
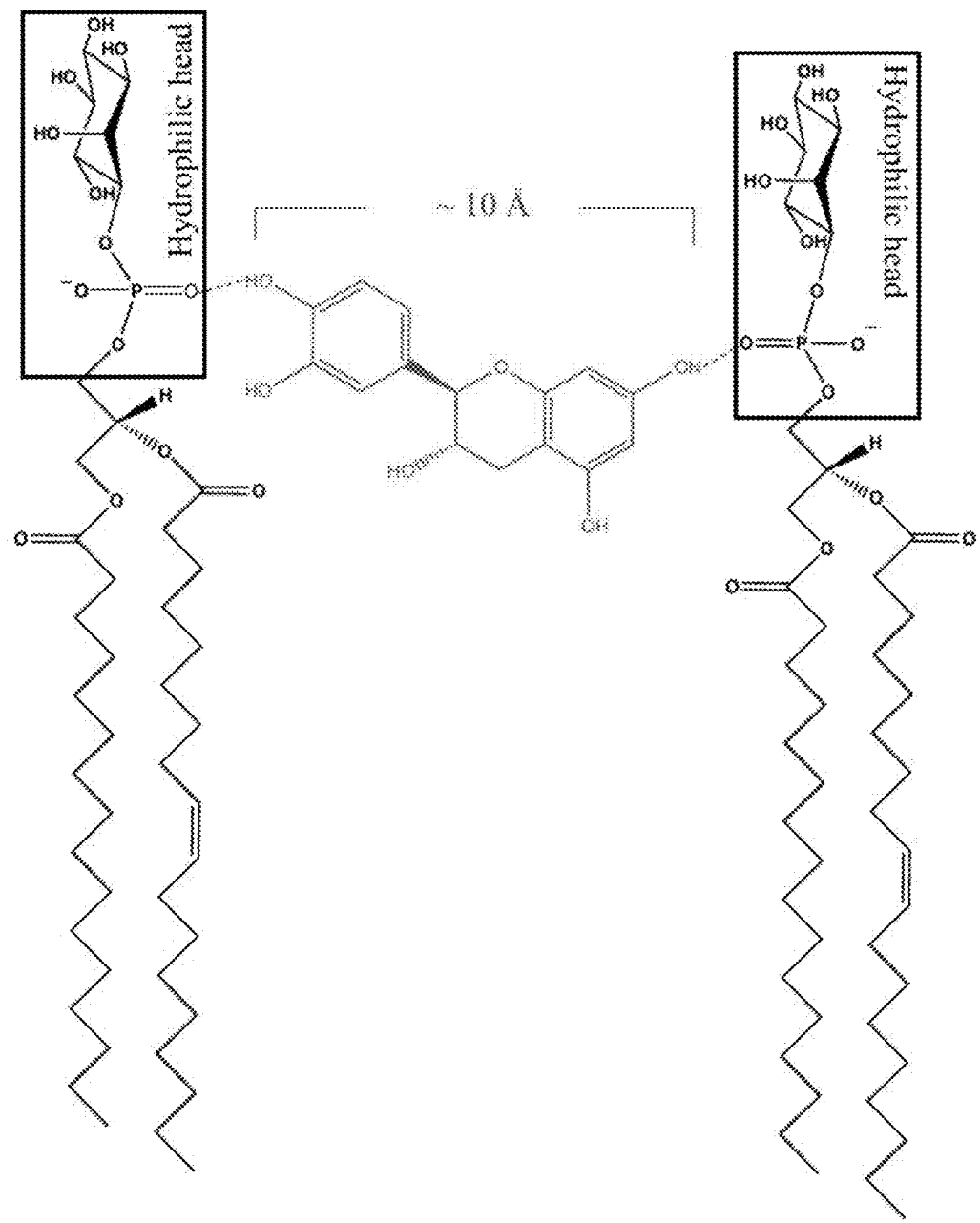
FIG. 17. Possible interaction of (+)-catechin with phospholipids.

Gallic acid did not precipitate lecithin, in contrast to flavonoids with similar Log P values. This suggested the polyphenol-lecithin interaction also depends on polyphenol size. Hydrogen bonding between the phenolic hydroxyl group on the polyphenols and the phosphate group on the phospholipids may be a requirement for precipitation. The structures of individual polyphenols are shown in FIG. 16. It is possible, that polyphenols could be oriented near the glycerol residues of phospholipids (FIG. 17). If this were the case, hydrogen bonds could be formed between the —OH group in the polyphenols and the —P=O group in the phospholipids. The hydroxyl group on the sugar moieties might also involve in the hydrogen bonding with the phospholipids. The percentage depletion of cyanidin-3-arabinose was significantly lower than that of cyanidin-3-galactoside and cyanidin-3-glucoside. Similar results were observed with peonidin-3-arabinose.

A similar model was created by Phan et al. to illustrate the structure-dependent interactions of polyphenols with the membrane system [17]. They proposed that flavonoids with gallate, galloyl and hydroxyl groups mainly affect hydrophilic region of the lipid bilayers by forming hydrogen bonds on the membrane surface, while trans-stilbenes could penetrate the surface and insert into the hydrophobic region. Our model supports this type of interaction between flavonoids and the phospholipids. However, this may be most relevant to polyphenols with high hydrophobicity (e.g. proanthocyanidin, resveratrol, genistein).

Although gallic acid has similar phenolic hydroxyl groups with other polyphenol compounds, the hydrogen bonding theory fails to explain why there is no interaction between gallic acid and phospholipids. We think the molecular geometry might be able to account for the zero interaction between the two. Unlike other polyphenol compounds that have phenolic hydroxyl groups on both side of the molecule, all three phenolic hydroxyl group are located on one side of the molecule. Furthermore, the molecular size might pose a constraint to the interaction as gallic acid is a smaller molecule compared to the other polyphenols. Thus, gallic acid could only interact with one side of the phospholipid, which makes it difficult to disrupt the phospholipid membrane and cause the aggregation.

Conclusion

In this example, we found that soy lecithin interacted with a wide range of polyphenols and that the interaction extends beyond juice anthocyanins. Polyphenols including stilbenes, flavonol glycosides, flavan-3-ols and proanthocyanidins can be selectively extracted from the aqueous systems, where the possible mechanism activity is caused by hydrogen bonding and hydrophobic interaction. The structural features affecting this interaction include flavonoid polarity, phenolic hydroxyl groups, and molecular geometry. In addition to fruit juices, this method could be useful in a wide variety of polyphenol-rich sources, such as vegetables, botanicals, and legumes.

REFERENCES

[1]. Zhang, L., Zhang, X., Cheng, M., Cao, J., Wu, Z., Weng, P., Yan, M. Oolong Tea Polyphenols-Phospholipids Complex Reduces Obesity in High Fat Diet-Induced Mice Model. European Journal of Lipid Science and Technology. 2017, 119, 1600394.

[2]. Lu, M., Qiu, Q., Luo, X., Liu, X., Sun, J., Wang, C., Lin, X., Deng, Y., Song, Y. Phyto-phospholipid complexes (phytosomes): A novel strategy to improve the bioavailability of active constituents. Asian Journal of Pharmaceutical Sciences. 2019, 14, 265-274.

[3]. Wei, L., Kelly, A. L., Song, M. Emulsion-based Encapsulation and Delivery Systems for Polyphenols. Trends Food Sci Tech. 2016, 47, 1-9.

[4]. Aude, M., Florence, E. L. Encapsulation of Natural Polyphenolic Compounds: A Review. Pharmaceutics. 2011, 3, 793-829.

[5]. He, J. L., Luo, L. Y., Zeng, L. Recent Advances in Research on Preparation Technologies and Applications of Tea Polyphenol Nanoparticles. Food Sci. 2011, 32, 317-322.

[6]. Lee, J., Durst, R. W., Wrolstad, R. E. Determination of Total Monomeric Anthocyanin Pigment Content of Fruit Juices, Beverages, Natural Colorants, and Wines by the pH Differential Method: Collaborative Study. Journal of AOAC International. 2005, 88, 1269-1278.

[7]. Singleton, V. L.; Orthofer, R.; Lamuela-Raventós, R. M. Analysis of Total Phenols and Other Oxidation Substrates and Antioxidants by Means of Folin-Ciocalteu Reagent. Methods Enzymol. 1999, 299, 152-178.

[8]. Prior, R. L.; Fan, E.; Ji, H.; Howell, A.; Nio, C.; Payne, M. J.; Reed, J. Multi-laboratory Validation of a Standard Method for Quantifying Proanthocyanidins in Cranberry Powders. J. Sci. Food Agric. 2010, 90, 1473-1478.

[9]. Wu, X., Prior, R. L. Systematic identification and characterization of anthocyanins by HPLC-ESI-MS/MS in common foods in the United States: Fruits and berries. Journal of Agricultural and Food Chemistry. 2005, 53, 2589-2599.

[10]. Rothwell, J. A., Day, A. J., Morgan, M. R. Experimental determination of octanol-water partition coefficients of quercetin and related flavonoids. J. Agric. Food Chem. 2005, 53, 4355-4360.

[11]. Tian, B. R., Liu, J. Y., Ge, H. R., Wang, Z. Z. et al. The design, synthesis and characterization of resveratrol derivatives modified by different y-Aminobutyric Acid Esters. Journal of Chemistry. 2019, 2019, 1-6.

[12]. Olivas-Aguirre, F. J., Rodrigo-Garcia, J., Martinez-Ruiz, N. D., Cardenas-Robes, A. I. et al. Cyanidin-3-O-glucoside: Physical—Chemistry, Foodomics and Health Effects. Molecules. 2016, 21, 1264-1294.

[13]. Elendran, S., Wang. L. W., Prankered, R., Palanisamy, U. D. The physicochemical properties of geraniin, a potential antihyperglycemic agent. Pharmaceutical Biology. 2015, 53, 1719-1726.

[14]. Perrissoud, D., Testa, B Inhibiting or potentiating effects of flavonoids on carbon tetrachloride-induced toxicity in isolated rat hepatocytes. Arzneimittelforschung. 1986, 36, 1249-1253.

[15]. Mueller-Harvey, I., Mlambo, V., Sikosana, J. L. N., Smith, T. et al. Octanol-water partition coefficients for predicting the effects of tannins in ruminant nutrition. J. Agri. Food Chem. 2007, 55, 5436-5444.
[16]. Pu, Y., Zhang, X., Zhang, Q. 20(S)-Proropanaxadiol Phospholipid Complex: Process Optimization, Characterization, in vitro Dissolution and Molecular Docking Studies. Molecules, 2016, 21, 1396-1417.
[17]. Phan, H. T. T., Yoda, T., Chahal, B., Morita, M. et al. Structure-dependent interactions of polyphenols with a biomimetic membrane system. Biochimica et Biophysica Acta (BBA)-Membranes. 2014, 1838, 2670-2677.

Example 5: Effect of Solution Characteristics on Phospholipid-Polyphenol Interaction Abstract In this example, we hypothesized lecithin and polyphenols precipitate in aqueous solutions due hydrophobic interactions and hydrogen bonding. The objective of this example was to further investigate these mechanisms in aqueous solutions. We tested the influence of pH, alcohol content, ionic strength, and sugar content on depletion on monomeric anthocyanins at room temperature. Aqueous solutions with acidic pH (less or equal to 1.0) or high ionic strength reduced lecithin-induced precipitation of anthocyanins in cranberry juice. The studies suggested the importance of ions in mediating phospholipid-anthocyanin precipitation, which confirmed the hydrogen bonding between the polyphenols and polar headgroups of the phospholipid. Proanthocyanidins, which we expect to associate with the phospholipid via hydrophobic interaction, was not significantly affected by change in pH in the cranberry juice. Increased sugar content (e.g. ° Brix>10) reduced lecithin-polyphenol precipitation. On the other hand, addition of alcohol favored the phospholipid-polyphenol precipitation. This information opens for new possibilities to enhance the complex formation in aqueous systems and helps understand the factors that affect polyphenol-phospholipid interactions.

Introduction

In the previous example, we compared several polyphenols with various polarities, molecular size to evaluate the relative importance of hydrogen bonding and hydrophobic interactions between phospholipids and polyphenols. Some studies have described this interaction and suggested hydrogen bonding and hydrophobic interaction might account for the binding activity [1-6]. (+)-Catechin and its derivatives may adsorb to the membrane surfaces and insert into the lipid bilayer, forming hydrogen bonds with the phospholipids [7]. 20 (5)-Protopanaxadiol phospholipid complexes showed formation of hydrogen bond between one of the —OH group in 20 (S)-protopanaxadiol and the —P=O group in the phospholipids [8]. Whether they are the mechanism for the activity still requires understanding.

The objective of present example is to determine the environmental factors that affect the phospholipid-polyphenols interaction in order further attempt to explain the mechanism of the formation of the complexes. We hypothesized the level of interaction between phospholipids and polyphenols would be influenced by the environmental factors and the results could elucidate the mechanism of phospholipid activity. Specific polyphenols, anthocyanins, were analyzed in this example because they are important pigments. We evaluated factors such as pH, alcohol content, ionic strength, and sugar content of the juice solutions for their impacts on phospholipid-anthocyanin interaction.

Methods
Reagents

Unless specified otherwise, the lecithin employed was soybean lecithin powder (Product No. J61675, Alfa Aesar, Ward Hill, Mass., U.S.A.). Potassium chloride (ACS certified), sodium chloride and hydrochloric acid (ACS certified) were from Thermo Fisher Scientific (Waltham, Mass., U.S.A.). ACS reagent grade gallic acid monohydrate was from Acros Organics (Morris Plains, N.J., U.S.A.) (+)-Catechin hydrate (98% purity) was obtained from Cayman Chemical (Ann Arbor, Mich., U.S.A.). Ultrapure grade water was purified to at least 18.1 M Ω·cm using a Barnstead water filtration system (Thermo Fisher Scientific). All reagents were used without further purification except as noted. Pectin was pre-hydrated Pectin 1694 Powder (TIC Gums, Belcamp, Md.), which is a high-methoxy, cold-water soluble pectin standardized with maltodextrin for viscosity. The pectin powder was added directly to reconstituted juice on a w/w basis.

Diluted Cranberry Juice Preparation

Single-strength cranberry juice was prepared freshly from frozen juice concentrates as described in Example 3.

Combining Lecithin with Juice Samples

Soy lecithin (1% w/v) was added to 5 mL cranberry juice samples (pH ~2.43). The mixture was then vortexed for 3 min and then centrifuged at 3220×g for 20 min to separate precipitate. The centrifugation step was repeated with the supernatants. All procedures were carried out at ambient temperatures unless otherwise specified.

Effect of pH

Juice pH was measured using a Seven Compact pH/Ion meter 5220 (Mettler Toledo, Columbus, Ohio, U.S.A.). The pH of single-strength cranberry juice was adjusted to pH 1.5 or 2.0 with 6 M HCL and pH 3.0 or 3.5 with 6 M NaOH.

Effect of Alcohol Content

Single strength cranberry juice samples at 7.5 brix with varying ethyl alcohol content (0, 4, 8, 12% v/v) were prepared. A 5 mL aliquot of cranberry juice was combined with 0, 0.2, 0.4, 0.6 mL ethyl alcohol.

Effect of Ionic Strength

Cranberry juice samples were prepared with varying ionic strength. NaCl and $CaCl_2$ were selected to compare the effect of divalent and monovalent salt. Solutions with 0, 0.01, 0.10, 0.20 M NaCl or $CaCl_2$ were prepared in 5 mL aliquots.

Effect of Sugar Content

Glucose, a simple sugar that is commonly present in cranberry, was added to the diluted cranberry juice to achieve 7.5, 10, 20, 30, 40 Brix° solutions.

Monomeric Anthocyanin (MA) Analysis

MA content was determined by the AOAC pH differential method as described in Example 3 [6].

Determination of Sugar Content

A refractometer (Thermo Spectronic 334610) was used to determine the sugar concentration in juice samples. It displayed both refractive index (nD) and Brix° values with current room temperature. Brix° value is the total sugar concentration in % (w/v) of a solution with the same refractive index.

Percent Depletion

The depletion of anthocyanin content expressed as a percent was determined according to the following equation:

$$\% \text{ depleted} = \frac{MA_{control} - MA_{lecithin\ treated}}{MA_{control}} \times 100$$

Statistical Analysis

The mean and standard error of each treatment were calculated from triplicates. Analysis of variance (ANOVA) was carried out to determine any significant differences between treatments (P<0.05).

Results

Effect of pH on Depletion of Anthocyanins and Proanthocyanidins

Figure 18:
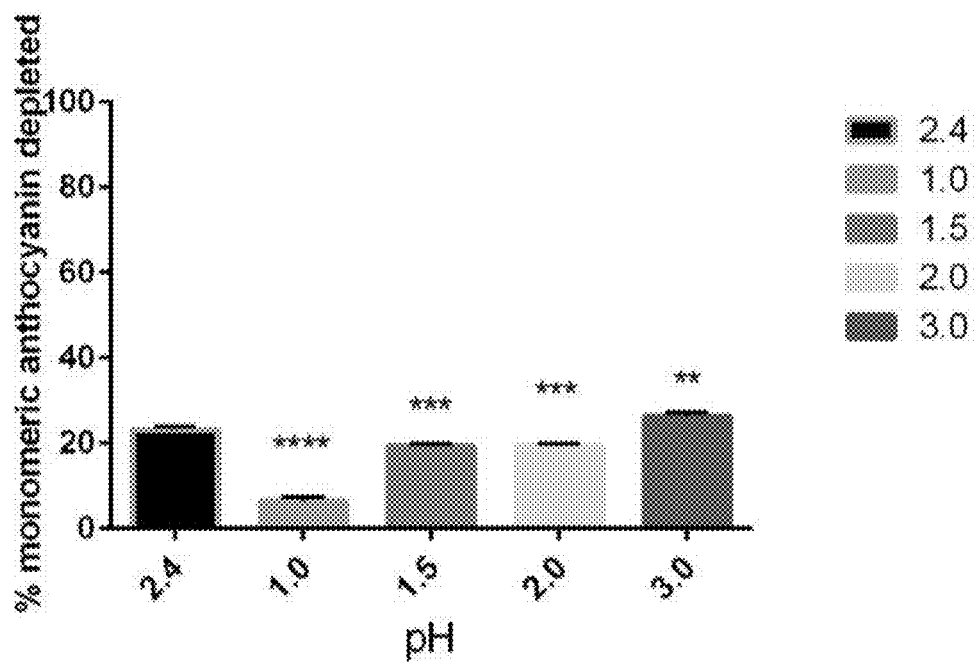
FIG. 18. Effects of pH on percentage monomeric anthocyanin depletion by 1% w/v lecithin.

Cranberry juice polyphenols were precipitated by lecithin at pH 1.0, 1.5, 2.0, 2.5 and 3.0 The pH of juice had a significant impact the extent of lecithin-anthocyanin co-precipitation (FIG. 18). At pH 1.0, the percentage of anthocyanin depleted was 6.42±0.93%, which was significantly less than the control at pH 2.4 (23.2±0.7%). Thus, below pH 2.0, lecithin-polyphenol precipitation was reduced. In solutions above pH 2.0, lecithin had similar levels of polyphenol co-precipitation, depleting 20-30% of the anthocyanins in the cranberry juice. When pH increased from 1.0 to 1.5, the percentage depletion of anthocyanins increased significantly. Comparatively, the depletion efficiency of lecithin showed its maximum at pH 3.0.

Figure 19:
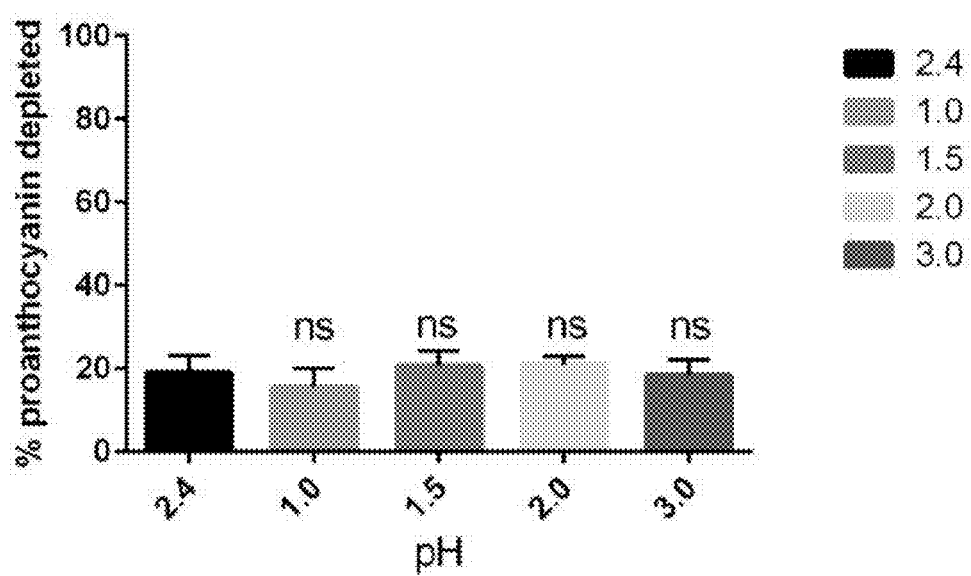
FIG. 19. Effects of pH on percentage proanthocyanidin depletion by 1% w/v lecithin.

In contrast to anthocyanins, juice pH did not significantly affect lecithin-induced precipitation of proanthocyanidins (FIG. 19). The proanthocyanidins in the control cranberry juice was depleted by 19.0±4.2%. Below pH 2.4, the percentage of proanthocyanidin was depleted by 15.6±4.4%, 20.7±3.5% and 20.9±2.0%. However, by one-way ANOVA, the change in pH did not significantly impact the percentage depletion of proanthocyanidins at any pH compared to the control (pH=2.4).

Effect of Alcohol Content on Depletion of Anthocyanins

Next, we determined the effects of alcohol content on the lecithin-induced anthocyanin depletion. Ethanol was used to simulate approximate levels in wine containing 4%, 8% or 12% v/v alcohol content (Table 6). The percentage of anthocyanins depleted by lecithin significantly increased from 26.9±0.9% to 29.8±1.3% when 4% ethyl alcohol was added to the control juice.

At 12% v/v % ethyl alcohol content, the percentage depletion of anthocyanins was significantly higher than the control. However, it is not significantly different from 4% and 8% v/v alcohol content. All of the alcohol treatments had significantly higher percentage depletion than the control (0% v/v ethyl alcohol, P<0.05). Thus, reducing the polarity of the aqueous phase increased the ability of lecithin to induce precipitation of juice anthocyanins.

TABLE 6

Depletion of monomeric anthocyanins by 1% w/v lecithin in 100% cranberry juice with various ethyl alcohol content.[1]

| Ethyl alcohol v/v % | Depletion % |
|---|---|
| 0 | 26.9 ± 0.9$^c$ |
| 4 | 29.8 ± 1.3$^b$ |
| 8 | 32.3 ± 0.8$^a$ |
| 12 | 31.3 ± 0.8$^{a,b}$ |

[1]Data are reported as means ± SD, n = 3 or greater. Different superscript letters in the same row indicate significate differences in the mean (P < 0.05).

Effect of Ionic Strength on Depletion of Anthocyanins

Figure 20:
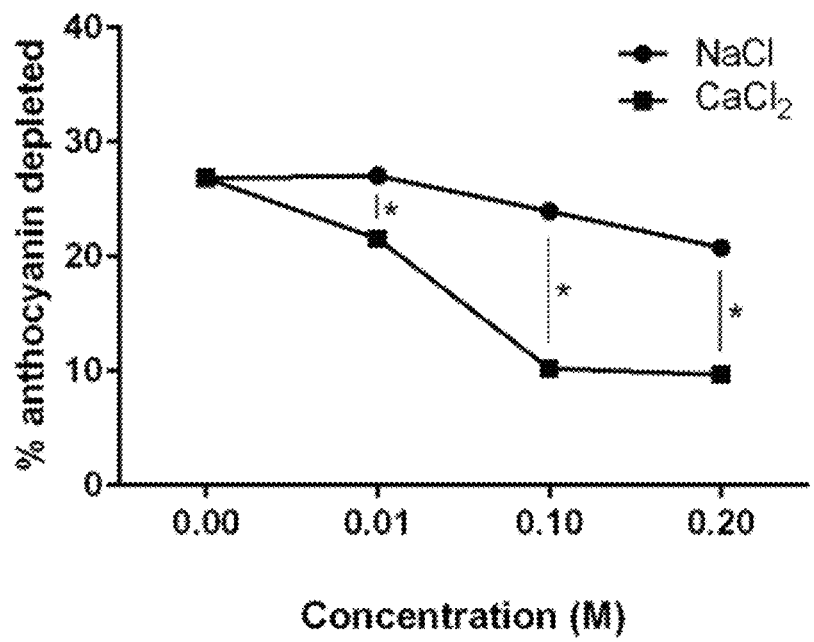
FIG. 20. Effects of ionic strength on percentage monomeric anthocyanin depletion by 1% w/v lecithin.

The effect of ionic strength and ion type on lecithin-induce precipitation of anthocyanins was tested by using NaCl and CaCl2. The concentration and types of cation affected the lecithin-induced depletion of anthocyanins from juice (FIG. 20). As the molar concentration of Na+ or Ca2+ ions increased in the cranberry juice, the percentage depletion of anthocyanins was reduced significantly. At the same concentration, juice samples that treated with CaCl2 showed less percentage depletion of anthocyanins compared to those treated with NaCl. The increase in ionic strength negatively impacted the percentage depletion of anthocyanins.

Effect of Sugar Content on Depletion of Anthocyanins

Figure 21:
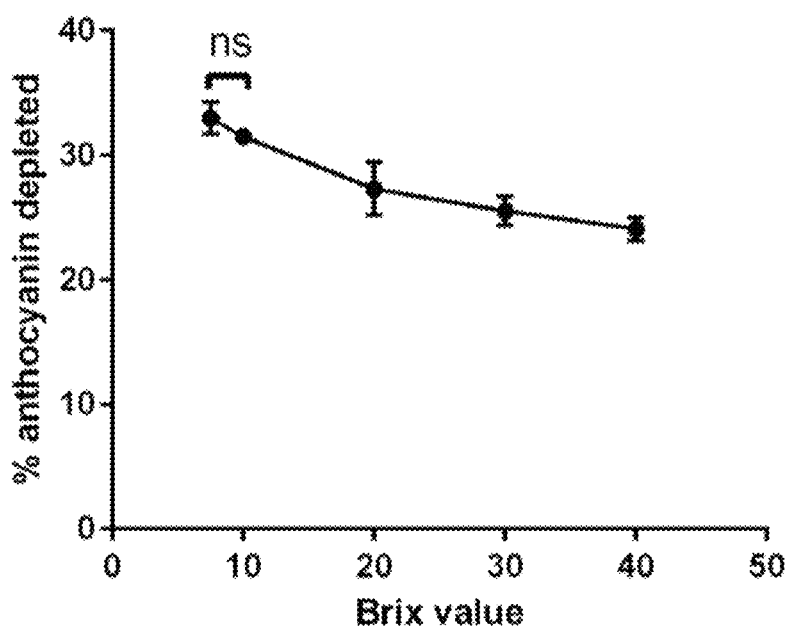
FIG. 21. Effects of sugar content on percentage monomeric anthocyanins depletion in diluted cranberry juice.

Increasing the glucose content of cranberry juice reduced the amount of anthocyanins precipitated by lecithin (FIG. 21). Anthocyanin depletion was 33.0±1.3% at control cranberry juice at ° Brix value 7.5. Anthocyanin depletion was significantly reduced to 27.3±2.1% and 25.5±1.2% at 20° Brix and 30° Brix. Depletion was significantly reduced to a minimal of 24.1±0.9% at 40° Brix, the maximum concentrate of glucose evaluated.

The effect of diluting cranberry concentrate is shown in Table 7.

TABLE 7

Impact of cranberry concentrate dilution on monomeric anthocyanin depletion by lecithin (Alfa Aesar).

| °Brix | Monomeric anthocyanin content at 0% w/v lecithin | Monomeric anthocyanin content at 4% w/w lecithin | Depletion (%) |
|---|---|---|---|
| 8.0 (control) | 62.2 ± 0.94 | 19.2 ± 0.14 | 69.1 ± 0.45 |
| 14.4 (half constituted) | 110.0 ± 0.48 | 35.3 ± 1.03 | 67.9 ± 0.82 |
| 51.5 (full concentrate) | 497.6 ± 19.1 | 498.7 ± 39.3 | −0.22 ± 7.59 |

The impact of pectin concentration on the efficiency of lecithin-induced monomeric anthocyanin precipitation was evaluated. Depletion was increased by the addition of pectin in a dose-dependent manner (Table 8).

TABLE 8

Impact of pectin on monomeric anthocyanin depletion.

| Pectin (% w/w) | Monomeric anthocyanin content at 0% w/w lecithin | Monomeric anthocyanin content at 4% w/w lecithin | Depletion (%) |
|---|---|---|---|
| 0 (control) | 65.8 ± 2.39 | 18.8 ± 0.77 | 71.3 ± 1.36 |
| 0.05 | 70.0 ± 2.31 | 18.3 ± 0.58 | 73.8 ± 1.05 |
| 0.25 | 68.2 ± 0.63 | 17.3 ± 0.03 | 74.6 ± 0.21 |

Lecithin-induced precipitation of polyphenols was not limited to removing anthocyanins from cranberry juice (Table 9). For example, lecithin induced precipitation of anthocyanins from anthocyanin-containing samples other than cranberry juice, such as concord grape juice, purple grape juice, pomegranate juice, and aronia juice. Lecithin also induced precipitation of phenols in samples not containing anthocyanins, such as white grape juice, orange juice, beet juice, and coffee (Table 9).

TABLE 9

Effect of 4% w/w lecithin on depletion of polyphenols from various types of beverages.

| Beverage | Total Phenols Depleted | Anthocyanins Depleted |
|---|---|---|
| Grape juice (purple) | ND | 45% |
| Grape juice (Concord) | ND | 40% |
| Grape juice (white) | 18% | ND |
| Cloudy cranberry juice | ND | 45% |
| Pink cranberry juice | 9% | ND |
| Pomegranate juice | ND | 58% |

TABLE 9-continued

Effect of 4% w/w lecithin on depletion of
polyphenols from various types of beverages.

| Beverage | Total Phenols Depleted | Anthocyanins Depleted |
|---|---|---|
| Aronia juice | ND | 49% |
| Apple juice (#1) | 12% | ND |
| Apple juice (#2) | 15% | ND |
| Orange juice (no pulp) | 13% | ND |
| Beet juice | 10% | ND |
| Coffee | 8% | ND |

ND, not determined

Temperature affected the degree of lecithin-induced anthocyanin depletion from cranberry juice (Table 10). Depletion was favored under cool temperatures, consistent with the opposing effect of lecithin hydrophobicity (e.g. higher temperatures favor hydrophobic interactions).

TABLE 10

Effect of temperature on monomeric anthocyanin content.

| Temperature | Monomeric anthocyanin content at 0% w/w lecithin | Monomeric anthocyanin content at 2% w/w lecithin | Depletion (%) |
|---|---|---|---|
| Room Temp (control) | 64.6 ± 0.70 | 23.5 ± 0.68 | 63.6 ± 0.97 |
| Cooled (3.5° C.) | 66.0 ± 0.47 | 21.4 ± 0.35 | 67.6 ± 0.50 |
| Heated (45° C.) | 63.2 ± 1.09 | 29.6 ± 0.11 | 53.2 ± 0.71 |

DISCUSSION

We examined how pH, ethanol, ions, and glucose modify lecithin-induced precipitation of cranberry juice anthocyanins. pH was an important factor that affected the extent of anthocyanin-lecithin precipitation. The pka values of three major components in lecithin, PE, PI, PC are 1.7, 2.5, 1.0, respectively [11]. Thus, the different pH of the juice solutions altered the lecithin headgroup charges. At pH 1.0, where pH is below the pka of PE and PI, the negatively charged oxygen atom on the phosphate group of PE and PI would be protonated, leading to the formation of hydroxyl (—OH) group. The hydroxyl group on polar heads would form hydrogen bonds with the water molecules and thus weaken the hydrogen bonding between phosphate (P=O) group and the anthocyanins. Mrazkova et al. suggested similar findings that upon hydration there was a loss of electron density of the P=O bonds on methylphosphocholine due to formation of hydrogen bonds with water molecules [12]. As a consequence, the depletion of monomeric anthocyanins was significantly reduced by the acidic environment. However, if the pH of the solution was increased to juice's original pH value or above, the phosphate headgroups were deprotonated, and the ability to deplete anthocyanins from the cranberry juice was increased.

Alcohol content is another factor that could affect the phospholipid's depletion ability. According to the results, the addition of ethanol enhanced phospholipid-induced anthocyanin precipitation. At level of ethanol addition, the depletion of anthocyanins was significantly greater compared to the control. The results suggest that alcohol enhances the phospholipid-polyphenol interaction. As ethanol is introduced in the system, water-ethanol hydrogen bonding is strengthened [13]. Also, water-ethanol interactions were enhanced by the presence of polyphenols in alcoholic drinks [13]. The interaction between water and ethanol reduced the extent of hydrogen bonding between water and polar phosphate head, which makes polyphenols more accessible to the phosphate headgroup. The alcohol content in drinks containing alcohol is in the range of 4-12% by volume.

The efficacy of phospholipid-induced precipitation of cranberry juice anthocyanins also depends on ionic strength. The increased ionic strength of sodium and calcium chloride reduced precipitation. Sodium and calcium cations could bind with the oxygen anion on the phosphate group to compete with the juice anthocyanins. The strong binding of the cations to the phospholipid bilayer was reported by Melcrová et al. [14]. The researchers suggested multiple binding sites using molecular dynamics simulation include carboxylate groups, phosphates, and carbonyl groups on the phospholipid molecules. Furthermore, divalent cation, $Ca^{2+}$ ions, reduced the depletion of anthocyanins more so than the monovalent $Na^+$. The interaction between the $Na^+$ and the negatively charged oxygen atom on the phosphate group is relatively weak compared to the $Ca^{2+}$ because $Ca^{2}$ ions can concurrently bound to more than one phospholipid molecule at a time [14]. Many studies demonstrated that calcium ions bind to phosphate groups of all phospholipids, independent of charge, even in pure PC membranes [15-17].

In addition, increasing glucose content reduces phospholipid-polyphenol interaction. The decrease in percentage depletion is likely caused by competing factor glucose. Sugars including trehalose, maltose and glucose were found to interact directly with the phosphate headgroups through hydrogen bonding reported by Pereira et al. [18]. The formation of hydrogen bonds between glucose and phospholipids likely prevent the association of the phospholipids with the polyphenols. Other studies have shown that carbohydrates can interact with polyphenols as well [19-23]. It was found that procyanidins bound to cell wall carbohydrates like pectin, cellulose, or dietary fibers.

This could lead to reduce the polyphenols that interact with the phospholipids. Therefore, the interaction of phospholipids and polyphenols could possibly be affected by the association of sugar with both phospholipids and polyphenols.

Conclusion

In conclusion, multiple factors affect the phospholipids-polyphenols interaction, such as pH, alcohol content, ionic strength, and sugar content. The data in this example help elucidate our understanding of the mechanism and suggest the conditions that could enhance this interaction. Hydrogen bonding and hydrophobic interaction play important role in phospholipids-polyphenols interaction. Most fruits and vegetables solutions have pH above 1 and sugar content less than 10. Therefore, this method shows wide applications for polyphenols extraction purposes.

REFERENCES

[1]. Sirk, T. W., Brown, E. F., Sum, A. K., Friedman, M. Molecular Dynamics Study on the Biophysical Interactions of Seven Green Tea Catechins with Lipid Bilayers of Cell Membranes. J. Agric. Food. Chem. 2008, 56, 7750-7758.

[2]. Yu, X., Chu, S., Hagerman, A. E., Lorigan, G. A. Probing the Interaction of Polyphenols with Lipid Bilayers by Solid-state NMR Spectroscopy. J. Agric. Food. Chem. 2011, 59, 6783-6789.

[3]. Uekusa, Y., Kamihira, M., Nakayama, T. Dynamic Behavior of Tea Catechins Interacting with Lipid Membranes as Determined by NMR Spectroscopy. J. Agric. Food Chem. 2007, 55, 9986-9992.

[4]. Tsuchiya, H. Effects of Green Tea Catechins on Membrane Fluidity. Pharmacology. 1999, 59, 34-44.

[5]. Hashimoto, T., Kumazawa, S., Nanjo, F., Hara, Y., Nakayama, T. Interaction of Tea Catechins with Lipid Bilayers Investigated with Liposome Systems. Biosci. Biotechnol. Biochem. 1999, 63, 2252-2255.

[6]. Yoshioka, H., Haga, H., Kubota, M., Sakai, Y. Interaction of (+)-Catechin with a Lipid Bilayer Studied by the Spin Probe Method. Biosci. Biotechnol. Biochem. 2006, 70, 395-400.

[7]. Kajiya, K., Hojo, H., Suzuki, M., Nanjo, F., Kumazawa, S., Nakayama, T. Relationship Between Antibacterial Activity of (+)-Catechin Derivatives and Their Interaction with a Model Membrane. J. Agric. Food Chem. 2004, 52, 1514-1519.

[8]. Pu, Y., Zhang, X., Zhang, Q. 20(S)-Proropanaxadiol Phospholipid Complex: Process Optimization, Characterization, in vitro Dissolution and Molecular Docking Studies. Molecules, 2016, 21, 1396-1417.

[9]. Tanaka, Y., Sasaki, N., Ohmiya, A. Biosynthesis of Plant Pigments: Anthocyanins, Betalains and Carotenoids. Plant J. 2008, 54, 733-749.

[10]. Kong, J. M., Chia, L. S., Goh, N. K., Chia, T. F., Brouillard, R. Analysis and Biological Activities of Anthocyanins. Phytochemistry. 2003, 64, 923-933.

[11]. Tsui, F. C., Ojcius, D. M., Hubbell, W. L. The Intrinsic pKa Values for Phosphatidylserine and Phosphatidylethanolamine in Phosphatidylcholine Host Bilayers. Biophys J. 1986, 49, 459-68.

[12]. Mrazkova, E., Hobza, P., Bohl, M., Gauger, D. R., Pohle, W. Hydration-Induced Changes of Structure and Vibrational Frequencies of Methylphosphocholine Studied as a Model of Biomembrane Lipids. J. Phys. Chem. B. 2005, 109, 15126-15134.

[13]. Nose, A., Hojo, M. Hydrogen bonding of water-ethanol in alcoholic beverages. J. Biosci. Bioeng. 2006, 102, 269-280.

[14]. Melcrová, A., Pokorna, S., Pullanchery, S., Kohagen, M., Jurkiewicz, P., Hof, M., Jungwirth, P., Cremer, P. S., Cwiklik, L. The Complex Nature of Calcium Cation Interactions with Phospholipid Bilayers. Sci Rep. 2016, 6, 38035-38047.

[15]. Binder, H., Zschornig, O. The effect of metal cations on the phase behavior and hydration characteristics of phospholipid membranes. Chemistry and physics of lipids. 2002, 115, 39-61.

[16]. Herbette, L., Napolitano, C., McDaniel, R. Direct determination of the calcium profile structure for dipalmitoyllecithin multilayers using neutron diffraction. Biophysical journal. 1984, 46, 677.

[17]. Uhrikova, D., Kucerka, N., Teixeira, J., Gordeliy, V., Balgavy, P. Structural changes in dipalmitoylphosphatidylcholine bilayer promoted by Ca2+ ions: a small-angle neutron scattering study. Chemistry and physics of Lipids. 2008, 155, 80-89.

[18]. Pereira, C., Hünenberger, P. H. Interaction of the sugars trehalose, maltose and glucose with a phospholipid bilayer: a comparative molecular dynamics study. J. Phys. Chem. B. 2006, 110, 15572-15581.

[19]. Le Bourvellec, C., Guyot, S., Renard, C. M. G. C. Interactions Between Apple (*Malusxdomestica* Borkh.) Polyphenols and Cell Walls Modulate the Extractability of Polysaccharides. Carbohydrate Polymers. 2009, 75, 251-261.

[20]. Padayachee, A., Netzel, G., Netzel, M., Day, L., Zabaras, D., Mikkelsen, D., Gidley, M. J. Binding of Polyphenols to Plant Cell Wall Analogues—Part 1: Anthocyanins. Food Chemistry. 2012, 134, 155-161.

[21]. Padayachee, A., Netzel, G., Netzel, M., Day, L., Zabaras, D., Mikkelsen, D., Gidley, M. J. Binding of Polyphenols to Plant Cell Wall Analogues—Part 2: Phenolic Acids. Food Chemistry. 2012, 135, 2287-2292.

[22]. Pekkinen, J., Rosa, N. N., Savolainen, O. I., Keski-Rahkonen, P., Mykkänen, H., Poutanen, K., Micard, V., Hanhineva, K. Disintegration of Wheat Aleurone Structure Has an Impact on the Bioavailability of Phenolic Compounds and Other Phytochemicals as Evidenced by Altered Urinary Metabolite Profile of Diet-induced Obese Mice. Nutrition and Metabolism. 2014, 11, 1-15.

[23]. Rosa, N. N., Dufour, C., Lullien-Pellerin, V., Micard, V. Exposure or Release of Ferulic Acid from Wheat Aleurone: Impact on Its Antioxidant Capacity. Food Chemistry. 2013, 141, 2355-2362.

Example 6: Isolation of Polyphenols from Cranberry Juice by Soy Lecithin

Abstract

The objective of this example was to develop a simple strategy to selectively isolate polyphenols from aqueous systems containing soy lecithin. Lecithin was applied to cranberry juice as a powder or pre-dispersed in water, and a modified lecithin with increased HLB (Emulfluid® HL 66) was tested for comparison. The polyphenols in the phospholipid-polyphenol precipitate were extracted by 50% v/v acetone in ethanol. The recovery of anthocyanins from lecithin powder precipitate was maximal at 1% (w/v), with 29.4±2.3%. However, at 4% lecithin (w/v), anthocyanin recovery was only 18.0±0.9%. With a 1% w/v pre-dispersed lecithin, the recovery of anthocyanins was improved to 34.1±1.6%. Emulfluid® HL 66 led to recovery of 34.2±3.7% of anthocyanins from the cranberry juice, which was no different from powder lecithin. The polyphenol profile of the resulting extract was determined using HPLC. The purified extract from powder lecithin contained phenolic acids such as gallic acid, protocatechuic acid, caffeic acid, 3.4-dihydroxyphenylacetic acid, chlorogenic acid, flavonoids such as catechin, quercetin-3-O-galactoside, quercetin-3-O-glucoside, anthocyanins as well as proanthocyanidins. Thus, purified polyphenols can be recovered from lecithin-fruit juice precipitates and depend on the dose and type of lecithin applied to aqueous solutions.

Introduction

Polyphenols are considered important bioactive compounds with considerable health benefits and studies have been focusing on developing green techniques to isolate and purity polyphenol compounds [1]. The traditional process involves steps like crushing the raw fruits, blending to fruit juice, sterilizing by heat and drying into powder by spray dryers. Modern green extraction techniques include supercritical fluid extraction (SFE), ultrasound-assisted extraction (UAE), microwave-assisted extraction (MAE), pressurized liquid extraction (PLE) and pressurized hot water extraction (PHWE) [2-12]. The limitation to these methods is that the extract is mixed with other components such as sugars, proteins, and fibers. In addition, these methods post large expenditure on energy and the processing instruments.

In previous examples, we demonstrated lecithin phospholipids exhibit strong interactions with polyphenols reported. In this example we have developed a simple and rapid strategy to isolate polyphenols from cranberry juice using soy lecithin. The polyphenol extract was obtained from the lecithin precipitate via solvent extraction and its composition was analyzed by HPLC. The recovery rate of the extracted anthocyanins was quantified across varying lecithin concentrations. We also compared the recovery rate of the anthocyanins isolated with lecithin powder, pre-dispersed lecithin, and Emulfluid® HL 66.

Methods

Reagents

Unless specified otherwise, the lecithin employed was soybean lecithin powder (Product No. J61675, Alfa Aesar, Ward Hill, Mass., U.S.A.). Emulfluid® HL 66 were from Cargill (Wayzata, Minn., U.S.A.). Methanol (HPLC grade) was from Thermo Fisher Scientific (Waltham, Mass., U.S.A.). Formic acid (reagent grade, >95%), and acetone (ACS reagent grade) were purchased from Sigma-Aldrich (St. Louis, Mo., U.S.A.). Ethanol (anhydrous, USP standard) was from Decon Labs (King of Prussia, Pa., U.S.A.). Ultrapure grade water was purified to at least 18.1 M Ω·cm using a Barnstead water filtration system (Thermo Fisher Scientific). All reagents were used without further purification except as noted.

Diluted Cranberry Juice Preparation

Single-strength cranberry juice was prepared freshly from frozen juice concentrates as described in Example 3.

Combining Lecithin Powder with Juice Samples

Powdered lecithin was added to 500 μL of juice at 1, 2, 3, 4% w/v. The mixture was vortexed for 1 min and incubated at room temperature for 5 min. It was then centrifuged at 9391×g for 1 min to pellet the precipitate.

Combining Pre-Dispersed Lecithin with Juice Samples

Lecithin powder was weighed and dissolved in 50 μL of ultrapure water to form a dispersion. They were vortexed for 30 seconds and added to 500 μL juice samples to make up a final lecithin concentration of 1, 2, 3, 4% w/v. The mixture was vortexed for 1 min and incubated at room temperature for 5 min. It was then centrifuged at 9391×g for 1 min to pellet the precipitate.

Extracting Polyphenols from Precipitate

Juice supernatant was decanted and 1 mL of 50% v/v acetone in ethanol was added to the precipitate. These solvents were selected at this proportion because the pigments were better stabilized compared to other binary solvent systems. The mixture was vortexed for 2 min and then centrifuged at 21130×g for 3 min at room temperature. The polyphenol-rich supernatant was transferred to a new 2 mL microcentrifuge tube and dried under N2 for 30 min. The tube was placed in an ice bath for 5 min and centrifuged at 4° C. at 21130×g for 3 min to remove the remaining lecithin. The final volume of the extract was recorded.

Preparation of Polyphenol Extract for HPLC Analysis

An aliquot of polyphenol extract (100 μL) was mixed with 150 μL of 5% v/v formic acid in water, followed by centrifugation at 21130×g for 1 min at room temperature. The supernatant was used for HPLC analysis.

HPLC Analysis of Anthocyanin Content in Polyphenol Extract

Anthocyanin content in the polyphenol extract was quantitated by reverse phase HPLC using a Dionex Ultimate 3000 HPLC equipped with an LPG-3400 quaternary pump, a WPS-3000 analytical autosampler, a DAD-3000 diode array detector, and an FLD-3100 fluorescence detector. A Kinetex 5 μm EVO C18, 100 A°, 250 mm×4.6 mm column (Phenomenex, Torrance, Calif., U.S.A.) was used to separate the cranberry anthocyanins. Separation was with formic acid:water (5:95, v/v) (A) and methanol (B). The flow rate was set to 1 mL/min. The gradient was initially 5% B for 1 min, then increased to 35% B over 39 min, from 35% to 95% B over the next 10 min, and held constant at 95% B for 5 min, then decreased to 5% B over 2 min, and re-equilibrated at 5% B for the remaining 8 min. The column oven was set to 30° C. The absorbance was monitored at 254, 280, 370 and 520 nm. The major cranberry anthocyanins cyanidin-3-O-galactocide, cyanidin-3-O-glucocide, cyanidin-3-O-arabinoside, peonidin-3-O-galactocide, peonidin-3-O-glucoside, peonidin-3-O-arabinoside and cyanidin were identified based on known elution order in the 520 nm chromatogram [13].

Anthocyanin Content Percentage Depletion

The depletion of anthocyanins expressed as a percentage was determined according to the following equation:

$$\% \text{ depleted} = \frac{\text{Anthocyanin Concentration}_{before} - \text{Anthocyanin Concentration}_{after\ lecithin\ treated}}{\text{Anthocyanin Concentration}_{before}} \times 100$$

Anthocyanin Content Percentage Recovery

The recovery of anthocyanins expressed as a percentage was calculated according to the following equation:

$$\% \text{ recovered} = \frac{\text{Anthocyanin Concentration}_{juice} - \text{Anthocyanin Concentration}_{extract}}{\text{Anthocyanin Concentration}_{juice}} \times 100$$

Statistical Analysis

The mean and standard error of each treatment were calculated from triplicates. Analysis of variance (ANOVA) was carried out to determine any significant differences between treatments (P<0.05).

Results

Composition of Polyphenol Extract

Figure 22:
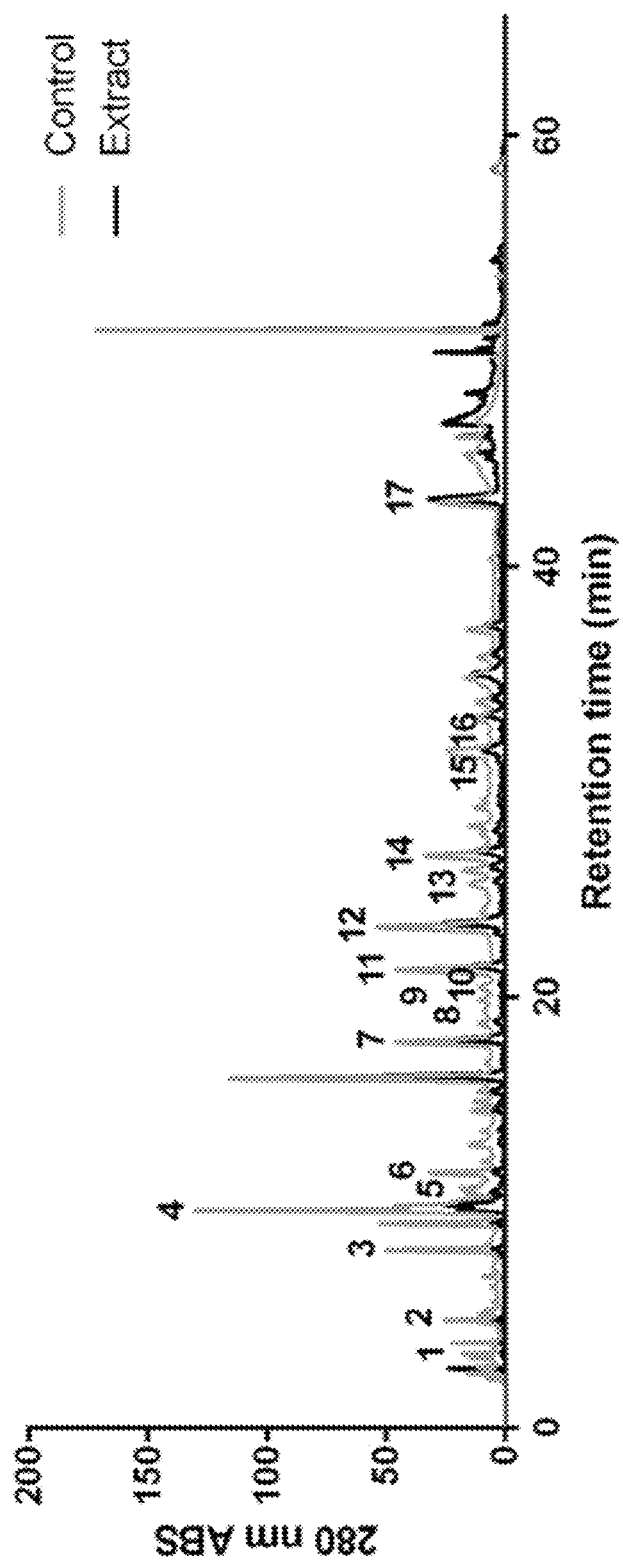
FIG. 22. Tentative peak identification of polyphenol extract and cranberry juice at 280 nm.

The polyphenol composition of the extract and the untreated cranberry juice was qualitatively analyzed by HPLC (FIG. 22). The proportion of assigned polyphenols in extract to those in control juice was calculated in Table 11. Based on the chromatogram of the polyphenol extract, the most polar compounds eluted first, including gallic acid, protocatechuic acid, catechin, caffeic acid, 3.4-dihyrdoxyphenylacetic acid, chlorogenic acid, mainly phenolic acids. The individual anthocyanins were also observed after 15 min on the chromatogram. The polyphenol extract contained delphinidin-3-O-arabinose, cyanidin-3-O-gluoside, cyanidin-3-O-galactoside, cyanidin-3-O-arabinose, peonidin-3-

O-galactoside and peonidin-3-O-arabinose. The flavonoids quercetin-3-O-galactoside, quercetin, quercetin-3-O-glucoside were also present in the extract. The proanthocyanidins were observed after 45 min. Compared to the control, the extract was specifically enriched in flavonoids and proanthocyanidins, with a small amount of phenolic acids.

TABLE 11

Comparison of polyphenols peak area under curve in control cranberry juice and

| Peak # | Peak Name | Recovery in extract/% |
|---|---|---|
| 1 | gallic acid | 42.0 ± 22.9 |
| 2 | protocatechuic acid | 32.0 ± 10.3 |
| 3 | catechin | 27.3 ± 5.1 |
| 4 | caffeic acid | 20.2 ± 4.4 |
| 5 | 3,4-dihyroxyphenyl acetic acid | 87.4 ± 18.4 |
| 6 | chlorogenic acid | 36.0 ± 12.8 |
| 7 | cyanidin-3-O-galactoside | 59.6 ± 11.6 |
| 8 | delphinidin-3-O-arabinoside | 22.1 ± 4.4 |
| 9 | cyanidin-3-O-glucoside | 35.0 ± 8.9 |
| 10 | ferulic acid | 44.7 ± 11.6 |
| 11 | cyanidin-3-O-arabinoside | 36.3 ± 3.6 |
| 12 | peonidin-3-O-galactoside | 58.6 ± 7.3 |
| 13 | peonidin-3-O-glucoside | 43.5 ± 13.2 |
| 14 | peonidin-3-O-arabinoside | 45.8 ± 3.5 |
| 15 | quercetin-3-O-galactoside | 111.5 ± 18.3 |

TABLE 11-continued

Comparison of polyphenols peak area under curve in control cranberry juice and

| Peak # | Peak Name | Recovery in extract/% |
|---|---|---|
| 16 | quercetin-3-O-glucoside | 82.5 ± 22.8 |
| 17 | quercetin | 100.1 ± 2.9 |

[1]Data are mean ± standard error from triplicates.

Anthocyanin Content in Polyphenol Extract Using Powder Lecithin

The lecithin powder was used to precipitate cranberry juice polyphenols, and then extracted with 50/50 acetone in ethanol to determine recovery (Table 12). The total anthocyanin content in 500 μL untreated cranberry juice was 96.8±0.8 μg. At 1% lecithin, the anthocyanins remaining in the decanted supernatant after precipitation decreased to 39.3±1.1 μg, leaving 57.5±1.9 μg in the precipitate. From this, 28.5±2.2 μg of the original anthocyanins was recovered by solvent extraction. Increasing lecithin amount from 1% to 4% w/v increased depletion of the supernatant, up to 76.7±1.2% of the anthocyanins from the cranberry juice. However, increasing lecithin concentrations reduced the efficiency of solvent extraction, leading to a recovery of 18.0±0.9% of the total anthocyanins.

TABLE 12

Anthocyanins extracted and depleted by powder lecithin.[1,2]

| Lecithin % w/v | Supernatant anthocyanins (μg) | % Depleted | Precipitated anthocyanins (μg) | Precipitated anthocyanins (μg/mg lecithin) | Extract anthocyanins (μg) | % Recovered |
|---|---|---|---|---|---|---|
| 0 | 96.8 ± 0.8 | — | — | — | — | — |
| 1 | 39.3 ± 1.1 | 59.4 ± 1.1 | 57.5 ± 1.9 | 11.5 ± 0.4 | 28.5 ± 2.2 | 29.4 ± 2.3[a] |
| 2 | 26.4 ± 0.5 | 72.7 ± 0.5 | 70.4 ± 1.3 | 7.04 ± 0.1 | 26.0 ± 1.9 | 26.9 ± 1.9[a] |
| 3 | 25.1 ± 1.2 | 74.0 ± 1.2 | 71.7 ± 1.9 | 4.78 ± 0.1 | 21.1 ± 1.1 | 21.8 ± 1.2[b] |
| 4 | 22.6 ± 1.2 | 76.7 ± 1.2 | 74.2 ± 2.0 | 3.71 ± 0.1 | 17.4 ± 0.8 | 18.0 ± 0.9[b] |

[1]Total (μg) = Anthocyanin content in untreated cranberry juice.
[2]Data are mean ± standard error from triplicates. Different superscript letters in the same row indicate significate differences in the mean (P < 0.05).

Anthocyanin Content in Polyphenol Extract Using Pre-Dispersed Lecithin

Next, the extent that pre-dispersed lecithin depleted cranberry juice anthocyanins was evaluated (Table 13). In this experiment, the total anthocyanin content was 73.0±0.1 μg. The juice anthocyanin content was depleted by 65.1±4.31% by 1% w/v lecithin, where 47.5±4.4 μg of the anthocyanins was precipitated. From the precipitate, 24.9±1.6 μg was recovered, which accounted for 34.1±1.6% of the original juice anthocyanins. The recovery decreased to 18.1±1.7% when the lecithin was increased to 4% w/v.

TABLE 13

Anthocyanins extracted and depleted by pre-dispersed lecithin.[1,2]

| Lecithin % w/v | Supernatant anthocyanins (μg) | % Depleted | Precipitated anthocyanins (μg) | Precipitated anthocyanins (μg/mg lecithin) | Extract anthocyanins (μg) | % Recovered |
|---|---|---|---|---|---|---|
| 0 | 73.0 ± 0.1 | — | — | — | — | — |
| 1 | 25.5 ± 3.6 | 65.1 ± 4.3 | 47.5 ± 4.4 | 9.50 ± 0.9 | 24.9 ± 1.6 | 34.1 ± 1.6[a] |
| 2 | 19.7 ± 0.7 | 72.9 ± 0.9 | 53.2 ± 1.0 | 5.31 ± 0.1 | 21.0 ± 0.4 | 28.8 ± 0.4[b] |

TABLE 13-continued

Anthocyanins extracted and depleted by pre-dispersed lecithin.[1,2]

| Lecithin % w/v | Supernatant anthocyanins (μg) | % Depleted | Precipitated anthocyanins (μg) | Precipitated anthocyanins (μg/mg lecithin) | Extract anthocyanins (μg) | % Recovered |
|---|---|---|---|---|---|---|
| 3 | 18.0 ± 1.1 | 75.3 ± 1.2 | 55.0 ± 1.3 | 3.67 ± 0.1 | 15.7 ± 2.2 | 21.5 ± 2.6[c] |
| 4 | 17.2 ± 0.9 | 76.5 ± 1.1 | 55.8 ± 1.2 | 2.79 ± 0.1 | 13.2 ± 1.4 | 18.1 ± 1.7[c] |

[1]Total (ug) = Anthocyanin content in untreated cranberry juice.
[2]Numbers are mean ± standard error from triplicates. Different superscript letters in the same row indicate significate differences in the mean. (P < 0.05).

Recovery Rate of Anthocyanins Using Lecithins in Different Forms

The recovery of anthocyanin from the precipitate of Emulfluid® HL 66 at 1% (w/v) was 34.2% (Table 14), which was no different than the other lecithin treatments at 1% w/v.

TABLE 14

Comparison of anthocyanin depletion and recovery rate extracted by lecithins at 1% w/v.[1]

| Lecithin form | % Depleted | % Recovered |
|---|---|---|
| Powder-soy lecithin | 59.4 ± 1.10[b] | 29.4 ± 2.3[a] |
| Dispersion-soy lecithin | 65.1 ± 4.31[b] | 34.1 ± 1.6[a] |
| Emulfluid ® HL 66 | 73.1 ± 2.21[a] | 34.2 ± 3.7[a] |

[1]Numbers are mean ± standard error from triplicates. Same superscript letters in the same column indicate no significant different in the mean (P > 0.05).

Extraction Solvents

Solutions of glucose at 15-55 brix solutions (glucose) in water did not aid polyphenol recovery from the polyphenol-lecithin precipitate. The increased density of the aqueous phase at ≥30 brix could be used to isolate polyphenol-lecithin precipitate on the surface of the aqueous phase.

Ethanol, acetone, ethyl acetate, acidic water, acidic methanol, dimethylsulfoxide (DMSO) only partly solubilize lecithin and therefore served as suitable extraction solvents. Among these, ethanol, acetone, and acidic methanol recovered the most pigmentation from cranberry juice lecithin precipitate.

Mixtures of ethanol & acetone were tested at various relative concentrations: 30%, 40%, 50% ethanol in acetone, v/v. Among these, the 40% and 50% solutions were superior in solubilizing pigment while limiting pellet dissolution.

Discussion

Polyphenols were recovered from cranberry juice by lecithin followed by solvent extraction of the lecithin precipitate. The polyphenol composition of the solvent extract was analyzed qualitatively. We found that the extract was rich in anthocyanins, flavonoids and proanthocyanidins, with less phenolic acids compared with the polyphenol profile in the control cranberry juice. The results corroborate with data from research Example 4 where we found that lecithin interact with a variety of polyphenols, including anthocyanins, flavonoids and proanthocyanidins, but did not interact with gallic acid. However, a small amount of gallic acid, protocatechuic acid, caffeic acid and chlorogenic acid were present in the polyphenol extract. Most phenolic acids did not appear in the extract, which results from their inability to interact with two phospholipid molecules. Thus, the resulting extract was preferentially enriched in anthocyanins, flavonols, and proanthocyanidins. Although these data are qualitative, the results confirm our previous findings.

Water, methanol, ethanol, acetone, 50% aqueous methanol, 50% aqueous ethanol and 50% aqueous acetone are common solvents to extract polyphenols from the food matrix [14, 15]. Do et al. reported maximum yield of extraction with the order of 50% aqueous acetone, 50% aqueous methanol, 50% aqueous methanol. The combined use of water and organic solvent facilitated the extraction of polyphenol compounds from plants [16]. The present example utilized 1:1 acetone/ethanol, v/v, to extract polyphenols from the lecithin precipitate. Lecithin has limited solubility in these two solvents [17]. Since lecithin is water soluble, it is not a desirable solvent for this system [18]. Future work should determine the co-extraction of phospholipids in this system. Some phospholipids, for example PC, are soluble in ethanol [19]. The extract might contain a small fraction of phospholipids, sugars, and other components in the aqueous that could interact with the phospholipids. Therefore, we still need to determine the purity of the extract.

The method of lecithin addition is an important factor for recovery of polyphenols. The absolute level of lecithin in solution was the most important factor governing anthocyanin recovery in solvent extracts of precipitate. Although increasing lecithin content increased anthocyanin precipitation, these additional anthocyanins were not readily extractable with solvent. The extent of polyphenol extraction depends on the solvent polarity, pH, temperature, and extraction time [20]. It is possible that extraction recovery could be increased by modifying the extraction conditions used in the present example. In example, Oancea et al. demonstrated increased anthocyanin recovery from blueberry by using high temperatures, longer extraction times, and protection from light [21].

We hypothesized recovery would be related to the ability of lecithins to deplete anthocyanins from juice. Emulfluid® HL 66 depleted significantly higher amount of anthocyanins compared to soy lecithins Despite this, the recovery of anthocyanins from extracted Emulfluid® HL 66 was similar to conventional soy lecithin. Likewise, direct addition or pre-solubilizaton of lecithin did not impact recovery. Thus, surprisingly, extraction efficiency is not related to lecithin type or dispersion method. This would imply that the lecithin-polyphenol interactions at the amphiphilic heads may govern their release into ethanol/acetone. The results also indicated that lecithin pre-solubilization is not necessary for the interaction to occur because there is no significant percentage depletion difference by direct addition or pre-solubilization of lecithin.

Conclusion

In conclusion, up to 34% of cranberry juice anthocyanins could be recovered from cranberry juice by lecithin addition and subsequent extraction by solvent. Unlike other extraction techniques, the extraction method we introduced involves simply mixing and separation of the soluble polyphenols from insoluble phospholipids by solvent extraction. This method would be useful for manufacturers in food industry to produce vegetable/fruit extracts. However, further attempts should focus on improving the yield of the extractability in order to achieve a cost-effective approach for industry use.

REFERENCES

[1]. Cravotto, G., Binello, A., Orio, L. Green extraction techniques. Agro. Food Ind. Hi-Tech. 2011, 22, 57-59.
[2]. Herrero, M., Mendiola, J. A., Cifuentes, A., Ibáñez, E. Supercritical fluid extraction: recent advances and applications. J. Chromatogr. A. 2010, 1217, 2495-2511.
[3]. Sairam, P., Ghosh, S., Jena, S., Rao, K. N. V., Banji, D. Supercritical fluid extraction (SFE)—an overview. J. Res. Pharma. Sci. 2012, 2, 112-120.
[4]. King, J. W. Modern supercritical fluid technology for food applications. Annu. Rev. Food Sci. Technol. 2014, 5, 215-238.
[5]. Vilkhu, K., Mawson, R., Simons, L., Bates, D. Applications and opportunities for ultrasound-assisted extraction in the food industry—a review. Innov. Food Sci. Emerg. Technol. 2008, 9, 161-169.
[6]. Tadeo, J. L., Sánchez-Brunete, C., Albero, B., Garcia-Valcárcel, A. I. Application of ultrasound-assisted extraction to the determination of contaminants in food and soil samples. J. Chromatogr. A. 2010, 1217, 2415-2440
[7]. Kentish, S., Feng, H. Applications of power ultrasound in food processing. Annu. Rev. Food Sci. Technol. 2014, 5, 263-284.
[8]. Awad, T. S., Moharram, H. A., Shaltout, O. E., Asker, D., Youssef, M. M. Applications of ultrasound in analysis, processing and quality control of food: a review. Food Res. Int. 2012, 48, 410-427.
[9]. Teo, C. C., Tan, S. N., Yong, J. W., Hew, C. S., Ong, E. S. Pressurized hot water extraction (PHWE). J. Chromatogr. A. 2010, 1217, 2484-2494.
[10]. Plaza, M., Turner, C. Pressurized hot water extraction of bioactives. Trend Anal Chem. 2015, 71, 39-54.
[11]. Plaza. M., Abrahamsson, V., Turner, C. Extraction and neoformation of antioxidant compounds by pressurized hot water extraction from apple byproducts. J. Agric. Food Chem. 2013, 61, 5500-5510
[12]. Vergara-Salinas, J. R., Cuevas-Valenzuela, J., Pérez-Correa, J. R. Pressurized hot water extraction of polyphenols from plant material. In: Kumar V G, Tuohy M G, Lohani M, O'Donovan A, editors. Biotechnology of bioactive compounds: sources and applications. New Jersey: John Wiley & Sons Inc. 2015, 63-101.
[13]. Wu, X., Prior, R. L. Systematic identification and characterization of anthocyanins by HPLC-ESI-MS/MS in common foods in the United States: Fruits and berries. Journal of Agricultural and Food Chemistry. 2005, 53, 2589-2599.
[14]. Zlotek, U., Mikulska, S., Nagajek, M., Świeca, M. The effect of different solvents and number of extraction steps on the polyphenol content and antioxidant capacity of basil leaves (Ocimum basilicum L.) extracts. Saudi Journal of Biological Sciences. 2016, 23, 628-633.
[15]. Revilla, E., Ryan, J. M., Martin, O. G. Comparison of several procedures used for the extraction of anthocyanins from red grapes. J. Agric. Food Chem. 1998, 46, 4592-4596.
[16]. Do, Q. D., Angkawijaya, A. E., Tran-Nguygen, P. L. et al. Effect of extraction solvent on total phenol content, total flavonoid content, and antioxidant activity of Limnophilia aromatica. J. Food and Drug Analysis. 2014, 22, 296-302.
[17]. Schneider, M. Fractionation and Purification of Lecithin, in Lecithins: Sources, Manufacture, & Uses, edited by B. F. Szuhaj, American Oil Chemists' Society, Champaign, 1989, 109-130.
[18]. Kass, G. S. Water soluble lecithin composition. U.S. Pat. No. 4,174,296A (1978).
[19]. Liu, D., Ma, F. Soybean Phospholipids. In Recent Trends for Enhancing the Diversity and Quality of Soybean Products; Krezhova, D., Ed.; InTech: Rijeka, Croatia (2011).
[20]. Stalikas, C. D. Extraction, separation, and detection methods for phenolic acids and flavonoids. J. Sep. Sci. 2007, 30, 3268-3295.
[21]. Oancea, S., Stoia, M., Coman, D. Effects of extraction conditions on bioactive anthocyanin content of Vaccinium Corymbosum in the perspective of food applications. Procedia Engineering. 2012, 42, 489-495.

Example 7: Conclusions

Discussion

This example focused on the ability of phospholipid surfactants to be used in the extraction of polyphenol compounds and their reaction mechanism. The addition of lecithin phospholipids to polyphenols in cranberry juice induced precipitate formation and pigmentation loss. At low lecithin concentrations (1-2%, w/v), the hydrophilicity of lecithins enhances these interactions, by increasing phospholipid-polyphenol interactions. In contrast, other common surfactants used in foods did not significantly deplete polyphenols, which implies that the unique structure of lecithin phospholipids is essential for sequestering polyphenols from solutions.

In addition, polyphenol-lecithin interactions occur in aqueous solutions with single polyphenols, independent of the juice matrix. Polyphenols including stilbenes, flavonol glycosides, flavan-3-ols and proanthocyanidins were found to have the strongest interaction with phospholipids. Although we expected hydrophobic interactions between the polyphenols and the phospholipids, there was no strong relationship found between polyphenol depletion and its hydrophobicity. This result contradicts pervious work by Yu et al., who concluded the strength of the interaction is inversely related to the polarity of the polyphenol [1]. However, data suggested that the polyphenol's affinity to the phospholipid membrane depends on the hydrogen bonding capacity and molecular geometry of the polyphenols. The phenolic hydroxyl group was integral to the formation of hydrogen bonds between the polyphenols and the phosphate group on the phospholipids [2, 3]. Anthocyanins, quercetin-3-galactoside, (+)-catechin, genistein, quercetin and resveratrol in aqueous solutions were significantly depleted by lecithin. However, gallic acid and quercetin-3-rutinoside did not induce precipitation of lecithin phospholipids, possibly due to their molecular geometry.

This research also described how solutes and pH of aqueous systems affect the phospholipid-polyphenol interaction. The phospholipid-polyphenol interaction is affected by hydrogen bonding, where the change of pH and ionic strength lead to the weakening of hydrogen bonds between charged phosphate group of the phospholipid and the polyphenols [4, 5]. Although alcohol content favors the phospholipid-polyphenol interaction, the same outcome was not observed in alcoholic drinks containing polyphenols, which suggested the complex nature of the aqueous systems might interfere the hydrogen bonding between phospholipid and polyphenols [6].

With the interaction between lecithin phospholipids and polyphenols, we developed a simple and rapid polyphenol extraction method that isolated polyphenols from cranberry juice. The resulting extract is rich in flavonoids due to the strong interaction with the phospholipids [7-9]. The current limitation to this method is that the purity of the extract needs to be examined further. In addition to polyphenols, the extract might contain residual sugars and some organic acids. The remaining phospholipid content, sugar content and other possible impurities need to be quantified. Furthermore, testing the stability of pigments present in the extract would be helpful to develop use of the extract in food applications. Future experiments should also seek to expand its use in various polyphenol-rich systems as well as fruit, vegetable, and plant waste that could serve as excellent sources of natural antioxidant ingredients.

Our results suggest that the various polyphenols interact with the phospholipids by hydrogen-bonding models rather than hydrophobic interactions. The level of interaction is dependent on structural features of the polyphenols and the hydrophilicity of the phospholipids. The results also suggest the bioavailability of the polyphenols may be increased by the tendency to interact with phospholipid bilayers [10, 11].

The polyphenol-lecithin precipitate can be used directly for addition to foods or dietary supplements. For example, lecithin may be used as a base encapsulating ingredient in chewing gum to carry flavors or nutraceuticals (see U.S. Pat. No. 6,703,000 B2). Altering the lecithin type used for precipitating polyphenols could alter the delivery or bioavailability of polyphenol components. This property of polyphenol-lecithin material could be useful in formulating polyphenol-rich dietary supplements or foods. Delayed or selective release could be optimized to deliver polyphenols to different parts of the digestive system (e.g. oral cavity, stomach, small intestine, or colon). Furthermore, for colorant use, the polyphenol-lecithin precipitate is pigmented, so could be applied directly to infuse colorant into desired products. Alternatively, the polyphenol can be extracted from the polyphenol-lecithin precipitate and used as a purified substance.

REFERENCES

[1]. Yu, X., Chu, S., Hagerman, A. E., Lorigan, G. A. Probing the Interaction of Polyphenols with Lipid Bilayers by Solid-state NMR Spectroscopy. J. Agric. Food. Chem. 2011, 59, 6783-6789.

[2]. Pu, Y., Zhang, X., Zhang, Q. 20(S)-Proropanaxadiol Phospholipid Complex: Process Optimization, Characterization, in vitro Dissolution and Molecular Docking Studies. Molecules, 2016, 21, 1396-1417.

[3]. Mrazkova, E., Hobza, P., Bohl, M., Gauger, D. R., Pohle, W. Hydration-Induced Changes of Structure and Vibrational Frequencies of Methylphosphocholine Studied as a Model of Biomembrane Lipids. J. Phys. Chem. B. 2005, 109, 15126-15134.

[4]. Melcrova, A., Pokorna, S., Pullanchery, S., Kohagen, M., Jurkiewicz, P., Hof, M., Jungwirth, P., Cremer, P. S., Cwiklik, L. The Complex Nature of Calcium Cation Interactions with Phospholipid Bilayers. Sci Rep. 2016, 6, 38035-38047.

[5]. Nose, A., Hojo, M. Hydrogen bonding of water-ethanol in alcoholic beverages. J. Biosci. Bioeng. 2006, 102, 269-280.

[6]. de Granada-Flor, A., Sousa, C., Filipe, H. A. L., Santos, M. S., de Almeida, R. F. M. Quercetin dual interaction at the membrane level. Chemical Communications. 2019, 55, 1750-1753.

[7]. Pawlikowska-Pawlega, B., Kapral, J., Gawron, A. et al. Interaction of a quercetin derivative—lensoside Aβ with liposomal membranes. Biochimica et Biophysica Acta (BBA)—Biomembranes. 2018, 1860, 292-299.

[8]. Košinová, P., Berka, K., Wykes, M. et al. Positioning of antioxidant Quercetin and its metabolites in lipid bilayer membranes: implication for their lipid-peroxidation inhibition. J. Phys. Chem. B. 2012, 116, 1309-1318.

[9]. Lu, M., Qiu, Q., Luo, X., Liu, X., Sun, J., Wang, C., Lin, X., Deng, Y., Song, Y. Phyto-phospholipid complexes (phytosomes): A novel strategy to improve the bioavailability of active constituents. Asian Journal of Pharmaceutical Sciences. 2019, 14, 265-274.

[10]. Apostolova, E., Spaseska, B., Crcarevska, M. S., Dodov, M. G., Raichki, R. S. An overview of phytosomes as a novel herbal drug delivery system. International Symposium at Faculty of Medical Sciences. 2015, 1, 95-96.

[11]. Maiti, K., Mukherjee, K., Gantait, A., Saha, B. P., Mukherjee, P. K. Curcumin-phospholipid complex: preparation, therapeutic evaluation and pharmacokinetic study in rats. Int J Pharma. 2007, 330, 155-163.

ADDITIONAL REFERENCES

Martin, D. A., Smyth, J. A., Liu, Z., Bolling, B. W. (2018). Aronia Berry (Aronia Mitschurinii 'Viking') Inhibits Colitis in Mice and Inhibits T Cell Tumor Necrosis Factor-α Secretion. *Journal of Functional Foods*, 44(February), 48-57. doi: 10.1016/j.jff.2018.02.025

Rodriguez-Saona, L., & Wrolstad, R. (2001). Extraction, Isolation, and Purification of Anthocyanins. In R. E. Wrolstad, T. E. Acree, E. A. Decker, M. H. Penner, D. S. Reid, S. J. Schwartz, C. F. Shoemaker, D. Smith, P. Spors (Eds.), *Handbook of Food Analytical Chemistry: Pigments, Colorants, Flavors, Texture, and Bioactive Food Components* (pp. 5-69). Hoboken, N.J.: John Wiley & Sons, Inc.

Wu, Yuwei. (2020). Phospholipid Induced Polyphenol Precipitation and Its Potential Reaction Mechanism. Master's Thesis. University of Wisconsin-Madison.

EXEMPLARY EMBODIMENTS OF THE INVENTION

Exemplary embodiments of the invention are as follows:

1. A method of isolating phenols from a phenol-containing medium, the method comprising: combining a phospholipid-containing composition with the phenol-containing medium to generate a combined medium; incubating the combined medium to precipitate phenols in the combined medium and thereby form a phenol precipitate phase and a phenol-depleted phase; and separating the phenol precipitate phase and the phenol-depleted phase.

2. The method of exemplary embodiment 1, wherein the phospholipid-containing composition comprises one or more of phosphatidylcholine, phosphoinositide, phosphatidylethanolamine, phosphatidylserine, and phosphatidic acid.

3. The method of any prior exemplary embodiment, wherein the phospholipid-containing composition comprises one or more of phosphatidylcholine, phosphoinositide, and phosphatidylethanolamine.

4. The method of any prior exemplary embodiment, wherein the phospholipid-containing composition comprises phosphoinositide.

5. The method of any prior exemplary embodiment, wherein the phospholipid-containing composition comprises each of phosphatidylcholine, phosphoinositide, and phosphatidylethanolamine.

6. The method of any prior exemplary embodiment, wherein the phospholipid-containing composition comprises negatively charged phospholipid in an amount of at least about 20% w/w of the phospholipid-containing composition.

7. The method of any prior exemplary embodiment, wherein the phospholipid-containing composition comprises phosphoinositide in an amount of at least about 20% w/w of the phospholipid-containing composition.

8. The method of any prior exemplary embodiment, wherein the phospholipid-containing composition comprises phospholipid with a substituted hydrocarbon chain.

9. The method of any prior exemplary embodiment, wherein the phospholipid-containing composition comprises a hydroxylated phospholipid.

10. The method of exemplary embodiment 9, wherein the phospholipid-containing composition includes the hydroxylated phospholipid in an amount of at least 40% w/w of the composition.

11. The method of any prior exemplary embodiment, wherein the phospholipid-containing composition further comprises triglyceride.

12. The method of any prior exemplary embodiment, wherein the phospholipid-containing composition is or includes lecithin.

13. The method of any prior exemplary embodiment, wherein the phospholipid-containing composition is or includes chemically modified lecithin.

14. The method of any prior exemplary embodiment, wherein the phospholipid-containing composition is or includes hydroxylated lecithin.

15. The method of any prior exemplary embodiment, wherein the phospholipid-containing composition has a hydrophilic-lipophilic balance (HLB) greater than 3.

16. The method of any prior exemplary embodiment, wherein the phospholipid-containing composition has a hydrophilic-lipophilic balance (HLB) of 4-30.

17. The method of any prior exemplary embodiment, wherein the phospholipid-containing composition has a hydrophilic-lipophilic balance (HLB) of 7-30.

18. The method of any prior exemplary embodiment, wherein the phospholipid-containing composition is combined with the phenol-containing medium in an amount of 0.3-20% w/v of the phenol-containing medium.

19. The method of any prior exemplary embodiment, wherein the phenol-containing medium is an aqueous medium.

20. The method of any prior exemplary embodiment, wherein the phenol-containing medium is a liquid.

21. The method of any prior exemplary embodiment, wherein the phenol-containing medium comprises a fruit juice, a vegetable juice, blanch water, or a botanical extract.

22. The method of any prior exemplary embodiment, wherein the phenol precipitate phase comprises a polyphenol.

23. The method of any prior exemplary embodiment, wherein the phenol precipitate phase comprises a flavonoid.

24. The method of any prior exemplary embodiment, wherein the phenol precipitate phase comprises an anthocyanin, an anthocyanidin, a proanthocyanidin, or a combination thereof.

25. The method of any prior exemplary embodiment, wherein total phenol mass concentration in the phenol-depleted phase is at least 30% less than total phenol mass concentration in the phenol-containing medium.

26. The method of any prior exemplary embodiment, wherein monomeric anthocyanin mass concentration in the phenol-depleted phase is at least 30% less than monomeric anthocyanin mass concentration in the phenol-containing medium.

27. The method of any prior exemplary embodiment, wherein proanthocyanidin mass concentration in the phenol-depleted phase is at least 30% less than proanthocyanidin mass concentration in the phenol-containing medium.

28. The method of any prior exemplary embodiment, wherein the separating comprises one or more of centrifuging the phenol precipitate phase and the phenol-depleted phase to pellet the phenol precipitate phase, decanting or aspirating the phenol-depleted phase from the phenol precipitate phase, and filtering the phenol precipitate phase from the phenol-depleted phase.

29. The method of any prior exemplary embodiment, further comprising, between the combining and the separating, mixing the phospholipid-containing composition and the phenol-containing medium.

30. The method of any prior exemplary embodiment, wherein the incubating is performed at a temperature of about 0-17° C.

31. The method of any prior exemplary embodiment, wherein the phenol-containing medium has a sugar content of less than 50° Brix.

32. The method of any prior exemplary embodiment, wherein the phenol-containing medium comprises alcohol.

33. The method of any prior exemplary embodiment, further comprising combining pectin with the phospholipid-containing composition and the phenol-containing medium to generate the combined medium.

34. The method of exemplary embodiment 33, wherein the pectin is added in an amount effective to increase precipitation of the phenols in the combined medium compared to precipitation in an otherwise identical medium lacking the pectin.

35. The method of any prior exemplary embodiment, further comprising extracting phenols from the separated phenol precipitate phase, wherein the extracting comprises mixing the separated phenol precipitate phase with an extraction solvent to solubilize in the extraction solvent at least a portion of the phenols originally present in the phenol precipitate phase.

36. The method of exemplary embodiment 35, wherein the extraction solvent comprises an organic solvent.

37. The method of any one of exemplary embodiments 35 and 36, wherein the extraction solvent comprises an alcohol.

38. The method of any one of exemplary embodiments 35-37, wherein the extraction solvent comprises acetone.

39. The method of any one of exemplary embodiments 35-38, wherein the extraction solvent comprises one or more of ethanol, acetone, and methanol.

40. The method of any one of exemplary embodiments 35-39, wherein the extraction solvent comprises ethanol and acetone.

41. The method of any one of exemplary embodiments 35-40, wherein the extraction solvent comprises an alcohol, such as ethanol, and acetone in a combined amount of at least about 80% v/v.

42. The method of any one of exemplary embodiments 35-41, wherein the extraction solvent comprises alcohol, such as ethanol, in an amount of at least about 20% v/v and acetone in an amount of at least about 20% v/v.

43. The method of any one of exemplary embodiments 35-42, wherein the extraction solvent comprises water in an amount less than 20% v/v.

44. The method of any one of exemplary embodiments 35-43, wherein the separated phenol precipitate phase comprises the phenols and phospholipid and the mixing the separated phenol precipitate phase with the extraction solvent preferentially solubilizes the phenols over the phospholipid in the extraction solvent.

45. The method of any one of exemplary embodiments 35-44, further comprising separating at least a portion of the extraction solvent from the phenols solubilized therein.

46. A composition comprising isolated phenol, wherein the isolated phenol comprises or consists of the separated phenol precipitate phase as recited in any one of exemplary embodiments 1-34, the phenols solubilized in the extraction solvent as recited in any one of exemplary embodiments 35-44, or the phenols separated from the extraction solvent as recited exemplary embodiment 45.

47. A phenol-phospholipid complex, comprising phenol complexed with phospholipid.

48. The phenol-phospholipid complex of exemplary embodiment 47, wherein the phospholipid comprises one or more of phosphatidylcholine, phosphoinositide, phosphatidylethanolamine, phosphatidylserine, and phosphatidic acid.

49. The phenol-phospholipid complex of any one of exemplary embodiments 47-48, wherein the phospholipid comprises phosphoinositide.

50. The phenol-phospholipid complex of any one of exemplary embodiments 47-49, wherein the phenol comprises a polyphenol.

51. The phenol-phospholipid complex of any one of exemplary embodiments 47-50, wherein the phenol comprises a flavonoid.

52. The phenol-phospholipid complex of any one of exemplary embodiments 47-50, wherein the phenol comprises an anthocyanin, an anthocyanidin, a proanthocyanidin, or a combination thereof.

53. The phenol-phospholipid complex of any one of exemplary embodiments 47-52, made from the method of any one of exemplary embodiments 1-34.

What is claimed is:

1. A method of isolating phenols from a phenol-containing medium, the method comprising:
combining a phospholipid-containing composition with the phenol-containing medium to generate a combined medium;
incubating the combined medium to precipitate phenols in the combined medium and thereby form a phenol precipitate phase and a phenol-depleted phase;
separating the phenol precipitate phase and the phenol-depleted phase; and
extracting phenols from the separated phenol precipitate phase, wherein the extracting comprises mixing the separated phenol precipitate phase with an extraction solvent to solubilize in the extraction solvent at least a portion of the phenols originally present in the phenol precipitate phase.

2. The method of claim 1, wherein the phospholipid-containing composition comprises negatively charged phospholipid.

3. The method of claim 1, wherein the phospholipid-containing composition comprises phosphoinositide.

4. The method of claim 1, wherein the phospholipid-containing composition comprises hydroxylated phospholipid.

5. The method of claim 1, wherein the phospholipid-containing composition is or includes lecithin.

6. The method of claim 5, wherein the lecithin comprises chemically modified lecithin.

7. The method of claim 5, wherein the lecithin comprises hydroxylated lecithin.

8. The method of claim 1, wherein the phospholipid-containing composition has a hydrophilic-lipophilic balance (HLB) greater than 3.

9. The method of claim 1, wherein the phenol precipitate phase comprises a polyphenol.

10. The method of claim 1, wherein the phenol precipitate phase comprises a flavonoid.

11. The method of claim 1, wherein the phenol precipitate phase comprises an anthocyanin, an anthocyanidin, a proanthocyanidin, or a combination thereof.

12. The method of claim 1, wherein total phenol mass concentration in the phenol-depleted phase is at least 30% less than total phenol mass concentration in the phenol-containing medium.

13. The method of claim 1, wherein the incubating is performed at a temperature of about 0-17° C.

14. The method of claim 1, wherein the phenol-containing medium comprises alcohol.

15. The method of claim 1, further comprising combining pectin with the phospholipid-containing composition and the phenol-containing medium to generate the combined medium.

16. The method of claim 1, wherein the extraction solvent comprises an organic solvent.

17. The method of claim 1, wherein the extraction solvent comprises at least one of an alcohol and acetone.

18. The method of claim 1, wherein the extraction solvent comprises water in an amount less than 20% v/v.

19. The method of claim 1, wherein the separated phenol precipitate phase comprises the phenols and phospholipid and the mixing the separated phenol precipitate phase with the extraction solvent preferentially solubilizes the phenols over the phospholipid in the extraction solvent.

20. The method of claim 1, wherein:
the phospholipid-containing composition comprises negatively charged phospholipid;
the phospholipid-containing composition has a hydrophilic-lipophilic balance (HLB) greater than 3;
total phenol mass concentration in the phenol-depleted phase is at least 30% less than total phenol mass concentration in the phenol-containing medium;
the extraction solvent comprises an alcohol and acetone;
the separated phenol precipitate phase comprises the phenols and phospholipid and the mixing the separated phenol precipitate phase with the extraction solvent preferentially solubilizes the phenols over the phospholipid in the extraction solvent.

* * * * *